(12) United States Patent
Schabert et al.

(10) Patent No.: US 12,358,940 B2
(45) Date of Patent: *Jul. 15, 2025

(54) METHOD OF MAKING NICOTINAMIDE RIBOFURANOSIDE SALTS, NICOTINAMIDE RIBOFURANOSIDE SALTS AS SUCH, AND USES THEREOF

(71) Applicant: Biosynth AG, Staad (CH)

(72) Inventors: Günter Schabert, Goldach (CH); Urs Spitz, St. Gallen (CH); Aysel Soydemir, Rorschach (CH); Iris Zimmermann, Bregenz (AT)

(73) Assignee: Biosynth AG, Staad (CH)

(*) Notice: Subject to any disclaimer, the term of this patent is extended or adjusted under 35 U.S.C. 154(b) by 0 days.

This patent is subject to a terminal disclaimer.

(21) Appl. No.: 18/963,281

(22) Filed: Nov. 27, 2024

(65) Prior Publication Data
US 2025/0092079 A1    Mar. 20, 2025

Related U.S. Application Data

(63) Continuation of application No. 17/576,699, filed on Jan. 14, 2022, which is a continuation of application No. PCT/EP2020/070451, filed on Jul. 20, 2020.

(30) Foreign Application Priority Data

Jul. 19, 2019   (EP) ..................... 19187314
Oct. 31, 2019   (EP) ..................... 19206542

(51) Int. Cl.
    *C07H 19/048*     (2006.01)
    *C07H 1/06*     (2006.01)

(52) U.S. Cl.
    CPC ............ *C07H 19/048* (2013.01); *C07H 1/06* (2013.01)

(58) Field of Classification Search
None
See application file for complete search history.

(56) References Cited

U.S. PATENT DOCUMENTS

| | | |
|---|---|---|
| 7,544,497 B2 | 6/2009 | Sinclair et al. |
| 7,652,049 B2 | 1/2010 | Ali et al. |
| 7,915,271 B2 | 3/2011 | Ali et al. |
| 8,106,184 B2 | 1/2012 | Sauve et al. |
| 8,114,626 B2 | 2/2012 | Brenner et al. |
| 8,197,807 B2 | 6/2012 | Brenner |
| 8,383,086 B2 | 2/2013 | Brenner et al. |
| 8,735,435 B2 | 5/2014 | Ali et al. |
| 8,846,724 B2 | 9/2014 | Sinclair et al. |
| 8,889,126 B2 | 11/2014 | Milbrandt et al. |
| 9,000,147 B2 | 4/2015 | Sauve et al. |
| 9,241,916 B2 | 1/2016 | Sinclair et al. |
| 9,295,688 B2 | 3/2016 | Milbrandt et al. |
| 9,321,797 B2 | 4/2016 | Sauve et al. |
| 9,597,347 B2 | 3/2017 | Sinclair et al. |
| 9,855,289 B2 | 1/2018 | Normington et al. |
| 9,861,651 B2 | 1/2018 | Brown et al. |
| 9,877,981 B2 | 1/2018 | Sinclair et al. |
| 9,919,003 B2 | 3/2018 | Normington et al. |
| 9,975,915 B1 | 5/2018 | Migaud et al. |
| 10,000,520 B2 | 6/2018 | Migaud et al. |
| 10,189,872 B2 | 1/2019 | Carlson et al. |
| 10,233,207 B2 | 3/2019 | Carlson et al. |
| 10,316,054 B2 | 6/2019 | Szczepankiewicz et al. |
| 10,323,058 B2 | 6/2019 | Carlson et al. |
| 10,548,913 B2 | 2/2020 | Normington et al. |
| 10,603,334 B2 | 3/2020 | Wu et al. |
| 10,689,411 B2 | 6/2020 | Migaud et al. |
| 10,934,322 B2 | 3/2021 | Migaud et al. |
| 11,242,364 B1 | 2/2022 | Migaud et al. |
| 11,274,117 B2 | 3/2022 | Migaud et al. |
| 11,584,771 B2 | 2/2023 | Schabert et al. |
| 12,043,616 B2 | 7/2024 | Marcotulli et al. |
| 2015/0265642 A1 | 9/2015 | Sinclair et al. |
| 2016/0279161 A1 | 9/2016 | Wu et al. |
| 2017/0121746 A1 | 5/2017 | Velasquez et al. |
| 2017/0252362 A1 | 9/2017 | Vannini et al. |
| 2017/0312300 A1 | 11/2017 | Djouder et al. |
| 2018/0051253 A1 | 2/2018 | Chen |
| 2018/0118819 A1 | 5/2018 | Sinclair et al. |
| 2018/0134743 A1 | 5/2018 | Migaud et al. |
| 2018/0163243 A1 | 6/2018 | Wu et al. |
| 2018/0258127 A1 | 9/2018 | Migaud et al. |
| 2020/0046741 A1 | 2/2020 | Sinclair et al. |

(Continued)

FOREIGN PATENT DOCUMENTS

| | | |
|---|---|---|
| CN | 108774278 A | 11/2018 |
| EP | 3063163 A1 | 9/2016 |

(Continued)

OTHER PUBLICATIONS

Schabert, Molecules 2021, 26, 2279. (Year: 2021).*
Bastin, Richard J., et al., Salt Selection and Optimisation Procedures for Pharmaceutical New Chemical Entities. Organic Process Research and Development 4(5):427-435 (2000).
Bernstein, J. Polymorphism in molecular crystals. Moscow, Science, 2007, chapter 7.3.2. Bioavailability, p. 324-330. With English machine translation.
Bernstein, J. Polymorphism in Molecular Crystals, pp. 243-249. Clarendon Press, Oxford (2002).
Caira, Mino R. Crystalline Polymorphism of Organic Compounds. In: Design of Organic Solids, Topics in Current Chemistry. Springer 198:163-208 (1998).
Conze et al. Safety and Metabolism of Long-term Administration of NIAGEN (Nicotinamide Riboside Chloride)in a Randomized, Double-Blind, Placebo-controlled Clinical Trial of Healthy Overweight Adults. Scientific Reports 9:9772 (pp. 1-13) (2019).

(Continued)

*Primary Examiner* — Layla D Berry
(74) *Attorney, Agent, or Firm* — Wilson Sonsini Goodrich & Rosati

(57) ABSTRACT

The present invention relates to a method of making nicotinamide ribofuranosie salts, in particular pharmaceutically acceptable nicotinamide ribofuranoside salts. The invention further relates to the nicotinamide ribofuranoside salts as such, in particular carboxylic acid salts in crystalline form, and their use in nutritional supplements and pharmaceutical compositions.

21 Claims, 9 Drawing Sheets

(56) References Cited

U.S. PATENT DOCUMENTS

| | | |
|---|---|---|
| 2020/0069711 A1 | 3/2020 | Marcotulli et al. |
| 2022/0135610 A1 | 5/2022 | Schabert et al. |
| 2022/0251133 A1 | 8/2022 | Schabert et al. |
| 2023/0348521 A1 | 11/2023 | Marcotulli et al. |
| 2024/0059727 A1 | 2/2024 | Spitz et al. |

FOREIGN PATENT DOCUMENTS

| | | |
|---|---|---|
| EP | 3149016 A1 | 4/2017 |
| EP | 3429354 A1 | 1/2019 |
| EP | 3538099 A1 | 9/2019 |
| EP | 3063163 B1 | 8/2022 |
| WO | WO-2010010454 A2 | 1/2010 |
| WO | WO-2010083414 A1 | 7/2010 |
| WO | WO-2015066382 A1 | 5/2015 |
| WO | WO-2015186068 A1 | 12/2015 |
| WO | WO-2016014927 A2 | 1/2016 |
| WO | WO-2016149395 A1 | 9/2016 |
| WO | WO-2017161165 A1 | 9/2017 |
| WO | WO-2017218580 A1 | 12/2017 |
| WO | WO-2018089830 A1 | 5/2018 |
| WO | WO-2019219895 A1 | 11/2019 |
| WO | WO-2021013795 A2 | 1/2021 |
| WO | WO-2021013795 A3 | 3/2021 |

OTHER PUBLICATIONS

Gupta, Deepak, et al., Salts of Therapeutic Agents: Chemical, Physicochemical, and Biological Considerations. Molecules 23(7):1719 (2018).

Jarman et al. 4-Substituted Nicotinic Acids and Nicotinamides. Part II. The Preparation of 4-Methylnicotinamide Riboside. J Chem Soc (C), pp. 199-203 (1969).

Kummerer, Klaus, Pharmaceuticals in the environment. Annual review of environment and resources 35:57-75 (2010).

Kuznetsova, G.A., Methodical Recommendations, Irkutsk State University, Chapter General Physics, 28 pages (2005). With English machine translation.

Lee et al. A chemical synthesis of nicotinamide adenine dinucleotide (NAD+). Chem. Commun., 8:729-730 (1999).

Makarov et al. Syntheses and chemical properties of β-nicotinamide riboside and its analogues and derivatives. Beilstein J. Org. Chem. 15:401-430 (2019).

Morissette, Sherry L. et al. High-throughput Crystallization: Polymorphs, Salts, Co-crystals and Solvates of Pharmaceutical Solids. Advanced Drug Delivery Reviews 56(3):275-300 (2004).

Newman. Specialized Solid Form Screening Techniques. Org Process Res Dev 17:457-471 (Oct. 30, 2012). Special Issue: Polymorphism and Crystallization 2013.

Patel, Viralkumar et al. Intestinal and renal effects of low-vol. phosphate and sulfate cathartic solutions designed for cleansing the colon: pathophysiological studies in five normal subjects. Am J Gastroenterol 104(4):953-965 (2009).

PCT/EP2020/070451 International Preliminary Report on Patentability dated Jan. 25, 2022.

PCT/EP2020/070451 International Search Report and Written Opinion dated Jan. 18, 2021.

Rodriguez-Spong, Barbara, et al., General principles of pharmaceutical solid polymorphism: a supramolecular perspective. Advanced Drug Delivery Reviews 56:241-274 (2004).

Tanimori et al. An efficient chemical synthesis of nicotinamide riboside (NAR) and analogues. Bioorganic & Medicinal Chemistry Letters 12:1135-1137 (2002).

Tyurina, L.E., et al., Food Additives. Ministry of Agriculture of the Russian Federation Krasnoyarsk State Agrarian University, Krasnoyarsk, 7 pages (2008). With English machine translation.

U.S. Appl. No. 17/576,699 Office Action dated Jul. 30, 2024.

Variankaval, Narayan, et al., From form to function: Crystallization of active pharmaceutical ingredients. AIChE Journal 54(7):1682-1688 (2008).

Yang et al. Syntheses of nicotinamide riboside and derivatives: effective agents for increasing nicotinamide adenine dinucleotide concentrations in mammalian cells. J. Med. Chem. 50:6458-61 (2007).

* cited by examiner

METHOD OF MAKING NICOTINAMIDE RIBOFURANOSIDE SALTS, NICOTINAMIDE RIBOFURANOSIDE SALTS AS SUCH, AND USES THEREOF

CROSS-REFERENCE

This application is a continuation of U.S. application Ser. No. 17/576,699, filed Jan. 14, 2022, which is a continuation of International Application No. PCT/EP2020/070451, filed Jul. 20, 2020, which claims the benefit of EP19187314.0 filed on Jul. 19, 2019 and EP19206542.3 filed on Oct. 31, 2019, each of which is entirely incorporated herein by reference.

FIELD OF THE INVENTION

The present invention relates to a method of making nicotinamide ribofuranoside salts, in particular pharmaceutically acceptable nicotinamide ribofuranoside salts. The invention further relates to nicotinamide ribofuranoside salts as such, in particular carboxylic acid salts in crystalline form, and their use in nutritional supplements and pharmaceutical compositions.

BACKGROUND OF THE INVENTION

Nicotinamide riboside (nicotinamide-β-D-ribofuranoside; CAS no 1341-23-7)

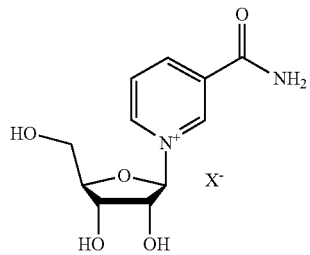

is a precursor of nicotinamide adenine dinucleotide ($NAD^+$/NADH) and nicotinamide adenine dinucleotide phosphate ($NADP^+$/NADPH). In addition, nicotinamide riboside is a niacin (vitamin B3) equivalent.

Nicotinamide riboside has been reported to increase $NAD^+$ levels in liver and skeletal muscle and to prevent body weight gain in mice fed a high-fat diet. It also increases $NAD^+$ concentration in the cerebral cortex and reduces cognitive deterioration in a transgenic mouse model of Alzheimer's disease. For these reasons, nicotinamide riboside salts have been suggested for use in nutritional supplements and pharmaceutical compositions. In fact, the chloride salt of nicotinamide-β-D-ribofuranoside is a commercially available nutritional supplement.

However, broad application of these compounds as dietary supplements has been limited by production methods which are low in yield, have poor stereoselectivity, and/or employ expensive and/or hazardous reagents, or which lead to pyridinium salts comprising pharmaceutically unsuitable counter-ions. Therefore, many known synthetic methods are not amenable to large-scale, commercial syntheses.

WO 2016/014927 discloses a crystalline form of nicotinamide riboside chloride which is described to have advantageous properties, e.g. ease in purification, relative to amorphous forms of nicotinamide riboside salts.

WO 2017/218580 discloses synthetic methods for the preparation of nicotinamide riboside salts including salts comprising a pharmaceutically acceptable anion. The methods may include converting one pharmaceutically acceptable counter-ion of the nicotinamide-β-D-ribofuranoside moiety to another pharmaceutically acceptable counter-ion through ion exchange chromatography or salt exchange reaction and precipitation. In certain embodiments, the described methods include converting a salt of nicotinamide riboside or analogs thereof, where the salt is not the chloride salt, to the corresponding chloride salt.

WO 2015/186068 A1 discloses the reaction of nicotinamide-β-D-ribofuranoside triflate with sodium methylate in an ion exchange reaction to afford crystalline nicotinamide-β-D-riboside chloride.

CN 108774278 discloses the reaction of nicotinamide triacetylribofuranoside triflate with a base in order to deacetylate the furanoside. Subsequently, the deacetylated product is treated with an acid to give the corresponding salt product.

However, for given applications, alternative pharmaceutically acceptable salts of nicotinamide riboside are desirable as well as methods that allow for their preparation in an inexpensive, efficient and convenient way.

OBJECTS OF THE INVENTION

Accordingly, there is a need in the art for pharmaceutically acceptable nicotinamide ribofuranoside salts, preferably crystalline salts, and methods for making pharmaceutically acceptable nicotinamide ribofuranoside salts in high purity and yield at low costs and on an industrial scale.

SUMMARY OF THE INVENTION

This object was achieved with a method using nicotinamide-β-D-ribofuranoside bromide or nicotinamide-β-D-ribofuranoside trifluoromethanesulfonate as starting material for making nicotinamide-β-D-ribofuranoside salts other than the bromide and triflate salts via salt metathesis comprising counter-ion exchange.

Nicotinamide-β-D-ribofuranoside nonafluorobutanesulfonate, nicotinamide-β-D-ribofuranoside fluorosulfonate or nicotinamide-β-D-ribofuranoside perchlorate are other suitable starting materials in the methods according to the invention.

In yet another embodiment, nicotinamide-β-D-ribofuranoside chloride or iodide are used as starting materials in the methods according to the invention.

In one embodiment, the use of nicotinamide-β-D-ribofuranoside bromide and nicotinamide-β-D-ribofuranoside trifluoromethanesulfonate and in particular nicotinamide-β-D-ribofuranoside iodide as starting material is preferred.

In a preferred embodiment, nicotinamide-β-D-ribofuranoside salts are available via the methods according to the invention, wherein the salts advantageously may be provided in crystalline form.

According to a first aspect, the invention relates to a method of making a nicotinamide-β-D-ribofuranoside salt, comprising step (A):

(A) subjecting nicotinamide-β-D-ribofuranoside bromide, nicotinamide-β-D-ribofuranoside chloride, nicotinamide-β-D-ribofuranoside iodide, nicotinamide-β-D-ribofuranoside trifluoromethanesulfonate, nicotinamide-β-D-ribofuranoside nonafluorobutanesulfonate, nicotinamide-β-D-ribofuranoside fluorosulfonate or nicotinamide-β-D-ribofuranoside perchlorate to salt metathesis comprising counter-ion exchange to afford the nicotinamide-β-D-ribofuranoside salt.

The nicotinamide-β-D-ribofuranoside salt to be made by the method is not a bromide, a iodide, a triflate, a nonaflate, a fluorosulfonate or a perchlorate.

According to a second aspect, the invention relates to a method of making a nicotinamide-β-D-ribofuranoside salt, comprising steps (A) and (B):

(A) subjecting nicotinamide-2,3,5-tri-O-acyl-β-D-ribofuranoside bromide, nicotinamide-2,3,5-tri-O-acyl-β-D-ribofuranoside chloride, nicotinamide-2,3,5-tri-O-acyl-β-D-ribofuranoside iodide, nicotinamide-2,3,5-tri-O-acyl-β-D-ribofuranoside trifluoromethanesulfonate, nicotinamide-2,3,5-tri-O-acyl-β-D-ribofuranoside nonafluorobutanesulfonate, nicotinamide-2,3,5-tri-O-acyl-β-D-ribofuranoside fluorosulfonate or nicotinamide-2,3,5-tri-O-acyl-β-D-ribofuranoside perchlorate to salt metathesis comprising counter-ion exchange to afford a nicotinamide-2,3,5-tri-O-acyl-β-D-ribofuranoside salt;

(B) deacylating the nicotinamide-2,3,5-tri-O-acyl-β-D-ribofuranoside salt to afford the nicotinamide-β-D-ribofuranoside salt.

The nicotinamide-β-D-ribofuranoside salt to be made by the method is not a bromide, a iodide, a triflate, a nonaflate, a fluorosulfonate or a perchlorate.

According to a third aspect, the invention relates to a method of making a nicotinamide-2,3,5-tri-O-acyl-β-D-ribofuranoside salt from nicotinamide-2,3,5-tri-O-acyl-β-D-ribofuranoside bromide, nicotinamide-2,3,5-tri-O-acyl-β-D-ribofuranoside chloride, nicotinamide-2,3,5-tri-O-acyl-β-D-ribofuranoside iodide, nicotinamide-2,3,5-tri-O-acyl-β-D-ribofuranoside trifluoromethanesulfonate, nicotinamide-2,3,5-tri-O-acyl-β-D-ribofuranoside nonafluorobutanesulfonate nicotinamide-2,3,5-tri-O-acyl-β-D-ribofuranoside fluorosulfonate or nicotinamide-2,3,5-tri-O-acyl-β-D-ribofuranoside perchlorate, comprising step (A):

(A) subjecting nicotinamide-2,3,5-tri-O-acyl-β-D-ribofuranoside bromide, nicotinamide-2,3,5-tri-O-acyl-β-D-ribofuranoside chloride, nicotinamide-2,3,5-tri-O-acyl-β-D-ribofuranoside iodide, nicotinamide-2,3,5-tri-O-acyl-β-D-ribofuranoside trifluoromethanesulfonate, nicotinamide-2,3,5-tri-O-acyl-β-D-ribofuranoside nonafluorobutanesulfonate, nicotinamide-2,3,5-tri-O-acyl-β-D-ribofuranoside fluorosulfonate or nicotinamide-2,3,5-tri-O-acyl-β-D-ribofuranoside perchlorate to salt metathesis comprising counter-ion exchange to afford the nicotinamide-2,3,5-tri-O-acyl-β-D-ribofuranoside salt.

The nicotinamide-2,3,5-tri-O-acyl-β-D-ribofuranoside salt to be made by the method is not a bromide, a iodide, a triflate, a nonaflate, a fluorosulfonate or a perchlorate.

According to a fourth aspect, the invention relates to crystalline nicotinamide-β-D-ribofuranoside D-, L- or DL-hydrogen malate; or crystalline nicotinamide-β-D-ribofuranoside D-, L- or DL-hydrogen tartrate; being characterized by a powder X-ray diffraction pattern, respectively.

Nicotinamide-β-D-ribofuranoside salts prepared according to the methods of the invention are frequently obtained in amorphous form and have to be subsequently crystallized, if desired, and if possible at all.

However, the addressed D-, L- or DL-hydrogen malates and D-, L- or DL-hydrogen tartrates surprisingly may be obtained directly via salt metathesis in crystalline form in high purity and excellent yield. This is extraordinarily advantageous e.g. in view of application and further processing. Therefore, it is suggested to use these salts in or as a nutritional supplement. Furthermore, said salts may serve as starting material for making further nicotinamide-β-D-ribofuranoside salts or related compounds.

According to a fifth aspect, the invention relates to a nutritional supplement comprising a nicotinamide-β-D-ribofuranoside salt obtained according to a method as defined in the first or second aspect or comprising a nicotinamide-β-D-ribofuranoside salt as defined in the fourth aspect.

According to a sixth aspect, the invention relates to a pharmaceutical composition comprising a nicotinamide-β-D-ribofuranoside salt obtained according to a method as defined in the first or second aspect or comprising a nicotinamide-β-D-ribofuranoside salt as defined in the fourth aspect.

According to a seventh aspect, the invention relates to a method of performing a chemical synthesis, comprising step (A):

(A) providing a nicotinamide-β-D-ribofuranoside salt obtained by the method as defined in the first or second aspect, or providing a compound defined in the fourth aspect.

According to an eighth aspect, the invention relates to a method of making nicotinamide-2,3,5-tri-O-acyl-β-D-ribofuranoside triflate or iodide, the method comprising step (A):

(A) reacting tetra-O-acyl-β-D-ribofuranose of formula

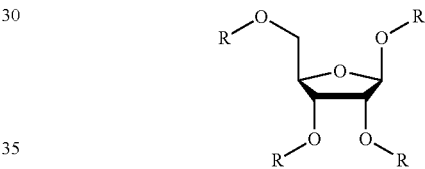

wherein each R is independently selected from alkyl carbonyl, aryl carbonyl and heteroaryl carbonyl, preferably from $C_{1-10}$ alkyl carbonyl and benzoyl, and is more preferably acetyl, and wherein R is optionally independently substituted with one or more substituents selected from: $C_{1-6}$ alkyl, $C_{1-6}$ alkoxy, $C_{1-6}$ thioalkyl, halogen, nitro, cyano, $NH(C_{1-6}$ alkyl), $N(C_{1-6}$ alkyl$)_2$, and $SO_2N(C_{1-6}$ alkyl$)_2$, with nicotinamide of formula

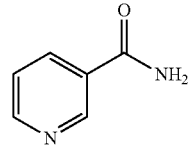

in presence of 0.9 to 1.5 mole equivalent trimethylsilyl triflate or iodide related to one mole of tetra-O-acyl-β-D-ribofuranose.

In a ninth aspect, the invention relates to a compound selected from nicotinamide-2,3,5-tri-O-acyl-β-D-ribofuranoside nonafluorobutanesulfonate, nicotinamide-β-D-ribofuranoside nonafluorobutanesulfonate, nicotinamide-2,3,5-tri-O-acyl-β-D-ribofuranoside perchlorate, and nicotinamide-β-D-ribofuranoside perchlorate, nicotinamide-2,3,5-tri-O-acyl-β-D-ribofuranoside iodide, nicotinamide-β-D-ribofuranoside iodide, nicotinamide-2,3,5-tri-O- acyl-β-D-ribofuranoside fluorosulfonate, and nicotinamide-β-D-ribofuranoside fluorosulfonate.

BRIEF DESCRIPTION OF THE FIGURES

The present invention is further described by the appended figures, in which.

Figure 1:
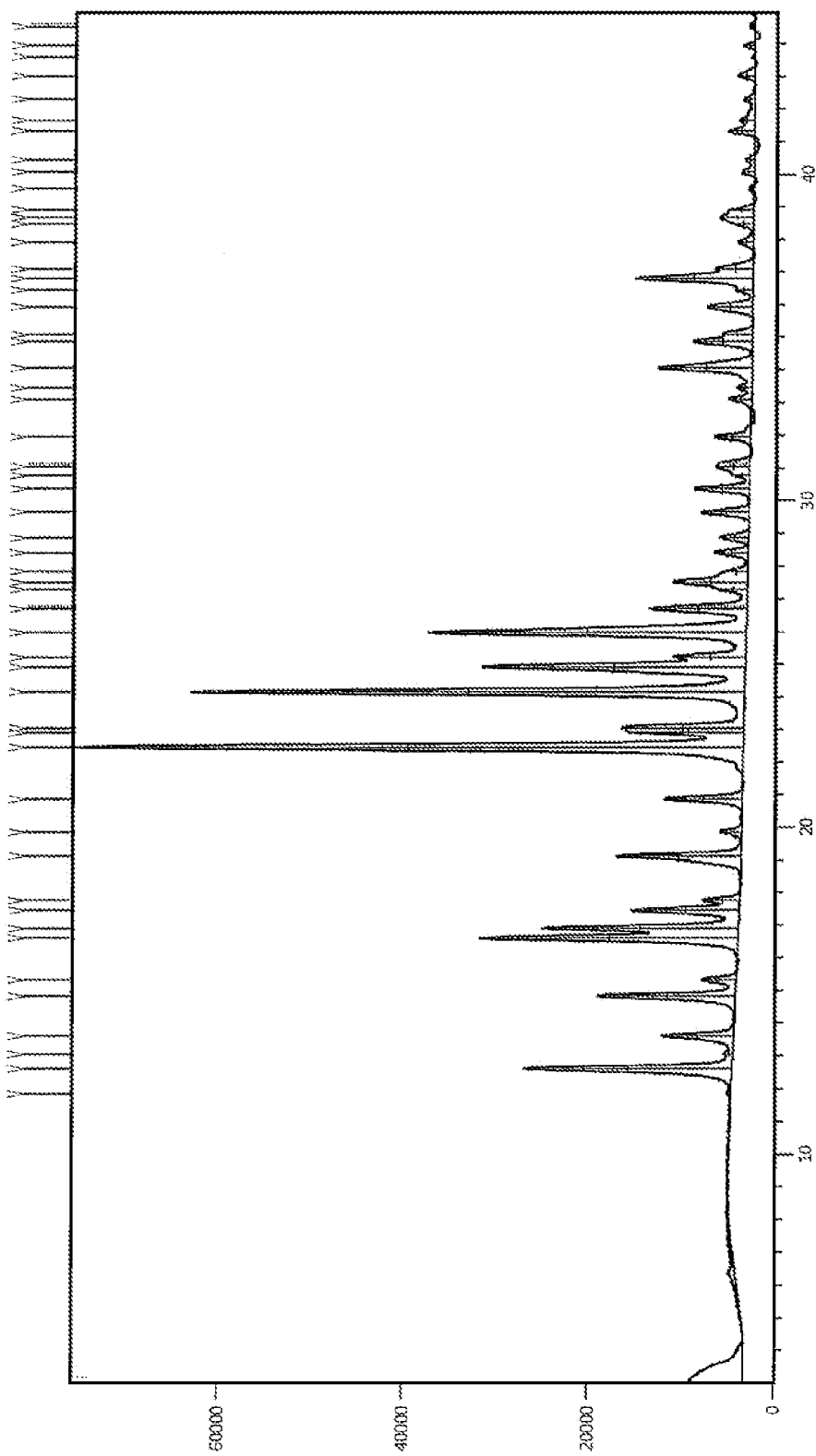
FIG. 1 shows a powder X-ray pattern of crystalline nicotinamide-β-D-ribofuranoside D-hydrogen malate.

{x-axis: Position [°2Theta] (Copper(Cu); y-axis: Counts), respectively}.

DETAILED DESCRIPTION OF THE INVENTION

The various aspects of the present invention will now be described in more detail with reference to the figures.

First, Second and Third Aspect: Methods According to the Invention

According to a first aspect, the invention relates to a method of replacing the anion $X^- = Br^-, Cl^-, I^-, CF_3SO_3^-$ (triflate), $n\text{-}C_4F_9SO_3^-$ (nonaflate), $FSO_3^-$ or $ClO_4^-$ in a compound of formula

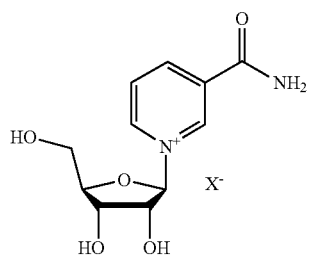

by an anion $Y^-$ via salt metathesis comprising counter-ion exchange.

Accordingly, in the first aspect, the invention relates to a method of making a nicotinamide-β-D-ribofuranoside salt, comprising step (A):

(A) subjecting nicotinamide-β-D-ribofuranoside bromide, chloride, iodide, triflate, nonaflate, fluorosulfonate or perchlorate to salt metathesis comprising counter-ion exchange to afford the nicotinamide-β-D-ribofuranoside salt.

In an alternative embodiment, according to a second aspect, a nicotinamide-2,3,5-tri-O-acyl-β-D-ribofuranoside bromide, chloride, iodide, triflate, nonaflate, fluorosulfonate or perchlorate of formula

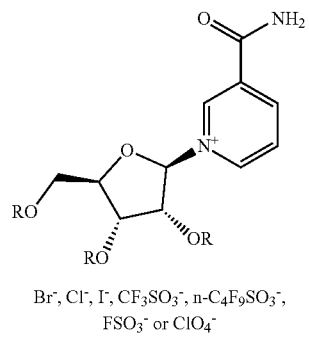

$Br^-, Cl^-, I^-, CF_3SO_3^-, n\text{-}C_4F_9SO_3^-,$
$FSO_3^-$ or $ClO_4^-$ is subjected to salt metathesis in order to exchange $Br^-$, $Cl^-, I^-, CF_3SO_3^-, n\text{-}C_4F_9SO_3^-$ $FSO_3^-$ or $ClO_4^-$ through an anion $Y^-$. Subsequently, the acyl groups are cleaved in order to afford the desired nicotinamide-β-D-ribofuranoside salt.

Accordingly, in the second aspect, the invention relates to a method of making a nicotinamide-β-D-ribofuranoside salt, comprising steps (A) and (B):

(A) subjecting nicotinamide-2,3,5-tri-O-acyl-β-D-ribofuranoside bromide, chloride, iodide, triflate, nonaflate, fluorosulfonate or perchlorate to salt metathesis comprising counter-ion exchange to afford a nicotinamide-2,3,5-tri-O-acyl-β-D-ribofuranoside salt; and (B) deacylating the nicotinamide-2,3,5-tri-O-acyl-β-D-ribofuranoside salt to afford the nicotinamide-β-D-ribofuranoside salt.

If desired, the nicotinamide-2,3,5-tri-O-acyl-β-D-ribofuranoside salt obtained in step (A) may be used for purposes different from step (B).

Accordingly, in a third aspect, the invention relates to a method of making a nicotinamide-2,3,5-tri-O-acyl-β-D-ribofuranoside salt, comprising step (A):

(A) subjecting a nicotinamide-2,3,5-tri-O-acyl-β-D-ribofuranoside bromide, chloride, iodide, triflate, nonaflate, fluorosulfonate or perchlorate to salt metathesis comprising counter-ion exchange to afford the nicotinamide-2,3,5-tri-O-acyl-β-D-ribofuranoside salt.

Nicotinamide-β-D-ribofuranoside bromide [N1-(β-D-Ribofuranosyl)-3-aminocarbonylpyridinium bromide)

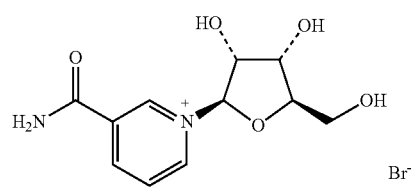

as used in step (A) of the method defined in the first aspect is a well-known compound (CAS no 78687-39-5). E.g., Lee et al. disclose a chemical synthesis method thereof (Chem. Commun., 1999, 729-730). A further synthesis method is disclosed in EP 18173208.2 not yet published at the filing date of this application.

Said references also disclose the preparation of nicotinamide-2,3,5-tri-O-acyl-β-D-ribofuranoside bromide as a precursor of nicotinamide-β-D-ribofuranoside bromide.

Nicotinamide-β-D-ribofuranoside triflate [N1-(β-D-Ribofuranosyl)-3-aminocarbonylpyridinium triflate]

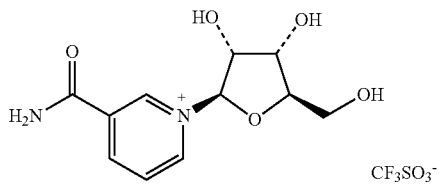

is also a well-known compound (CAS no 445489-49-6).

Nicotinamide-β-D-ribofuranoside triflate and nicotinamide-2,3,5-tri-O-acyl-β-D-ribofuranoside triflate may be prepared e.g. by reacting nicotinamide with a tetra-O-acyl-β-D-ribofuranose in acetonitrile in the presence of trimethylsilyl trifluoromethanesulfonate (TMSOTf) to afford a nicotinamide-2,3,5-tri-O-acyl-β-D-ribofuranoside triflate. The acyl groups may then be cleaved according to known methods to afford the nicotinamide-β-D-ribofuranoside triflate (e.g. Makarova et al.: "Syntheses and chemical properties of β-nicotinamide riboside and its analogues and derivatives", Beilstein J Org Chem 2019, 15:401-430; Tanimori et al., "An Efficient Chemical Synthesis of Nicotinamide Riboside (NAR) and Analogues", Bioorganic & Medicinal Chemistry Letters 12 (2002) 1135-1137).

Nicotinamide-β-D-ribofuranoside nonaflate and nicotinamide-2,3,5-tri-O-acyl-β-D-ribofuranoside nonaflate, respectively nicotinamide-β-D-ribofuranoside perchlorate and nicotinamide-2,3,5-tri-O-acyl-β-D-ribofuranoside perchlorate, may be prepared by reacting nicotinamide with a tetra-O-acyl-β-D-ribofuranose in a solvent such as acetonitrile in the presence of trimethylsilyl nonafluorobutanesulfonate (CAS no 68734-62-3), respectively trimethylsilyl perchlorate (CAS no 18204-79-0) to afford a nicotinamide-2,3,5-tri-O-acyl-β-D-ribofuranoside nonaflate, respectively perchlorate. The acyl groups may then be cleaved according to known methods to afford the nicotinamide-β-D-ribofuranoside nonaflate, respectively perchlorate.

Nicotinamide-β-D-ribofuranoside chloride and nicotinamide-2,3,5-tri-O-acyl-β-D-ribofuranoside chloride, nicotinamide-β-D-ribofuranoside iodide and nicotinamide-2,3,5-tri-O-acyl-β-D-ribofuranoside iodide, respectively nicotinamide-β-D-ribofuranoside fluorosulfonate and nicotinamide-2,3,5-tri-O-acyl-β-D-ribofuranoside sulfonate, may be prepared by reacting nicotinamide with a tetra-O-acyl-β-D-ribofuranose in a solvent such as acetonitrile in the presence of trimethylsilyl chloride (CAS no 75-77-4), trimethylsilyl iodide (CAS no. 16029-98-4), respectively trimethylsilyl fluorosulfonate (CAS no 3167-56-4) to afford a nicotinamide-2,3,5-tri-O-acyl-β-D-ribofuranoside chloride, iodide, respectively fluorosulfonate. The acyl groups may then be cleaved according to known methods to afford the nicotinamide-β-D-ribofuranoside chloride, iodide, respectively fluorosulfonate.

The term "salt metathesis" as used in this disclosure is synonymously used with terms such as "double replacement reaction", "double displacement reaction" or "double decomposition reaction". Salt metathesis for exchanging counter-ions between two different salts is a known technique.

Thus, step (A) defines a reaction, wherein a first salt, e.g. a nicotinamide-β-D-ribofuranoside salt $NR^+Br^-$ (or a nicotinamide-2,3,5-tri-O-acyl-β-D-ribofuranoside salt $AcONR^+Br^-$) is subjected to a salt metathesis using a suitable second salt comprising a cation $Cat^+$ and an anion $Y^-$ to afford a nicotinamide-β-D-ribofuranoside salt $NR^+Y^-$ (or $AcONR^+Y^-$) and $Cat^+Br^-$ via counter-ion exchange, i.e. exchange of $Br^-$ in $NR^+Br^-$ (or $AcONR^+Br^-$) by $Y^-$. This reaction is summarized by the following equation:

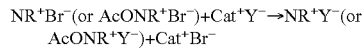

The driving force of a salt metathesis reaction such as in the above equation may be the formation of more stable salts as well as the removal of a product from the chemical equilibrium of the reaction, e.g. by precipitation of one of the formed $NR^+Y^-$ ($AcONR^+Y^-$) or $Cat^+Br^-$. Thus, in order to drive the reaction to the products, the educts have to be selected in view of solubility in one another or in a solvent, respectively in view of favorable energies.

An analogous mechanism applies to the reaction of the chloride, iodide, triflate, nonaflate, fluorosulfonate and perchlorate.

If the salt metathesis reaction is performed in a solvent, the influence of same on the reaction will be explained in more detail hereinunder in the respective section Solvent.

The term "salt metathesis" as used herein does not mean that the anion of the β-nicotinamide riboside is exchanged by another anion by means of ion exchange using an ion exchanger. Thus, the method defined in step (A) excludes an anion exchange by means of an ion exchanger.

However, the method does not exclude that in any reaction step prior to step (A) or subsequently to step (A) an ion exchanger may be used.

Nicotinamide-2,3,5-tri-O-acyl-β-D-ribofuranoside bromides, nicotinamide-2,3,5-tri-O-acyl-β-D-ribofuranoside chlorides, nicotinamide-2,3,5-tri-O-acyl-β-D-ribofuranoside iodides, nicotinamide-2,3,5-tri-O-acyl-β-D-ribofuranoside trifluoromethanesulfonates, nicotinamide-2,3,5-tri-O-acyl-β-D-ribofuranoside nonafluorobutanesulfonates, nicotinamide-2,3,5-tri-O-acyl-β-D-ribofuranoside fluorosulfonates or nicotinamide-2,3,5-tri-O-acyl-β-D-ribofuranoside perchlorates as used in step (B) of the method according to the second aspect are either known or can be prepared according to known methods.

The term "acyl" as used in connection with nicotinamide-2,3,5-tri-O-acyl-β-D-ribofuranoside salts, i.e. the bromide, chloride, iodide, triflate, nonaflate, fluorosulfonate or perchlorate, means that acyl is independently selected from alkyl carbonyl, aryl carbonyl and heteroaryl carbonyl, preferably from $C_{1-10}$ alkyl carbonyl and benzoyl, and is more preferably acetyl, and wherein R is optionally independently substituted with one or more substituents selected from: $C_{1-6}$ alkyl, $C_{1-6}$ alkoxy, $C_{1-6}$ thioalkyl, halogen, nitro, cyano, $NH(C_{1-6}$ alkyl), $N(C_{1-6}$ alkyl$)_2$, and $SO_2N(C_{1-6}$ alkyl$)_2$.

In one embodiment, the nicotinamide-2,3,5-tri-O-acyl-β-D-ribofuranoside salt obtained in step (A) may be isolated and purified before it is deacylated in step (B).

In another embodiment, the nicotinamide-2,3,5-tri-O-acyl-β-D-ribofuranoside salt is not purified prior to deacylation in step (B).

Deacylation (deprotection) according to step (B) may be performed according to methods known in the art, e.g. by subjecting the salt obtained in step (A) to an acid such as hydrogen bromide, hydrogen chloride, hydrogen iodide or sulfuric acid, or to a base such as ammonia.

Preferred Embodiments According to the First, Second and Third Aspect: Nicotinamide-β-D-ribofuranoside Bromide, Chloride, Iodide, Triflate, Nonaflate, Fluorosulfonate or Perchlorate or nicotinamide-2,3,5-tri-O-acyl-β-D-ribofuranoside Bromide, Chloride, Iodide, Triflate, Nonaflate, Fluorosulfonate or Perchlorate Used in Step (A) as Starting Materials According to the invention, the nicotinamide-β-D-ribofuranoside salt or nicotinamide-2,3,5-tri-O-acyl-β-D-ribofuranoside salt used in step (A) is the bromide, the chloride, the iodide, the triflate, the nonaflate, the fluorosulfonate or the perchlorate. The bromides and triflates are well amenable compounds and have therefore been used in the art as starting material for numerous subsequent process steps.

Furthermore, at least nicotinamide-β-D-ribofuranoside bromide or nicotinamide-2,3,5-tri-O-acyl-β-D-ribofuranoside bromide or nicotinamide-β-D-ribofuranoside chloride or nicotinamide-2,3,5-tri-O-acyl-β-D-ribofuranoside chloride may be provided in crystalline form which is favorable due to the purity thereof in view of making further crystalline nicotinamide-β-D-ribofuranoside salts.

In a preferred embodiment, a method of making a nicotinamide-β-D-ribofuranoside bromide or nicotinamide-2,3,5-tri-O-acyl-β-D-ribofuranoside bromide is used as disclosed in EP 18173208.2 (not yet published at the filing date of this application). This reference is incorporated herein in its entirety.

Accordingly, in one embodiment of the first aspect, the method according to the invention comprises prior to step (A) steps (X) and (Y) and step (Z):

(X) subjecting a tetra-O-acyl-β-D-ribofuranose of formula

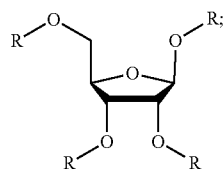

to hydrogen bromide in acetic acid to afford a tri-O-acyl-D-ribofuranoside bromide (in the form of a mixture of the β- and the α-anomer) of formula

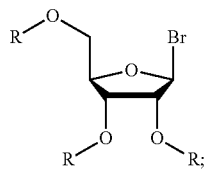

(Y) reacting the tri-O-acyl-D-ribofuranoside bromide with nicotinamide

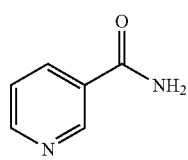

to afford a nicotinamide-2,3,5-tri-O-acyl-β-D-ribofuranoside bromide of formula

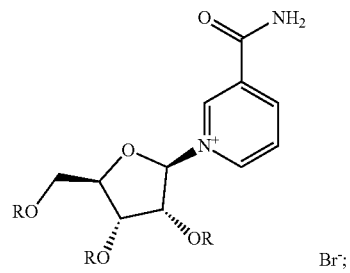

and (Z) deacylating the nicotinamide-2,3,5-tri-O-acyl-β-D-ribofuranoside obtained in step (Y) by removing the R groups using hydrogen bromide in acetic acid to afford the nicotinamide-β-D-ribofuranoside bromide compound of formula

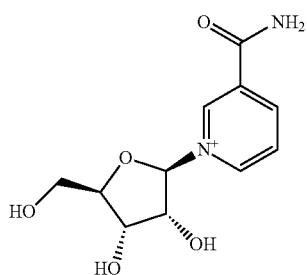

wherein the nicotinamide-β-D-ribofuranoside bromide obtained in step (Z) is used in step (A).

Basically, in other embodiments, acids different from HBr in acetic acid or bases such as ammonia may be used in the deacylation step (Z).

Nicotinamide-2,3,5-tri-O-acyl-β-D-ribofuranoside bromide obtained in step (Y) is typically obtained in mixture with the α-anomer. E.g., the molar ratio β:α may be about 85:15.

Accordingly, in one embodiment, if not purified at the stage of the mixture of β- and α-anomers, in subsequent steps, the educt is also provided as a mixture of β- and α-anomers. Purification may lead to the pure β-anomers.

In another embodiment, nicotinamide-2,3,5-tri-O-acyl-β-D-ribofuranoside bromide may be purified in order to result in the pure β-anomer before it is subjected to cleavage of the acyl groups.

According to another embodiment of the first aspect, the invention relates to a method comprising prior to step (A) steps (X) and (Y):

(X) subjecting a tetra-O-acyl-β-D-ribofuranose of formula

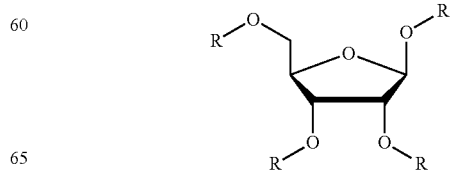

wherein each R is independently selected from alkyl carbonyl, aryl carbonyl and heteroaryl carbonyl, preferably from $C_{1-10}$ alkyl carbonyl and benzoyl, and is more preferably acetyl, and wherein R is optionally independently substituted with one or more substituents selected from: $C_{1-6}$ alkyl, $C_{1-6}$ alkoxy, $C_{1-6}$ thioalkyl, halogen, nitro, cyano, $NH(C_{1-6}$ alkyl), $N(C_{1-6}$ alkyl$)_2$, and $SO_2N(C_{1-6}$ alkyl$)_2$,
in the presence of trimethylsilyl chloride, trimethylsilyl bromide, trimethylsilyl iodide, trimethylsilyl triflate, trimethylsilyl nonaflate, trimethylsilyl fluorosulfonate or trimethylsilyl perchlorate to nicotinamide

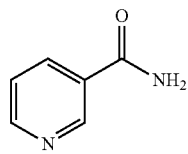

to afford the respective nicotinamide-2,3,5-tri-O-acyl-β-D-ribofuranoside chloride, bromide, iodide, triflate, nonaflate, fluorosulfonate or perchlorate of formula

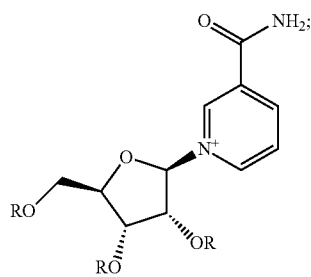

Cl⁻, Br⁻, I⁻, CF₃SO₃⁻, n-C₄F₉SO₃⁻, FSO₃⁻ or ClO₄⁻

(Y) deacylating the nicotinamide-2,3,5-tri-O-acyl-β-D-ribofuranoside chloride, bromide, iodide, triflate, nonaflate or perchlorate obtained in step (X) by removing the R groups to afford the nicotinamide-β-D-ribofuranoside chloride, bromide, iodide, triflate, nonaflate, fluorosulfonate or perchlorate compound of formula

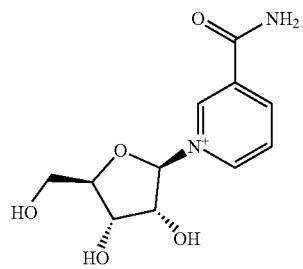

Cl⁻, Br⁻, I⁻, CF₃SO₃⁻, n-C₄F₉SO₃⁻, FSO₃⁻ or ClO₄⁻, wherein nicotinamide-β-D-ribofuranoside chloride, bromide, iodide, triflate, nonaflate, fluorosulfonate or perchlorate formed in step (Y) is used in step (A).

In one embodiment of the second aspect, the method according to the invention comprises prior to step (A) steps (X) and (Y):
(X) subjecting a tetra-O-acyl-β-D-ribofuranose of formula

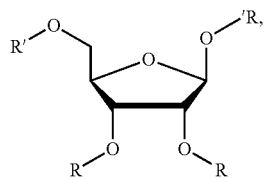

to hydrogen bromide in acetic acid to afford a tri-O-acyl-D-ribofuranoside bromide (in the form of a mixture of the β- and the α-anomer) of formula

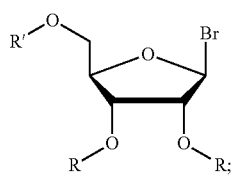

(Y) reacting the tri-O-acyl-D-ribofuranoside bromide with nicotinamide

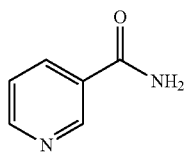

to afford a nicotinamide-2,3,5-tri-O-acyl-β-D-ribofuranoside bromide of formula

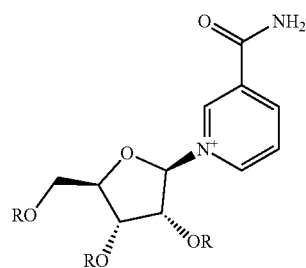

Br⁻;

wherein the nicotinamide-2,3,5-tri-O-acyl-β-D-ribofuranoside bromide obtained in step (Y) is used in step (A).

The product obtained in step (Y) may also be employed in the method defined in the third aspect.

R is an acyl group independently selected from alkyl carbonyl, aryl carbonyl and heteroaryl carbonyl, preferably from $C_{1-10}$ alkyl carbonyl and benzoyl, and is more preferably acetyl, and wherein R is optionally independently substituted with one or more substituents selected from: $C_{1-6}$ alkyl, $C_{1-6}$ alkoxy, $C_{1-6}$ thioalkyl, halogen, nitro, cyano, $NH(C_{1-6}$ alkyl), $N(C_{1-6}$ alkyl$)_2$, and $SO_2N(C_{1-6}$ alkyl$)_2$.

The term "acyl" as synonymously used with the term "acyl group" in nicotinamide-2,3,5-tri-O-acyl-β-D-ribofuranoside bromide means that the acyl group may be independently selected from alkyl carbonyl, aryl carbonyl or heteroaryl carbonyl.

The term "alkyl carbonyl" is synonymously used with the term "alkanoyl".

In one embodiment, R is independently selected from alkyl carbonyl, aryl carbonyl and heteroaryl carbonyl, preferably from $C_{1-10}$ alkyl carbonyl and benzoyl, and is preferably acetyl.

In one embodiment, acyl may be substituted.

In one embodiment, acyl may be independently substituted with one or more of the following substituents: $C_{1-6}$ alkyl, $C_{1-6}$ alkoxy, $C_{1-6}$ thioalkyl, halogen, nitro, cyano, $NH(C_{1-6}$ alkyl), $N(C_{1-6}$ alkyl)$_2$, and $SO_2N(C_{1-6}$ alkyl)$_2$.

In one embodiment, acyl is $C_{1-6}$ alkanoyl such as formyl, acetyl, propionyl, butyryl, valeryl or cyclohexyl, optionally substituted with one or more of the substituents mentioned above.

In another embodiment, acyl is benzoyl or naphthoyl, preferably benzoyl, optionally substituted with one or more of the substituents mentioned above.

Tetra-O-acyl-β-D-ribofuranoses are either known compounds or may be prepared according to known methods.

In a preferred embodiment, commercially available tetra-O-acetyl-β-D-ribofuranose (CAS Number 13035-61-5)

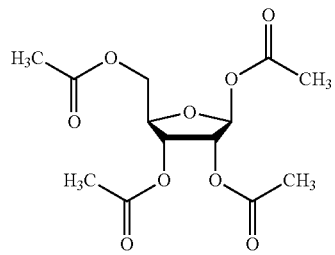

is used in step (X) to afford 2,3,5-tri-O-acyl-D-ribofuranoside bromide.

Nicotinamide-2,3,5-tri-O-acyl-β-D-ribofuranoside bromide obtained in step (Y) is typically produced as a mixture of anomers such as a mixture of anomers β and α, such as β:α in a ratio of from about 5:1 to 6:1.

In one embodiment, the crude nicotinamide-2,3,5-tri-O-acyl-β-D-ribofuranoside bromide can be employed in step (A) of the method according to the second aspect, i.e. it may be subjected to salt metathesis. Subsequently the formed salt is deacylated according to step (B) to afford the desired nicotinamide-β-D-ribofuranoside salt.

In another embodiment, the crude nicotinamide-2,3,5-tri-O-acyl-β-D-ribofuranoside bromide may be employed in step (Z) resulting in nicotinamide-β-D-ribofuranoside bromide via deacylation. Nicotinamide-β-D-ribofuranoside bromide may then be used in step (A) of the method according to the first aspect to afford the desired nicotinamide-β-D-ribofuranoside salt via salt metathesis.

In still another embodiment, it may be advantageous to purify and crystallize the crude nicotinamide-2,3,5-tri-O-acyl-β-D-ribofuranoside bromide obtained in step (Y) prior to step (Z). Using a purified and crystallized nicotinamide-2,3,5-tri-O-acyl-β-D-ribofuranoside bromide in the deacylation (deprotecting) step according to step (Z) may improve the tendency of nicotinamide-β-D-ribofuranoside bromide to result in a crystallized and thus in a substantially pure form.

Preferably, nicotinamide-2,3,5-tri-O-acyl-β-D-ribofuranoside bromide obtained in step (Y) may be re-crystallized from acetone. The pure β-anomer is obtained.

Accordingly, in one embodiment, the method further comprises step (Y1):

(Y1) purifying the product obtained in step (Y).

Preferably, purification according to step (Y1) is crystallization or re-crystallization.

The yield over steps (X), (Y) and (Y1) is typically in the range of from 40 to 50%.

In one embodiment, the purified nicotinamide-2,3,5-tri-O-acyl-β-D-ribofuranoside bromide may be used in step (A) as defined in the second aspect, i.e. it may be subjected to salt metathesis. Subsequently the formed salt is deacylated according to step (B) to afford the desired nicotinamide-β-D-ribofuranoside salt.

In another embodiment, the purified nicotinamide-2,3,5-tri-O-acyl-β-D-ribofuranoside bromide may be deacylated resulting in nicotinamide-β-D-ribofuranoside bromide which may be used in step (A) of the method according to the first aspect to afford the desired nicotinamide-β-D-ribofuranoside salt via salt metathesis.

If step (A) as defined in the first aspect is to be carried out, the acyl groups in nicotinamide-2,3,5-tri-O-acyl-β-D-ribofuranoside bromide obtained in step (Y) or (Y1) have to be cleaved, i.e. the protected hydroxyl groups are deprotected.

Basically any method known in the art may be used to remove the acyl groups from the protected OH-groups. Cleavage may be advantageously performed with hydrogen bromide in acetic acid.

This reaction may be beneficially carried out also at a large scale.

Nicotinamide-β-D-ribofuranoside bromide frequently directly precipitates from the solution obtained in the deprotection step in the form of crystals.

Crystallized nicotinamide-β-D-ribofuranoside bromide may be obtained in a purity of more than 97%, i.e. nearly free from the α-anomer, and containing only minor amounts of nicotinamide which has been used for substituting bromide in tri-O-acyl-β-D-ribofuranoside bromide, respectively for neutralizing an excess of hydrogen bromide.

If further necessary, nicotinamide-β-D-ribofuranoside bromide may be further purified, preferably by re-crystallization. A suitable solvent is e.g. methanol.

In a preferred embodiment, the method further comprises step (Z1):

(Z1) purifying the product obtained in step (Z).

In a preferred embodiment, purification according to step (Z1) comprises or is crystallization or re-crystallization.

The yield over steps (Z) and (Z1) is typically in the range of from 60 to 70%.

Advantageously, other salts, preferably crystalline salts, in which the anion preferably is a pharmaceutically acceptable anion, may be prepared starting from the bromide or triflate via salt metathesis according to the methods of the invention.

Preferably, nicotinamide-β-D-ribofuranoside hydrogen malates and nicotinamide-β-D-ribofuranoside hydrogen tartrates, preferably in crystalline form, may be synthesized as well as the 2,3,5-O-triacyl compounds thereof.

In another embodiment of the second aspect, the invention relates to a method comprising prior to step (A) steps (X):

(X) subjecting a tetra-O-acyl-β-D-ribofuranose of formula

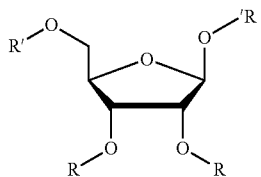

wherein each R is independently selected from alkyl carbonyl, aryl carbonyl and heteroaryl carbonyl, preferably from $C_{1-10}$ alkyl carbonyl and benzoyl, and is more preferably acetyl, and wherein R is optionally independently substituted with one or more substituents selected from: $C_{1-6}$ alkyl, $C_{1-6}$ alkoxy, $C_{1-6}$ thioalkyl, halogen, nitro, cyano, $NH(C_{1-6}$ alkyl), $N(C_{1-6}$ alkyl)$_2$, and $SO_2N(C_{1-6}$ alkyl)$_2$, in the presence of trimethylsilyl chloride, trimethylsilyl bromide, trimethylsilyl iodide, trimethylsilyl triflate, trimethylsilyl nonaflate, trimethylsilyl fluorosulfonate or trimethylsilyl perchlorate to nicotinamide

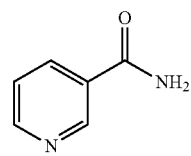

to afford a nicotinamide-2,3,5-tri-O-acyl-β-D-ribofuranoside chloride, bromide, iodide, triflate, nonaflate, fluorosulfonate or perchlorate of formula

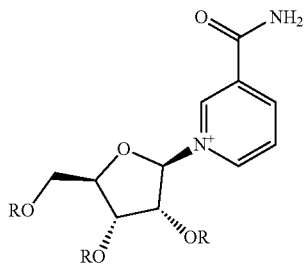

$Cl^-$, $Br^-$, $I^-$, $CF_3SO_3^-$, $n$-$C_4F_9SO_3^-$, $FSO_3^-$ or $ClO_4^-$, wherein nicotinamide-2,3,5-tri-O-acyl-β-D-ribofuranoside chloride, bromide, iodide, triflate, nonaflate, fluorosulfonate or perchlorate formed in step (X) is used in step (A).

Pharmaceutically Acceptable Ions

Preferably, the counter-ion $Y^-$ of the salt obtained in step (A) via counter-ion exchange originating from salt $Cat^+Y^-$ is a pharmaceutically acceptable ion.

The term "pharmaceutically acceptable ion" as used herein encompasses ions selected from the group consisting of
inorganic ions; or
carboxylates, wherein the carboxylic acid from which the carboxylate is derived, is optionally substituted with one or more substituents independently selected from the group consisting of carboxyl, hydroxyl, thio, keto, amino, mono $C_{1-6}$ alkyl, hydroxy $C_{1-6}$ alkylene and di($C_{1-6}$ alkyl) amino; or
$C_{1-12}$ alkyl sulfonates; or
arylsulfonates, wherein the aryl moiety is optionally substituted with one or more substituents independently selected from the group consisting of carboxyl, hydroxyl, amino, mono $C_{1-6}$ alkyl and di($C_{1-6}$ alkyl) amino, halogen, $C_{1-6}$ alkyl;
and wherein the pharmaceutically acceptable salt is not a bromide or a iodide or a triflate or a nonaflate or a fluorosulfonate or a perchlorate.

In a preferred embodiment, the
inorganic ion is selected from the group consisting of chloride, hydrogen sulfate, sulfate, dihydrogen phosphate, monohydrogen phosphate, phosphate, nitrate, hydrogen carbonate and carbonate;
carboxylate is selected from the group consisting of formate, acetate, oxalate, malonate, succinate, fumarate, maleate, citrate, malate, tartrate, ascorbate, glucuronate, α-ketoglutarate, benzoate and salicylate;
$C_{1-12}$ alkylsulfonate is selected from the group consisting of mesylate and camsylate;
arylsulfonate is selected from the group consisting of besylate and tosylate, In a preferred embodiment, the pharmaceutically acceptable ion is the malate.

In a particularly preferred embodiment, the pharmaceutically acceptable ion is the hydrogen malate.

The term "hydrogen malate" means the monocarboxylate.

In a further particularly preferred embodiment, the hydrogen malate is the D-, L- or DL-stereoisomer.

In a further preferred embodiment, the pharmaceutically acceptable anion is the tartrate.

In a particularly preferred embodiment, the pharmaceutically acceptable anion is the hydrogen tartrate.

The term "hydrogen tartrate" means the monocarboxylate

In a further particularly preferred embodiment, the hydrogen tartrate ion is the D-, L- or DL-stereoisomer.

The preparation of D-, L- or DL-stereoisomers of hydrogen malate or hydrogen tartrate is particularly preferred since the method according to the invention provides these compounds in a high yield and in a crystallinity which is particularly advantageous in view of the handling and further processing of the salt.

Typically, crystalline compounds are already obtained directly in the salt metathesis reaction.

This is advantageous compared to e.g. a counter-ion exchange via ion-exchanger where the compounds typically are obtained in an amorphous form and have to be crystallized in a subsequent step.

Cation $Cat^+$ Related to the Pharmaceutically Acceptable Ion $Y^-$ to be Subjected to Salt Metathesis with nicotinamide-β-D-ribofuranoside Bromide, Chloride, Iodide, Triflate, Nonaflate, Fluorosulfonate or Perchlorate or nicotinamide-2,3,5-tri-O-acyl-β-D-ribofuranoside Bromide, Chloride, Iodide, Triflate, Nonaflate, Fluorosulfonate or Perchlorate Nicotinamide-β-D-ribofuranoside bromide, chloride, iodide, triflate, nonaflate, fluorosulfonate or perchlorate or nicotinamide-2,3,5-tri-O-acyl-β-D-ribofuranoside bromide, chloride, iodide, triflate, nonaflate, fluorosulfonate or perchlorate can be subjected to salt metathesis using basically any salt having a pharmaceutically acceptable anion.

Although not limited, cation Cat$^+$ as used in connection with the pharmaceutically acceptable anion preferably originates from an ammonium salt or a phosphonium salt.

Preferably, in one embodiment, the cation of the salt is [NR$^1$R$^2$R$^3$R$^4$]$^+$, wherein R$^1$, R$^2$, R$^3$ and R$^4$ are independently selected from H, C$_{1-12}$ alkyl and aryl, optionally substituted.

In one embodiment, the cation of the salt is NH$_4^+$.

In a preferred embodiment, the cation of the salt originates from a primary ammonium salt, i.e. the cation of the salt is [NR$^1$H$_3$]$^+$, wherein R$^1$ is selected from C$_{1-12}$ alkyl and aryl, optionally substituted.

In another preferred embodiment, the cation of the salt originates from a secondary ammonium salt, i.e. the cation of the salt is [NR$^1$R$^2$H$_2$]$^+$, wherein R$^1$ and R$^2$ are independently selected from C$_{1-12}$ alkyl and aryl, optionally substituted.

In a further preferred embodiment, one of R$^1$, R$^2$, R$^3$ and R$^4$ in [NR$^1$R$^2$R$^3$R$^4$]$^+$ is H. Accordingly, the cation of the salt originates from a tertiary ammonium salt, i.e. the cation of the salt is [NR$^1$R$^2$R$^3$H]$^+$, wherein R$^1$, R$^2$ and R$^3$ are independently selected from C$_{1-12}$ alkyl and aryl, optionally substituted.

In still another preferred embodiment, the cation is a quaternary ammonium salt. Accordingly, the cation of the salt is [NR$^1$R$^2$R$^3$R$^4$]$^+$, wherein R$^1$, R$^2$, R$^3$ and R$^4$ are independently selected from C$_{1-12}$ alkyl and aryl, optionally substituted.

In a preferred embodiment, [NR$^1$R$^2$R$^3$R$^4$]$^+$ is [N(C$_2$H$_5$)$_4$]$^+$ or [N(C$_4$H$_9$)$_4$]$^+$.

In a further preferred embodiment, one of R$^1$, R$^2$, R$^3$ and R$^4$ is benzyl.

In another embodiment, the cation of the salt originates from a N-heterocyclic aromatic system or an N-alkylated heterocyclic aromatic system such as pyridine or n-methyl pyridine.

In another embodiment, the cation of the salt is [PR$^1$R$^2$R$^3$R$^4$]$^+$, wherein R$^1$, R$^2$, R$^3$ and R$^4$ are independently selected from H, C$_{1-12}$ alkyl and aryl, optionally substituted.

In a further preferred embodiment, one of R$^1$, R$^2$, R$^3$ and R$^4$ in [PR$^1$R$^2$R$^3$R$^4$]$^+$ is H.

The use of lithium salts or sodium salts comprising a pharmaceutically acceptable anion in the salt metathesis reaction according to the invention is conceivable, too.

Suitable salts are commercially available or may be prepared according to known methods, e.g. by reacting triethylamine or tributylamine or tetraethylammonium hydroxide or tetrabutylammonium hydroxide or benzyltrimethyl ammonium hydroxide with an acid such as sulfuric acid or a carboxylic acid such as malic acid or tartraric acid in molar ratios that allow for the preparation of monovalent or divalent anions.

Solvent

The salt metathesis may be performed without a solvent, i.e. via salt metathesis of a solid nicotinamide-β-D-ribofuranoside salt or solid nicotinamide-2,3,5-tri-O-acyl-β-D-ribofuranoside salt with e.g. a liquid salt.

In a preferred embodiment, the salt metathesis in step (A) is performed in presence of a solvent.

The following non-limiting embodiments I, II, III or IV for performing the above-defined salt metathesis reaction are preferred:

Embodiment I: The solvent is selected such that NR$^+$Br$^-$ (or AcONR$^+$Br$^-$) and Cat$^+$Y$^-$ are both soluble in said solvent, however NR$^+$Y$^-$ (or AcONR$^+$Y$^-$) obtained in step (A) is not soluble in said solvent and precipitates, whereas Cat$^+$Br$^-$ is soluble. NR$^+$Y$^-$ (or AcONR$^+$Y$^-$) may then be isolated by filtration.

Embodiment II: The solvent is selected such that NR$^+$Br$^-$ (or AcONR$^+$Br$^-$) and Cat$^+$Y$^-$ are both soluble in said solvent, however NR$^+$Y$^-$ (or AcONR$^+$Y$^-$) obtained in step (A) is soluble in said solvent, whereas Cat$^+$Br$^-$ is not soluble and precipitates. NR$^+$Y$^-$ (or AcONR$^+$Y$^-$) may e.g. then be isolated from the supernatant according to known techniques.

Embodiment III: The solvent is selected such that NR$^+$Br$^-$ and NR$^+$Y$^-$ (or AcONR$^+$Br$^-$ and AcONR$^+$Y$^-$) obtained in step (A) are not soluble in said solvent, whereas both Cat$^+$Br$^-$ and Cat$^+$Y$^-$ are soluble. NR$^+$Y$^-$ (or AcONR$^+$Y$^-$) may e.g. then be isolated by filtration.

Embodiment IV: The solvent is selected such that NR$^+$Br$^-$ and NR$^+$Y$^-$ (or AcONR$^+$Br$^-$ and AcONR$^+$Y$^-$) obtained in step (A) are soluble in said solvent, whereas Cat$^+$Y$^-$ and Cat$^+$Br$^-$ are not soluble. NR$^+$Y$^-$ (or AcONR$^+$Y$^-$) may e.g. then be isolated from the supernatant according to known techniques.

Instead of NR$^+$Br$^-$ and AcONR$^+$Br$^-$ also NR$^+$Cl$^-$ and AcONR$^+$Cl$^-$, NR$^+$I$^-$ and AcONR$^+$I$^-$, NR$^+$CF$_3$SO$_3^-$ and AcONR$^+$CF$_3$SO$_3^-$ or NR$^+$n-C$_4$F$_9$SO$_3^-$ and AcONR$^+$n-C$_4$F$_9$SO$_3^-$, NR$^+$FSO$_3^-$ and AcONR$^+$FSO$_3^-$ or NR$^+$ClO$_4^-$ and AcONR$^+$ClO$_4^-$ may be used in embodiments I to IV.

Accordingly, by appropriate choice of the solvent used in the salt metathesis reaction defined in step (A), i.e. by determining a solubility chart, the result of the salt metathesis reaction can be predicted. The person skilled in the art may be expected to determine such solubility chart by routine experimentation.

Embodiment I provides for good results provided Cat Y is an ammonium salt or phosphonium salt as defined above, preferably an ammonium salt.

In a further preferred embodiment, Embodiment I provides for good results provided an alcohol is used as solvent, or the solvent comprises an alcohol, and Cat$^+$Y$^-$ preferably is an ammonium salt or phosphonium salt as defined above, preferably an ammonium salt.

Preferably, the alcohol used for salt metathesis is selected from the group consisting of methanol, ethanol, a propanol or a butanol, or a mixture of two or more thereof, optionally the alcohol or the mixture comprising water.

The inventors of the present invention discovered that unexpectedly the formed nicotinamide-β-D-ribofuranoside and nicotinamide-triacyl-O-β-D-ribofuranoside salts provide for unusual high solubility differences compared to the nicotinamide-β-D-ribofuranoside bromide, chloride, iodide, triflate, nonaflate, fluorosulfonate or perchlorate, respectively nicotinamide-tri-O-acyl-β-D-ribofuranoside bromide, chloride, iodide, triflate, nonaflate, fluorosulfonate or perchlorate used for salt metathesis in the specified alcohol such that under the reaction conditions in particular embodiment I is the method of choice.

Preferably, in step (A) a saturated solution of the nicotinamide-β-D-ribofuranoside bromide, chloride, iodide, triflate, nonaflate, fluorosulfonate or perchlorate or the nicotinamide-2,3,5-tri-O-acyl-β-D-ribofuranoside bromide, chloride, iodide, triflate, nonaflate, fluorosulfonate or perchlorate in one or more of the alcohols defined above, optionally comprising water, and a suitable ammonium salt or phosphonium salt are combined with one another, wherein step (A) takes place, i.e. the nicotinamide-β-D-ribofuranoside salt or the nicotinamide-2,3,5-tri-O-acyl-β-D-ribofuranoside salt generated by counter-ion exchange precipitates and can be isolated by filtration.

The term "saturated solution" means in a preferred embodiment that concentrated solutions of NR$^+$Br$^-$ (or AcONR$^+$Br$^-$) and Cat$^+$Y$^-$ are prepared such that the solubility limit at 23° C. is not exceeded.

The term "saturated solution" means in another preferred embodiment that concentrated solutions of NR$^+$Br$^-$, NR$^+$Cl$^-$, NR$^+$I$^-$, NR$^+$CF$_3$SO$_3^-$, NR$^+$n-C$_4$F$_9$SO$_3^-$, NR$^+$FSO$_3^-$ or NR$^+$ClO$_4^-$ (or AcONR$^+$Br$^-$, AcONR$^+$Cl$^-$, AcONR$^+$I$^-$, AcONR$^+$CF$_3$SO$_3^-$, AcONR$^+$n-C$_4$F$_9$SO$_3^-$, AcONR$^+$FSO$_3^-$ or AcONR$^+$ClO$_4^-$) and Cat$^+$Y$^-$ are prepared such that the solubility limit at 23° C. is not exceeded.

Preferably, the salt metathesis reaction according to step (A) is performed at ambient temperature, i.e. in the range of from 5 to 60° C., preferably 10 to 40° C.

It is evident that the salt metathesis reaction defined in step (A) is not restricted to the ammonium salts or phosphonium salts and the alcohol defined above.

In a preferred embodiment, the invention relates to a method of making a nicotinamide-β-D-ribofuranoside salt or a nicotinamide-2,3,5-tri-O-acyl-β-D-ribofuranoside salt, wherein step (A) as defined in the first and the second aspect comprises at least steps (A1) and (A2):

(A1) reacting $NH_3$ or $NR^1H_2$ or $NR^1R^2H$ or $NR^1R^2R^3$ or $[NR^1R^2R^3R^4]OH$ with an acid preferably comprising a pharmaceutically acceptable anion to afford the respective ammonium salt, wherein $R^1$, $R^2$, $R^3$ and $R^4$ are independently selected from $C_{1-12}$ alkyl and aryl, optionally substituted.

(A2) reacting nicotinamide-β-D-ribofuranoside bromide, chloride, iodide, triflate, nonaflate, fluorosulfonate or perchlorate or nicotinamide-2,3,5-tri-O-acyl-β-D-ribofuranoside bromide, chloride, iodide, triflate, nonaflate, fluorosulfonate or perchlorate with the ammonium salt from step (A1) to perform salt metathesis comprising counter-ion exchange to afford the nicotinamide-β-D-ribofuranoside salt or the nicotinamide-2,3,5-tri-O-acyl-β-D-ribofuranoside salt, wherein acyl has the meaning as defined above.

In a preferred embodiment, $NR^1R^2R^3$ or $[NR^1R^2R^3R^4]OH$ is used in step (A1).

Likewise, in another embodiment, the invention relates to a method of making a nicotinamide-β-D-ribofuranoside salt or a nicotinamide-2,3,5-tri-O-acyl-β-D-ribofuranoside salt, the method comprising:

(A1) reacting $PH_3$ or $PR^1H_2$ or $PR^1R^2H$ or $PR^1R^2R^3$ or $[PR^1R^2R^3R^4]OH$ with an acid to afford the respective phosphonium salt, wherein $R^1$, $R^2$, $R^3$ and $R^4$ are independently selected from $C_{1-12}$ alkyl and aryl, optionally substituted.

(A2) reacting nicotinamide-β-D-ribofuranoside bromide, chloride, iodide, triflate, nonaflate, fluorosulfonate or perchlorate or nicotinamide-2,3,5-tri-O-acyl-β-D-ribofuranoside bromide, chloride, iodide, triflate, nonaflate, fluorosulfonate or perchlorate with the phosphonium salt from step ($A_0$) to perform salt metathesis comprising counter-ion exchange to afford the nicotinamide-β-D-ribofuranoside salt or the nicotinamide-2,3,5-tri-O-acyl-β-D-ribofuranoside salt, wherein acyl has the meaning as defined above.

In a preferred embodiment, $PR^1R^2R^3$ or $[PR^1R^2R^3R^4]OH$ is used in step (A1).

Further Purification

If necessary, the product obtained in step (A) or step (B) may be purified according to known methods in order to obtain the pure β-anomer.

In one embodiment, the product may be recrystallized.

In another embodiment, the product may be dissolved in a suitable solvent and then precipitated by addition of a solvent, in which the product is not soluble.

Accordingly, the method as defined in the first, second or third aspect, further comprises step (C):

(C) purifying the salt obtained in step (A) or (B), preferably by crystallization.

In one embodiment, the method according to the invention may start in step (A) from pure β-anomers, i.e. pure nicotinamide-β-D-ribofuranoside bromide, chloride, iodide, triflate, nonaflate, fluorosulfonate or perchlorate or pure nicotinamide-2,3,5-O-triacyl-β-D-ribofuranoside bromide, chloride, iodide, triflate, nonaflate, fluorosulfonate or perchlorate.

The term "pure" means that nicotinamide-β-D-ribofuranoside bromide, chloride, iodide, triflate, nonaflate, fluorosulfonate or perchlorate or nicotinamide-2,3,5-O-triacyl-β-D-ribofuranoside bromide, chloride, iodide, triflate, nonaflate, fluorosulfonate or perchlorate may contain up to 5% of the α-anomer.

In one embodiment, the salts are provided in isolated form, optionally purified, prior to their use in step (A).

In another embodiment, the method may start in step (A) from β-anomers containing more than 5% of the α-anomer, i.e. non-purified nicotinamide-β-D-ribofuranoside bromide, chloride, iodide, triflate, nonaflate, fluorosulfonate or perchlorate or non-purified nicotinamide-2,3,5-O-triacyl-β-D-ribofuranoside bromide, chloride, iodide, triflate, nonaflate, fluorosulfonate or perchlorate.

In one embodiment, the salts are provided in dissolved form as generated in the respective synthesis prior to their use in step (A), i.e. in non-purified form.

Summing up, the method according to the invention advantageously allows for the preparation of nicotinamide-β-D-ribofuranoside salts on various pathways, preferably pathways according to pathways (P1) to (P5), either starting from pure β-anomers or β-anomers containing the α-anomer:

Pathway (P1) comprises steps (α), (β), (γ) and (δ):
(α) cleaving the acyl groups in nicotinamide-2,3,5-O-triacyl-β-D-ribofuranoside bromide, chloride, iodide, triflate, nonaflate, fluorosulfonate or perchlorate containing up to 5% of the α-anomer to afford the nicotinamide-β-D-ribofuranoside bromide, chloride, iodide, triflate, nonaflate, fluorosulfonate or perchlorate;
(β) isolating and optionally purifying the nicotinamide-β-D-ribofuranoside bromide, chloride, iodide, triflate, nonaflate, fluorosulfonate or perchlorate;
(γ) subjecting the nicotinamide-β-D-ribofuranoside bromide, chloride, iodide, triflate, nonaflate, fluorosulfonate or perchlorate to salt metathesis to afford the nicotinamide-β-D-ribofuranoside salt;
(δ) isolating and optionally purifying the nicotinamide-β-D-ribofuranoside salt.

Pathway (P2) comprises steps (α), (β), (γ) and (δ):
(α) subjecting a nicotinamide-2,3,5-O-triacyl-β-D-ribofuranoside bromide, chloride, iodide, triflate, nonaflate, fluorosulfonate or perchlorate containing up to 5% of the α-anomer to salt metathesis to afford a nicotinamide-2,3,5-O-triacyl β-D-ribofuranoside salt;
(β) isolating and optionally purifying the nicotinamide-2,3,5-O-triacyl-β-D-ribofuranoside;
(γ) cleaving the acyl groups in the nicotinamide-2,3,5-O-triacyl-β-D-ribofuranoside salt to afford a nicotinamide-β-D-ribofuranoside salt;
(δ) isolating and optionally purifying the nicotinamide-β-D-ribofuranoside salt.

Pathway (P3) comprises steps (α) and (β):
(α) cleaving the acyl groups in nicotinamide-2,3,5-O-triacyl-β-D-ribofuranoside bromide, chloride, iodide, triflate, nonaflate, fluorosulfonate or perchlorate containing up to 5% of the α-anomer to afford the nicotinamide-β-D-ribofuranoside bromide, chloride, iodide, triflate, nonaflate, fluorosulfonate or perchlorate and subjecting the formed nicotinamide-β-D-ribofuranoside bromide, chloride, iodide, triflate, nonaflate, fluorosulfonate or perchlorate without prior isolation to salt metathesis to afford a nicotinamide-β-D-ribofuranoside salt;
(β) isolating and optionally purifying the nicotinamide-β-D-ribofuranoside salt.

Pathway (P4) comprises steps (α), (β), (γ) and (δ):
(α) subjecting nicotinamide-2,3,5-O-triacyl-β-D-ribofuranoside bromide, chloride, iodide, triflate, nonaflate, fluorosulfonate or perchlorate containing more than 5% of the α-anomer to salt metathesis to afford a nicotinamide-2,3,5-O-triacyl β-D-ribofuranoside salt;
(β) isolating and optionally purifying the nicotinamide-2,3,5-O-triacyl-β-D-ribofuranoside;

(γ) cleaving the acyl groups in the nicotinamide-2,3,5-O-triacetyl-β-D-ribofuranoside salt to afford a nicotinamide-β-D-ribofuranoside salt;
(δ) isolating and optionally purifying the nicotinamide-β-D-ribofuranoside salt.

Pathway (P5) comprises steps (α) and (β):
(α) cleaving the acyl groups in nicotinamide-2,3,5-O-triacyl-β-D-ribofuranoside bromide, chloride, iodide, triflate, nonaflate, fluorosulfonate or perchlorate containing more than 5% of the α-anomer to afford the nicotinamide-β-D-ribofuranoside bromide, chloride, iodide, triflate, nonaflate, fluorosulfonate or perchlorate and subjecting the formed nicotinamide-β-D-ribofuranoside bromide, chloride, iodide, triflate, nonaflate, fluorosulfonate or perchlorate without prior isolation to salt metathesis to afford a nicotinamide-β-D-ribofuranoside salt;
(β) isolating and optionally purifying the nicotinamide-β-D-ribofuranoside salt.

The term "without prior isolation" as used in pathways (P3) and (P5) denotes that the salt metathesis is carried out in situ.

Preferably, the salts carrying the pharmaceutically acceptable anion are also formed in situ, i.e. in the reaction mixture obtained in the cleaving step of the acyl groups.

In one embodiment, the various pathways are exemplarily shown in the following scheme starting from nicotinamide-2,3,5-O-triacetyl-β-D-ribofuranoside bromide preparing the L-hydrogen tartrates:

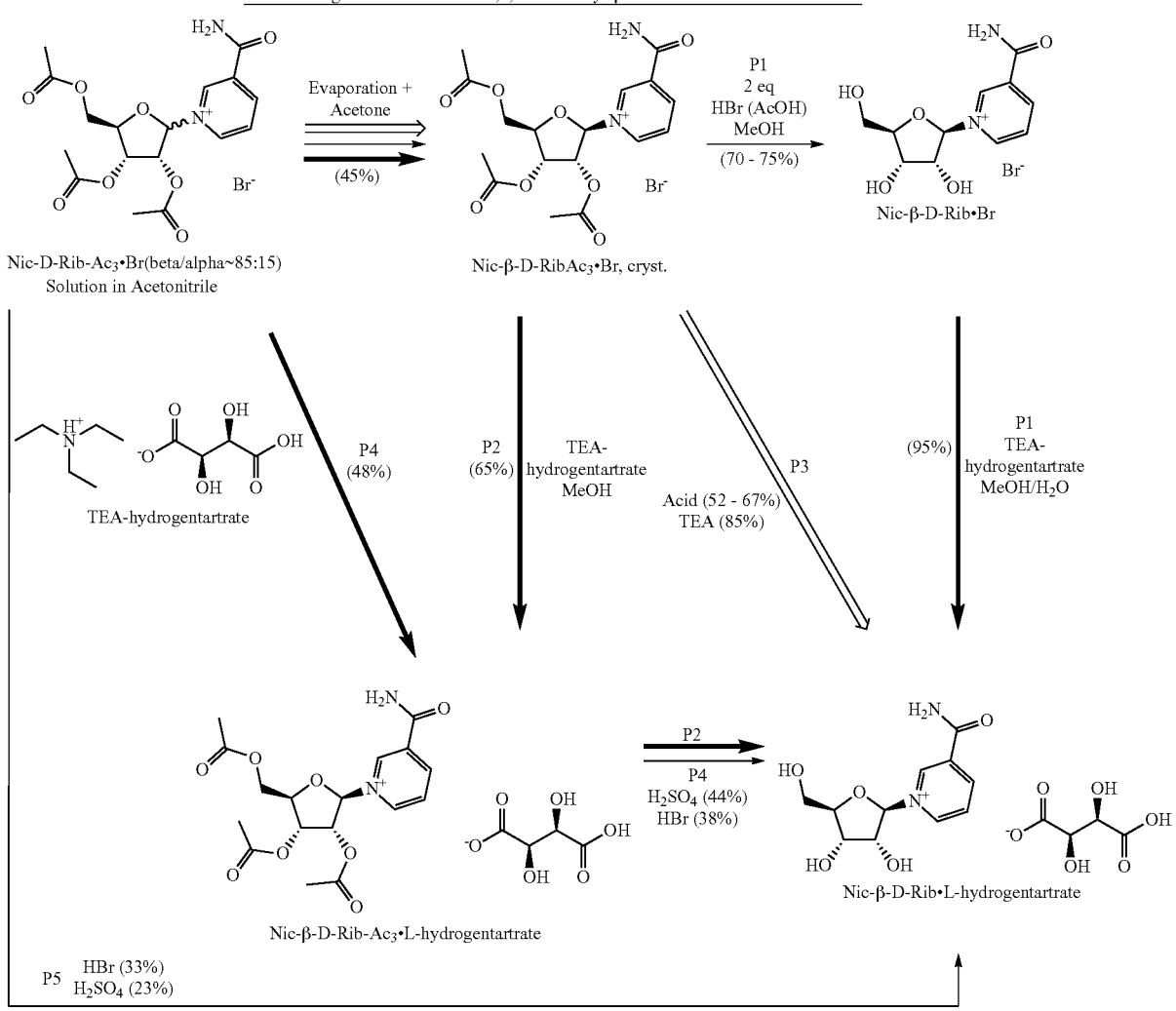

Scheme 1
Pathways P1 to P5 for making nicotinamide-β-D-ribofuranoside L-hydrogen tartrate starting from nicotinamide-2,3,5-O-triacetyl-β-D-ribofuranoside bromide In another embodiment, the various pathways P1 to P5 are exemplarily shown in Scheme 2 starting from nicotinamide-2,3,5-O-triacetyl-β-D-ribofuranoside triflate preparing the L-hydrogen tartrates (pathways P2 and P3 are not shown):

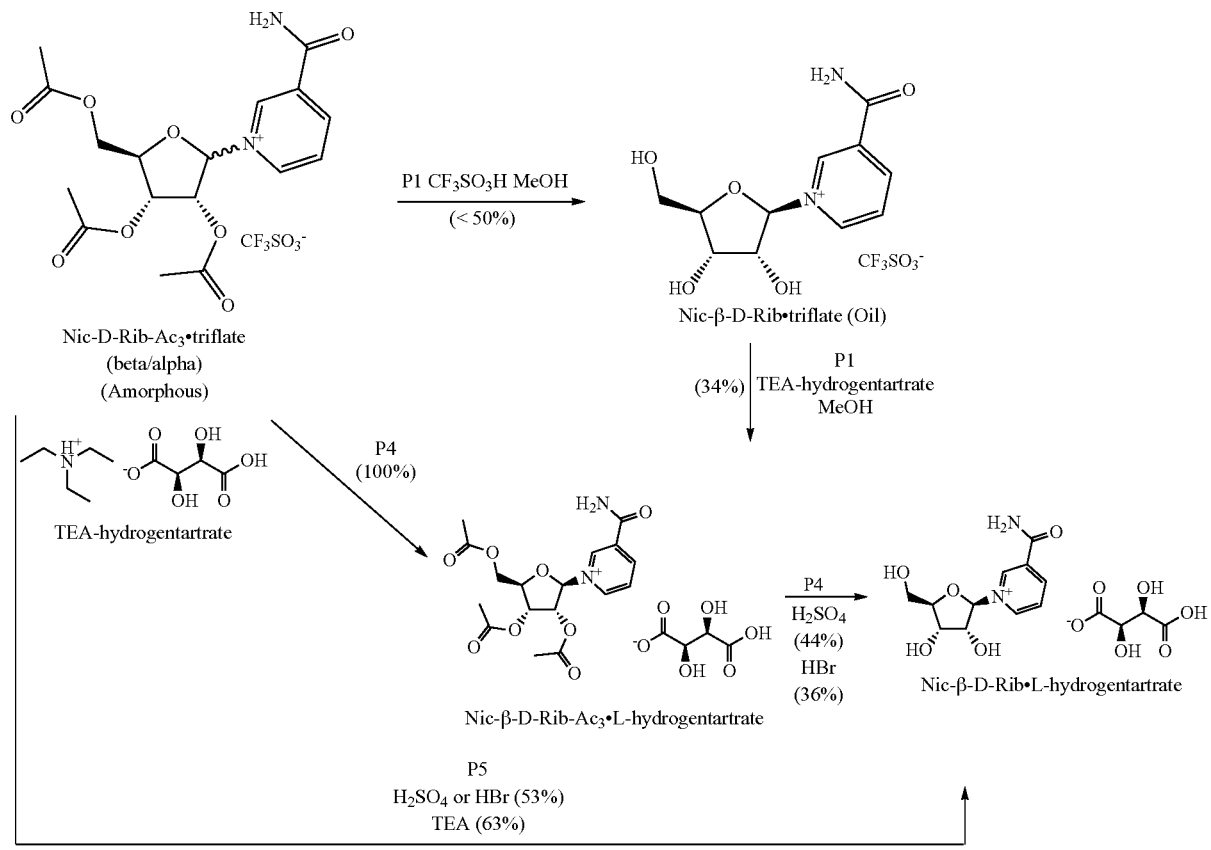

As already mentioned above, in one embodiment, cleavage of acyl groups in nicotinamide-2,3,5-tri-O-acyl-β-D-ribofuranoside salts may be performed under acidic conditions using sulfuric acid, hydrochloric acid or hydrobromic acid or hydroiodic acid The resulting acidic mixtures may be neutralized with ammonia or amines such as triethylamine or tributylamine, if necessary, prior to isolating the respective nicotinamide-β-D-ribofuranoside salts In another embodiment, cleavage of acyl groups in nicotinamide-2,3,5-tri-O-acyl-β-D-ribofuranoside salts may be performed under basis conditions using ammonia or triethylamine or tributylamine prior to isolating the respective nicotinamide-β-D-ribofuranoside salts.

Fourth Aspect: Crystalline nicotinamide-β-D-ribofuranoside Hydrogen Malates, nicotinamide-β-D-ribofuranoside Hydrogen Tartrates, nicotinamide-2,3,5-O-triacetyl-β-D-ribofuranoside Malates, and nicotinamide-2,3,5-O-triacetyl-β-D-ribofuranoside Tartrates According to a fourth aspect, the invention relates to crystalline nicotinamide-β-D-ribofuranoside malates, nicotinamide-β-D-ribofuranoside tartrates, nicotinamide-2,3,5-O-triacetyl-β-D-ribofuranoside malates, and nicotinamide-2,3,5-O-triacetyl-β-D-ribofuranoside tartrates.

In a preferred embodiment, the invention relates to crystalline nicotinamide-β-D-ribofuranoside hydrogen malates, nicotinamide-β-D-ribofuranoside hydrogen tartrates, nicotinamide-2,3,5-O-triacetyl-β-D-ribofuranoside hydrogen malates, and nicotinamide-2,3,5-O-triacetyl-β-D-ribofuranoside hydrogen tartrates.

In a particularly preferred embodiment, the crystalline nicotinamide-β-D-ribofuranoside hydrogen malate is nicotinamide-β-D-ribofuranoside D-hydrogen malate, which may be characterized by a powder X-ray diffraction pattern having peaks substantially as provided in Table 1, below, ±0.2 degrees two theta:

TABLE 1

| Pos. [°2Th.] | Height [cts] | FWHM Left [°2Th.] | d-spacing [Å] | Rel. Int. [%] |
|---|---|---|---|---|
| 11.8481 | 445.20 | 0.1535 | 7.46957 | 0.61 |
| 12.6145 | 22336.51 | 0.1663 | 7.01743 | 30.71 |
| 13.0454 | 990.49 | 0.1023 | 6.78661 | 1.36 |
| 13.6055 | 7710.12 | 0.1407 | 6.50845 | 10.60 |
| 14.8288 | 14677.80 | 0.1407 | 5.97418 | 20.18 |
| 15.3150 | 3657.25 | 0.1279 | 5.78560 | 5.03 |
| 16.6048 | 27830.00 | 0.1535 | 5.33898 | 38.27 |
| 16.8966 | 21052.43 | 0.1407 | 5.24745 | 28.95 |
| 17.4485 | 11645.88 | 0.1535 | 5.08269 | 16.01 |
| 17.7534 | 3843.61 | 0.1407 | 4.99606 | 5.29 |
| 19.1083 | 13443.46 | 0.1535 | 4.64476 | 18.49 |
| 19.8613 | 2277.97 | 0.1023 | 4.47034 | 3.13 |
| 20.8582 | 8387.39 | 0.1535 | 4.25887 | 11.53 |
| 22.4545 | 72723.85 | 0.1663 | 3.95960 | 100.00 |

TABLE 1-continued

| Pos. [°2Th.] | Height [cts] | FWHM Left [°2Th.] | d-spacing [Å] | Rel. Int. [%] |
|---|---|---|---|---|
| 22.9093 | 12085.33 | 0.1023 | 3.88200 | 16.62 |
| 23.0396 | 13135.67 | 0.1279 | 3.86035 | 18.06 |
| 24.1487 | 59629.80 | 0.1663 | 3.68550 | 81.99 |
| 24.9146 | 28316.42 | 0.1791 | 3.57392 | 38.94 |
| 25.2144 | 7756.64 | 0.1151 | 3.53210 | 10.67 |
| 25.9681 | 34260.16 | 0.1791 | 3.43127 | 47.11 |
| 26.6864 | 10373.63 | 0.1872 | 3.33776 | 14.26 |
| 26.7773 | 7203.21 | 0.0624 | 3.33490 | 9.90 |
| 27.2747 | 3052.68 | 0.0936 | 3.26708 | 4.20 |
| 27.5074 | 7926.64 | 0.1716 | 3.23997 | 10.90 |
| 27.8283 | 2567.70 | 0.1560 | 3.20334 | 3.53 |
| 28.4116 | 3658.38 | 0.1872 | 3.13888 | 5.03 |
| 28.8702 | 3091.52 | 0.2184 | 3.09006 | 4.25 |
| 29.6423 | 5092.55 | 0.1872 | 3.01130 | 7.00 |
| 30.3593 | 5978.38 | 0.2340 | 2.94180 | 8.22 |
| 30.7689 | 1776.07 | 0.1248 | 2.90356 | 2.44 |
| 31.0365 | 3671.22 | 0.1560 | 2.87914 | 5.05 |
| 31.1463 | 3208.07 | 0.1248 | 2.87636 | 4.41 |
| 31.9512 | 3909.20 | 0.1560 | 2.79877 | 5.38 |
| 33.1011 | 2415.68 | 0.1872 | 2.70412 | 3.32 |
| 33.4482 | 1483.40 | 0.1872 | 2.67685 | 2.04 |
| 34.0593 | 9996.43 | 0.2028 | 2.63021 | 13.75 |
| 34.8632 | 6370.44 | 0.2028 | 2.57137 | 8.76 |
| 35.0955 | 3176.40 | 0.1092 | 2.55488 | 4.37 |
| 35.9193 | 4930.68 | 0.2028 | 2.49815 | 6.78 |
| 36.4557 | 1816.82 | 0.1092 | 2.46262 | 2.50 |
| 36.8016 | 12666.84 | 0.2028 | 2.44026 | 17.42 |
| 37.0816 | 3874.77 | 0.2184 | 2.42247 | 5.33 |
| 37.9077 | 1556.53 | 0.2184 | 2.37157 | 2.14 |
| 38.4661 | 2055.02 | 0.1560 | 2.33841 | 2.83 |
| 38.6659 | 3561.10 | 0.1248 | 2.32679 | 4.90 |
| 38.8999 | 2595.21 | 0.1248 | 2.31332 | 3.57 |
| 39.5529 | 483.59 | 0.1872 | 2.27663 | 0.66 |
| 40.0729 | 1196.25 | 0.1248 | 2.24827 | 1.64 |
| 40.4331 | 913.59 | 0.2028 | 2.22907 | 1.26 |
| 41.3218 | 2816.77 | 0.1872 | 2.18316 | 3.87 |

In a further particularly preferred embodiment, the crystalline nicotinamide-β-D-ribofuranoside hydrogen malate is nicotinamide-β-D-ribofuranoside L-hydrogen malate, which may be characterized by a powder X-ray diffraction pattern having peaks substantially as provided in Table 2, below, ±0.2 degrees two theta:

TABLE 2

| Pos. [°2Th.] | Height [cts] | FWHM Left [°2Th.] | d-spacing [Å] | Rel. Int. [%] |
|---|---|---|---|---|
| 6.6733 | 11000.76 | 0.1279 | 13.24569 | 8.35 |
| 11.6730 | 10108.79 | 0.1023 | 7.58124 | 7.67 |
| 12.6182 | 2979.47 | 0.1023 | 7.01537 | 2.26 |
| 13.2792 | 4005.91 | 0.1023 | 6.66763 | 3.04 |
| 14.0796 | 1500.07 | 0.0895 | 6.29033 | 1.14 |
| 15.8520 | 18627.05 | 0.1151 | 5.59079 | 14.14 |
| 16.6325 | 17905.54 | 0.1279 | 5.33014 | 13.59 |
| 17.0744 | 24889.77 | 0.1407 | 5.19318 | 18.90 |
| 17.7100 | 39009.26 | 0.1279 | 5.00821 | 29.62 |
| 18.6845 | 11202.45 | 0.1151 | 4.74915 | 8.50 |
| 19.8229 | 39113.57 | 0.1023 | 4.47890 | 29.70 |
| 19.9594 | 30901.54 | 0.0895 | 4.44858 | 23.46 |
| 21.4914 | 131716.20 | 0.1535 | 4.13481 | 100.00 |
| 21.9147 | 8196.29 | 0.1279 | 4.05590 | 6.22 |
| 22.6727 | 4614.03 | 0.1151 | 3.92199 | 3.50 |
| 23.3985 | 4580.59 | 0.1023 | 3.80195 | 3.48 |
| 23.5603 | 2609.14 | 0.0768 | 3.77619 | 1.98 |
| 24.4454 | 15991.37 | 0.1407 | 3.64145 | 12.14 |
| 25.0307 | 5436.84 | 0.1151 | 3.55761 | 4.13 |
| 25.3173 | 14403.35 | 0.1407 | 3.51797 | 10.94 |
| 25.7774 | 39496.78 | 0.1279 | 3.45622 | 29.99 |
| 26.5990 | 530.11 | 0.0768 | 3.35130 | 0.40 |
| 27.2687 | 37878.08 | 0.1535 | 3.27050 | 28.76 |
| 27.7679 | 8088.77 | 0.1407 | 3.21283 | 6.14 |
| 28.5924 | 37492.90 | 0.1407 | 3.12203 | 28.46 |

TABLE 2-continued

| Pos. [°2Th.] | Height [cts] | FWHM Left [°2Th.] | d-spacing [Å] | Rel. Int. [%] |
|---|---|---|---|---|
| 29.4458 | 10235.99 | 0.1535 | 3.03346 | 7.77 |
| 29.9251 | 1263.01 | 0.1023 | 2.98595 | 0.96 |
| 30.3346 | 1771.52 | 0.1279 | 2.94658 | 1.34 |
| 30.9962 | 7832.28 | 0.1407 | 2.88517 | 5.95 |
| 31.9611 | 3386.65 | 0.1151 | 2.80024 | 2.57 |
| 32.3205 | 3078.07 | 0.1151 | 2.76992 | 2.34 |
| 32.6276 | 5095.47 | 0.1407 | 2.74454 | 3.87 |
| 33.2109 | 2336.00 | 0.1151 | 2.69767 | 1.77 |
| 33.5827 | 2533.18 | 0.1791 | 2.66864 | 1.92 |
| 34.4375 | 8372.54 | 0.1092 | 2.60218 | 6.36 |
| 34.5287 | 8604.75 | 0.0624 | 2.60196 | 6.53 |
| 35.2507 | 1734.20 | 0.1872 | 2.54399 | 1.32 |
| 35.9225 | 627.59 | 0.1560 | 2.49794 | 0.48 |
| 36.3727 | 1521.95 | 0.1560 | 2.46805 | 1.16 |
| 36.7591 | 10921.08 | 0.0624 | 2.44299 | 8.29 |
| 36.8558 | 16598.23 | 0.0780 | 2.43680 | 12.60 |
| 36.9072 | 15801.89 | 0.0624 | 2.43353 | 12.00 |
| 37.0273 | 9229.76 | 0.0780 | 2.43193 | 7.01 |
| 37.5024 | 915.96 | 0.1248 | 2.39626 | 0.70 |
| 37.6170 | 1026.81 | 0.1248 | 2.38922 | 0.78 |
| 37.9992 | 4085.21 | 0.1716 | 2.36606 | 3.10 |
| 38.3253 | 2144.23 | 0.1092 | 2.34668 | 1.63 |
| 38.7147 | 621.22 | 0.1560 | 2.32397 | 0.47 |
| 39.3994 | 2599.18 | 0.1404 | 2.28514 | 1.97 |
| 40.1021 | 988.71 | 0.1248 | 2.24670 | 0.75 |

In a further particularly preferred embodiment, the crystalline nicotinamide-β-D-ribofuranoside hydrogen malate is nicotinamide-β-D-ribofuranoside DL-hydrogen malate, which may be characterized by a powder X-ray diffraction pattern having peaks substantially as provided in Table 3, below, ±0.2 degrees two theta:

TABLE 3

| Pos. [°2Th.] | Height [cts] | FWHM Left [°2Th.] | d-spacing [Å] | Rel. Int. [%] |
|---|---|---|---|---|
| 6.4916 | 602.91 | 0.2047 | 13.61608 | 2.47 |
| 12.6712 | 9566.63 | 0.1919 | 6.98619 | 39.22 |
| 13.5865 | 1644.76 | 0.3070 | 6.51749 | 6.74 |
| 14.8721 | 5163.66 | 0.3070 | 5.95686 | 21.17 |
| 16.6660 | 14179.37 | 0.2430 | 5.31953 | 58.13 |
| 16.9489 | 7986.14 | 0.1279 | 5.23135 | 32.74 |
| 17.7388 | 3121.02 | 0.1791 | 5.00015 | 12.79 |
| 19.0726 | 3887.84 | 0.3582 | 4.65339 | 15.94 |
| 20.0028 | 1196.35 | 0.2558 | 4.43904 | 4.90 |
| 20.8961 | 1618.71 | 0.3070 | 4.25124 | 6.64 |
| 21.6668 | 3108.24 | 0.1791 | 4.10174 | 12.74 |
| 22.5350 | 13238.45 | 0.2558 | 3.94563 | 54.27 |
| 23.1389 | 8854.70 | 0.1151 | 3.84401 | 36.30 |
| 24.1793 | 24392.79 | 0.2686 | 3.68090 | 100.00 |
| 24.9889 | 9891.47 | 0.1151 | 3.56347 | 40.55 |
| 25.9744 | 12996.05 | 0.1407 | 3.43045 | 53.28 |
| 26.7055 | 4918.49 | 0.2814 | 3.33817 | 20.16 |
| 27.4357 | 3377.82 | 0.3326 | 3.25097 | 13.85 |
| 28.7541 | 1330.72 | 0.3582 | 3.10484 | 5.46 |
| 29.6501 | 881.37 | 0.1791 | 3.01302 | 3.61 |
| 30.4640 | 1495.16 | 0.2558 | 2.93435 | 6.13 |
| 31.0878 | 1291.15 | 0.2303 | 2.87689 | 5.29 |
| 32.0173 | 1193.11 | 0.3070 | 2.79545 | 4.89 |
| 33.4314 | 911.84 | 0.2047 | 2.68037 | 3.74 |
| 34.0539 | 3246.16 | 0.2558 | 2.63279 | 13.31 |
| 35.0647 | 1874.40 | 0.2047 | 2.55917 | 7.68 |
| 35.9624 | 1143.74 | 0.3070 | 2.49733 | 4.69 |
| 36.7801 | 5938.21 | 0.3582 | 2.44366 | 24.34 |
| 37.9474 | 612.44 | 0.2047 | 2.37113 | 2.51 |
| 38.5227 | 1356.14 | 0.2558 | 2.33704 | 5.56 |
| 40.1563 | 339.33 | 0.2558 | 2.24566 | 1.39 |
| 41.3746 | 1129.63 | 0.2047 | 2.18231 | 4.63 |
| 43.0838 | 521.75 | 0.3070 | 2.09961 | 2.14 |

In a further particularly preferred embodiment, the crystalline nicotinamide-β-D-ribofuranoside hydrogen tartrate is nicotinamide-β-D-ribofuranoside D-hydrogen tartrate monohydrate which may be characterized by a powder X-ray diffraction pattern having peaks substantially as provided in Table 4, below, ±0.2 degrees two theta:

TABLE 4

| Pos. [°2Th.] | Height [cts] | FWHM Left [°2Th.] | d-spacing [Å] | Rel. Int. [%] |
|---|---|---|---|---|
| 8.4427 | 1105.85 | 0.1535 | 10.47327 | 1.22 |
| 11.5955 | 4172.99 | 0.1279 | 7.63174 | 4.61 |
| 12.2064 | 14705.94 | 0.1791 | 7.25111 | 16.24 |
| 13.0444 | 3289.98 | 0.0640 | 6.78714 | 3.63 |
| 13.5285 | 467.19 | 0.2047 | 6.54533 | 0.52 |
| 14.2848 | 1275.48 | 0.1535 | 6.20043 | 1.41 |
| 16.3545 | 21575.71 | 0.1404 | 5.41564 | 23.83 |
| 16.4347 | 15155.18 | 0.0780 | 5.40278 | 16.74 |
| 16.8125 | 4155.81 | 0.1560 | 5.26914 | 4.59 |
| 17.4631 | 12385.81 | 0.2028 | 5.07426 | 13.68 |
| 17.7789 | 3027.92 | 0.1872 | 4.98483 | 3.34 |
| 19.2171 | 2784.15 | 0.1560 | 4.61489 | 3.08 |
| 20.4255 | 3513.64 | 0.1872 | 4.34452 | 3.88 |
| 20.8956 | 4537.86 | 0.2028 | 4.24783 | 5.01 |
| 21.2720 | 6611.82 | 0.2028 | 4.17350 | 7.30 |
| 21.6994 | 70686.05 | 0.2652 | 4.09226 | 78.08 |
| 22.4487 | 2507.47 | 0.1560 | 3.95732 | 2.77 |
| 23.2293 | 33381.43 | 0.2184 | 3.82609 | 36.87 |
| 24.0319 | 90535.69 | 0.2184 | 3.70009 | 100.00 |
| 24.6286 | 18789.44 | 0.2496 | 3.61177 | 20.75 |
| 25.1774 | 1988.68 | 0.1872 | 3.53428 | 2.20 |
| 25.9477 | 2843.74 | 0.0936 | 3.43108 | 3.14 |
| 26.2952 | 18820.31 | 0.2496 | 3.38653 | 20.79 |
| 27.1345 | 12051.06 | 0.1560 | 3.28364 | 13.31 |
| 27.2135 | 8697.14 | 0.0780 | 3.28243 | 9.61 |
| 27.8905 | 9546.45 | 0.2496 | 3.19633 | 10.54 |
| 28.7630 | 14348.07 | 0.2184 | 3.10133 | 15.85 |
| 29.7764 | 29336.40 | 0.2496 | 2.99805 | 32.40 |
| 30.1789 | 1742.47 | 0.1560 | 2.95867 | 1.92 |
| 31.3589 | 2575.16 | 0.1404 | 2.85027 | 2.84 |
| 31.6114 | 6597.81 | 0.2028 | 2.82807 | 7.29 |
| 31.9725 | 5471.62 | 0.0624 | 2.79695 | 6.04 |
| 32.0262 | 4966.30 | 0.0936 | 2.79238 | 5.49 |
| 32.3674 | 2226.55 | 0.1248 | 2.76372 | 2.46 |
| 32.9500 | 4735.31 | 0.1872 | 2.71618 | 5.23 |
| 33.5558 | 3636.60 | 0.1560 | 2.66851 | 4.02 |
| 33.8129 | 6593.61 | 0.2496 | 2.64881 | 7.28 |
| 34.4780 | 3327.54 | 0.0780 | 2.59922 | 3.68 |
| 34.5356 | 3466.61 | 0.0936 | 2.59502 | 3.83 |
| 34.9811 | 3563.42 | 0.0780 | 2.56298 | 3.94 |
| 35.2429 | 3201.57 | 0.1560 | 2.54453 | 3.54 |
| 35.5541 | 1707.94 | 0.2184 | 2.52297 | 1.89 |
| 35.9811 | 1583.66 | 0.2184 | 2.49401 | 1.75 |
| 36.5723 | 4931.96 | 0.2340 | 2.45504 | 5.45 |
| 36.8813 | 2777.94 | 0.0780 | 2.43517 | 3.07 |
| 36.9482 | 3348.58 | 0.0936 | 2.43092 | 3.70 |
| 37.5567 | 11857.18 | 0.1248 | 2.39292 | 13.10 |
| 37.6362 | 10096.73 | 0.1404 | 2.38805 | 11.15 |
| 37.9557 | 1772.71 | 0.0936 | 2.36868 | 1.96 |
| 38.8483 | 1366.78 | 0.2496 | 2.31628 | 1.51 |

In a further particularly preferred embodiment, the crystalline nicotinamide-β-D-ribofuranoside hydrogen tartrate is nicotinamide-β-L-ribofuranoside L-hydrogen tartrate which may be characterized by a powder X-ray diffraction pattern having peaks substantially as provided in Table 5, below, ±0.2 degrees two theta:

TABLE 5

| Pos. [°2Th.] | Height [cts] | FWHM Left [°2Th.] | d-spacing [Å] | Rel. Int. [%] |
|---|---|---|---|---|
| 11.5117 | 11200.84 | 0.1535 | 7.68714 | 7.48 |
| 12.5883 | 4412.06 | 0.1279 | 7.03201 | 2.95 |
| 13.1382 | 5170.21 | 0.1407 | 6.73885 | 3.45 |
| 15.2469 | 8205.64 | 0.1535 | 5.81130 | 5.48 |
| 16.5219 | 3562.59 | 0.1407 | 5.36559 | 2.38 |

TABLE 5-continued

| Pos. [°2Th.] | Height [cts] | FWHM Left [°2Th.] | d-spacing [Å] | Rel. Int. [%] |
|---|---|---|---|---|
| 17.0294 | 46534.70 | 0.2175 | 5.20680 | 31.08 |
| 18.1885 | 3338.98 | 0.1279 | 4.87754 | 2.23 |
| 19.8576 | 1936.08 | 0.0895 | 4.47116 | 1.29 |
| 20.4805 | 370.08 | 0.1279 | 4.33657 | 0.25 |
| 21.2805 | 10137.23 | 0.1279 | 4.17530 | 6.77 |
| 22.1515 | 19394.41 | 0.1535 | 4.01307 | 12.96 |
| 22.7119 | 149703.60 | 0.1663 | 3.91531 | 100.00 |
| 23.2457 | 5221.79 | 0.0512 | 3.82660 | 3.49 |
| 23.6134 | 55914.11 | 0.1663 | 3.76782 | 37.35 |
| 24.0980 | 4114.15 | 0.0895 | 3.69314 | 2.75 |
| 24.4411 | 7765.26 | 0.1407 | 3.64207 | 5.19 |
| 24.7474 | 2024.08 | 0.1151 | 3.59769 | 1.35 |
| 25.2253 | 3310.99 | 0.1279 | 3.53061 | 2.21 |
| 25.6075 | 6304.59 | 0.1663 | 3.47876 | 4.21 |
| 26.0932 | 5687.76 | 0.1407 | 3.41511 | 3.80 |
| 26.7150 | 7166.98 | 0.1535 | 3.33701 | 4.79 |
| 27.5250 | 15137.56 | 0.2047 | 3.24062 | 10.11 |
| 27.8002 | 10629.70 | 0.1407 | 3.20916 | 7.10 |
| 29.8120 | 9459.96 | 0.1407 | 2.99703 | 6.32 |
| 30.1918 | 1599.73 | 0.1023 | 2.96019 | 1.07 |
| 31.1237 | 5868.31 | 0.1535 | 2.87364 | 3.92 |
| 31.4626 | 2170.24 | 0.2303 | 2.84346 | 1.45 |
| 32.9642 | 1814.09 | 0.0780 | 2.71504 | 1.21 |
| 33.0404 | 1877.55 | 0.0640 | 2.71119 | 1.25 |
| 33.2757 | 1050.97 | 0.0768 | 2.69256 | 0.70 |
| 33.4753 | 934.01 | 0.1023 | 2.67696 | 0.62 |
| 34.3911 | 2124.57 | 0.1023 | 2.60774 | 1.42 |
| 35.0605 | 9970.35 | 0.1560 | 2.55736 | 6.66 |
| 35.1625 | 8673.63 | 0.0936 | 2.55651 | 5.79 |
| 35.5173 | 3085.28 | 0.0624 | 2.52551 | 2.06 |
| 35.7881 | 10815.35 | 0.1716 | 2.50701 | 7.22 |
| 36.4366 | 3605.79 | 0.1716 | 2.46386 | 2.41 |
| 36.9228 | 808.98 | 0.2496 | 2.43253 | 0.54 |
| 37.5169 | 5337.75 | 0.1560 | 2.39536 | 3.57 |
| 38.2736 | 1182.17 | 0.2184 | 2.34973 | 0.79 |
| 38.8883 | 2409.84 | 0.1716 | 2.31399 | 1.61 |
| 39.6760 | 3066.92 | 0.1404 | 2.26985 | 2.05 |
| 40.2830 | 6176.85 | 0.1716 | 2.23703 | 4.13 |
| 40.5831 | 3705.39 | 0.0936 | 2.22118 | 2.48 |
| 41.7493 | 674.67 | 0.1872 | 2.16179 | 0.45 |
| 42.1741 | 751.98 | 0.1872 | 2.14099 | 0.50 |
| 42.5125 | 407.16 | 0.1404 | 2.12473 | 0.27 |
| 43.1209 | 825.80 | 0.0780 | 2.09615 | 0.55 |
| 43.9559 | 380.32 | 0.0936 | 2.05825 | 0.25 |
| 44.1732 | 743.15 | 0.0936 | 2.04863 | 0.50 |

In a further particularly preferred embodiment, the crystalline nicotinamide-β-D-ribofuranoside hydrogen tartrate is nicotinamide-β-D-ribofuranoside DL-hydrogen tartrate which may be characterized by a powder X-ray diffraction pattern having peaks substantially as provided in Table 6, below, ±0.2 degrees two theta:

TABLE 6

| Pos. [°2Th.] | Height [cts] | FWHM Left [°2Th.] | d-spacing [Å] | Rel. Int. [%] |
|---|---|---|---|---|
| 8.3072 | 551.28 | 0.2047 | 10.64375 | 1.39 |
| 11.4842 | 12590.46 | 0.0640 | 7.70547 | 31.84 |
| 11.5514 | 14904.11 | 0.1151 | 7.66075 | 37.70 |
| 12.0939 | 5535.53 | 0.1151 | 7.31835 | 14.00 |
| 12.6356 | 9270.40 | 0.1535 | 7.00577 | 23.45 |
| 13.1792 | 7450.29 | 0.1663 | 6.71800 | 18.84 |
| 14.1441 | 345.14 | 0.1535 | 6.26180 | 0.87 |
| 15.3154 | 6761.68 | 0.1535 | 5.78544 | 17.10 |
| 16.2510 | 6902.60 | 0.1663 | 5.45441 | 17.46 |
| 16.6164 | 4425.97 | 0.1407 | 5.33529 | 11.19 |
| 17.0694 | 38995.42 | 0.2047 | 5.19469 | 98.63 |
| 17.3813 | 4647.82 | 0.0512 | 5.10218 | 11.76 |
| 17.6574 | 1047.06 | 0.1023 | 5.02301 | 2.65 |
| 18.2347 | 2589.27 | 0.1407 | 4.86527 | 6.55 |
| 19.1062 | 673.09 | 0.1535 | 4.64527 | 1.70 |
| 19.9124 | 1996.71 | 0.1535 | 4.45898 | 5.05 |

TABLE 6-continued

| Pos. [°2Th.] | Height [cts] | FWHM Left [°2Th.] | d-spacing [Å] | Rel. Int. [%] |
|---|---|---|---|---|
| 20.3072 | 887.20 | 0.1279 | 4.37317 | 2.24 |
| 20.7939 | 1891.47 | 0.1535 | 4.27191 | 4.78 |
| 21.3241 | 10559.20 | 0.1535 | 4.16688 | 26.71 |
| 21.5806 | 21215.64 | 0.1663 | 4.11792 | 53.66 |
| 22.2002 | 22505.15 | 0.1919 | 4.00438 | 56.92 |
| 22.7919 | 39538.58 | 0.1919 | 3.90173 | 100.00 |
| 23.1194 | 12527.96 | 0.1535 | 3.84721 | 31.69 |
| 23.6904 | 23665.39 | 0.1535 | 3.75575 | 59.85 |
| 23.9145 | 29131.82 | 0.1279 | 3.72167 | 73.68 |
| 24.1548 | 9173.54 | 0.0895 | 3.68459 | 23.20 |
| 24.5068 | 12495.64 | 0.1791 | 3.63246 | 31.60 |
| 25.3161 | 1841.17 | 0.1279 | 3.51815 | 4.66 |
| 25.6584 | 7132.62 | 0.1407 | 3.47198 | 18.04 |
| 26.1650 | 7886.89 | 0.1663 | 3.40590 | 19.95 |
| 26.7609 | 3343.45 | 0.1023 | 3.33139 | 8.46 |
| 27.0106 | 3166.41 | 0.1023 | 3.30116 | 8.01 |
| 27.5367 | 7146.89 | 0.1407 | 3.23928 | 18.08 |
| 27.7875 | 11104.30 | 0.1535 | 3.21060 | 28.08 |
| 28.6467 | 3577.53 | 0.1535 | 3.11623 | 9.05 |
| 29.6650 | 8795.23 | 0.1279 | 3.01154 | 22.24 |
| 29.8675 | 7541.81 | 0.1023 | 2.99158 | 19.07 |
| 30.2186 | 1849.66 | 0.1279 | 2.95762 | 4.68 |
| 31.2001 | 4758.17 | 0.1791 | 2.86678 | 12.03 |
| 31.4762 | 3632.98 | 0.0768 | 2.84227 | 9.19 |
| 31.8369 | 1281.77 | 0.1279 | 2.81088 | 3.24 |
| 32.2436 | 301.91 | 0.1535 | 2.77635 | 0.76 |
| 32.8599 | 1056.56 | 0.1535 | 2.72567 | 2.67 |
| 33.3306 | 1490.86 | 0.1023 | 2.68825 | 3.77 |
| 33.6389 | 1842.81 | 0.1791 | 2.66431 | 4.66 |
| 34.4485 | 2040.78 | 0.1791 | 2.60353 | 5.16 |
| 34.7957 | 2063.81 | 0.1279 | 2.57834 | 5.22 |
| 35.1573 | 6826.29 | 0.0936 | 2.55053 | 17.26 |
| 35.2409 | 5684.59 | 0.0768 | 2.54678 | 14.38 |
| 35.5944 | 3446.74 | 0.0768 | 2.52229 | 8.72 |

In a further particularly preferred embodiment, the crystalline nicotinamide-2,3,5-O-triacetyl-β-D-ribofuranoside hydrogen tartrate is nicotinamide-2,3,5-triacetyl-O-β-D-ribofuranoside L-hydrogen tartrate which may be characterized by a powder X-ray diffraction pattern having peaks substantially as provided in Table 7, below, ±0.2 degrees two theta:

TABLE 7

| Pos. [°2Th.] | Height [cts] | FWHM Left [°2Th.] | d-spacing [Å] | Rel. Int. [%] |
|---|---|---|---|---|
| 9.3064 | 2347.46 | 0.0895 | 9.50315 | 3.00 |
| 10.7524 | 54988.21 | 0.2047 | 8.22821 | 70.17 |
| 12.6167 | 7227.54 | 0.1535 | 7.01622 | 9.22 |
| 13.7645 | 49185.18 | 0.2047 | 6.43363 | 62.76 |
| 14.5019 | 23374.03 | 0.2175 | 6.10811 | 29.83 |
| 16.5953 | 8289.38 | 0.2047 | 5.34201 | 10.58 |
| 17.7919 | 10891.17 | 0.1919 | 4.98534 | 13.90 |
| 18.2775 | 39457.79 | 0.2047 | 4.85397 | 50.35 |
| 18.4595 | 15797.39 | 0.0768 | 4.80652 | 20.16 |
| 19.4199 | 30898.77 | 0.1919 | 4.57093 | 39.43 |
| 20.7987 | 74506.22 | 0.2175 | 4.27092 | 95.08 |
| 21.4057 | 29048.75 | 0.1663 | 4.15117 | 37.07 |
| 21.7760 | 78364.38 | 0.2047 | 4.08141 | 100.00 |
| 22.1876 | 17507.69 | 0.1791 | 4.00662 | 22.34 |
| 22.5630 | 5652.40 | 0.1151 | 3.94079 | 7.21 |
| 22.8293 | 7556.27 | 0.1151 | 3.89543 | 9.64 |
| 23.6771 | 36209.59 | 0.1919 | 3.75783 | 46.21 |
| 24.2704 | 5293.40 | 0.1663 | 3.66730 | 6.75 |
| 25.1652 | 13110.92 | 0.1663 | 3.53890 | 16.73 |
| 25.6520 | 29248.77 | 0.1919 | 3.47283 | 37.32 |
| 27.2015 | 3937.84 | 0.1023 | 3.27842 | 5.03 |
| 27.5402 | 17275.90 | 0.1663 | 3.23887 | 22.05 |
| 27.8198 | 12918.63 | 0.0895 | 3.20695 | 16.49 |
| 28.5481 | 970.62 | 0.1279 | 3.12677 | 1.24 |
| 28.8967 | 3057.58 | 0.1279 | 3.08984 | 3.90 |
| 29.1513 | 7076.72 | 0.0640 | 3.06343 | 9.03 |

TABLE 7-continued

| Pos. [°2Th.] | Height [cts] | FWHM Left [°2Th.] | d-spacing [Å] | Rel. Int. [%] |
|---|---|---|---|---|
| 29.6275 | 17107.02 | 0.1407 | 3.01527 | 21.83 |
| 29.8910 | 9269.72 | 0.0895 | 2.98929 | 11.83 |
| 30.2515 | 8260.90 | 0.1535 | 2.95448 | 10.54 |
| 31.2838 | 5141.01 | 0.1919 | 2.85930 | 6.56 |
| 31.9853 | 3594.26 | 0.1023 | 2.79818 | 4.59 |
| 32.1680 | 3037.39 | 0.1791 | 2.78270 | 3.88 |
| 32.7773 | 523.69 | 0.1023 | 2.73235 | 0.67 |
| 33.3139 | 3622.17 | 0.0640 | 2.68956 | 4.62 |
| 33.9915 | 3211.57 | 0.1535 | 2.63748 | 4.10 |
| 34.5275 | 2365.82 | 0.1407 | 2.59776 | 3.02 |
| 35.1433 | 4786.90 | 0.1535 | 2.55363 | 6.11 |
| 35.8273 | 1682.02 | 0.1279 | 2.50643 | 2.15 |
| 36.0780 | 6948.34 | 0.0780 | 2.48753 | 8.87 |
| 36.1635 | 8783.18 | 0.1151 | 2.48390 | 11.21 |
| 36.8265 | 8675.69 | 0.1560 | 2.43867 | 11.07 |
| 37.0069 | 13561.59 | 0.1404 | 2.42720 | 17.31 |
| 37.0983 | 11547.67 | 0.1092 | 2.42744 | 14.74 |
| 37.5976 | 2995.69 | 0.0936 | 2.39041 | 3.82 |
| 37.9266 | 7992.80 | 0.2652 | 2.37042 | 10.20 |
| 38.8868 | 1967.52 | 0.1872 | 2.31408 | 2.51 |
| 39.3599 | 1961.34 | 0.3120 | 2.28734 | 2.50 |
| 40.0431 | 2967.56 | 0.2808 | 2.24988 | 3.79 |
| 41.2033 | 2016.08 | 0.3120 | 2.18917 | 2.57 |
| 41.6658 | 1798.38 | 0.1560 | 2.16593 | 2.29 |

In a further particularly preferred embodiment, the crystalline nicotinamide-2,3,5-O-triacetyl-β-D-ribofuranoside hydrogen tartrate is nicotinamide-2,3,5-triacetyl-O-β-D-ribofuranoside D-hydrogen tartrate which may be characterized by a powder X-ray diffraction pattern having peaks substantially as provided in Table 8, below, ±0.2 degrees two theta:

TABLE 8

| Pos. [°2Th.] | Height [cts] | FWHM Left [°2Th.] | d-spacing [Å] | Rel. Int. [%] |
|---|---|---|---|---|
| 4.7520 | 34825.67 | 0.1279 | 18.59607 | 22.27 |
| 6.8248 | 3649.79 | 0.1023 | 12.95200 | 2.33 |
| 9.3927 | 156411.40 | 0.1407 | 9.41597 | 100.00 |
| 9.8311 | 8959.38 | 0.1151 | 8.99710 | 5.73 |
| 10.5898 | 20049.70 | 0.1279 | 8.35415 | 12.82 |
| 10.8918 | 3604.23 | 0.0768 | 8.12315 | 2.30 |
| 13.5669 | 2632.18 | 0.0768 | 6.52689 | 1.68 |
| 14.0604 | 14165.00 | 0.1535 | 6.29889 | 9.06 |
| 14.8805 | 2477.98 | 0.0768 | 5.95354 | 1.58 |
| 15.4419 | 36385.34 | 0.1407 | 5.73835 | 23.26 |
| 16.2548 | 6914.23 | 0.1023 | 5.45313 | 4.42 |
| 17.1363 | 5280.44 | 0.1535 | 5.17459 | 3.38 |
| 18.3514 | 4827.86 | 0.1023 | 4.83460 | 3.09 |
| 18.7218 | 27898.79 | 0.1407 | 4.73978 | 17.84 |
| 19.3655 | 53967.66 | 0.1535 | 4.58365 | 34.50 |
| 19.6270 | 16569.59 | 0.1023 | 4.52316 | 10.59 |
| 20.3529 | 4564.06 | 0.0895 | 4.36346 | 2.92 |
| 21.1360 | 6828.67 | 0.1279 | 4.20353 | 4.37 |
| 21.3815 | 2953.04 | 0.1023 | 4.15582 | 1.89 |
| 21.7618 | 5095.87 | 0.1535 | 4.08404 | 3.26 |
| 22.4599 | 6736.19 | 0.1279 | 3.95866 | 4.31 |
| 23.0021 | 3986.81 | 0.0895 | 3.86656 | 2.55 |
| 23.2351 | 7330.57 | 0.0768 | 3.82830 | 4.69 |
| 23.4473 | 22811.80 | 0.1279 | 3.79415 | 14.58 |
| 23.8524 | 38132.07 | 0.1535 | 3.73061 | 24.38 |
| 24.1716 | 2985.45 | 0.0512 | 3.68206 | 1.91 |
| 24.5306 | 6250.72 | 0.1407 | 3.62899 | 4.00 |
| 25.0542 | 7291.19 | 0.1279 | 3.55432 | 4.66 |
| 25.6757 | 1515.37 | 0.1023 | 3.46968 | 0.97 |
| 26.3310 | 2183.17 | 0.1151 | 3.38480 | 1.40 |
| 26.9259 | 12871.27 | 0.1535 | 3.31136 | 8.23 |
| 27.2043 | 7721.08 | 0.1279 | 3.27809 | 4.94 |
| 27.7527 | 4341.55 | 0.1023 | 3.21455 | 2.78 |
| 27.9615 | 5727.76 | 0.1023 | 3.19102 | 3.66 |
| 28.2032 | 6203.34 | 0.1151 | 3.16422 | 3.97 |
| 28.6321 | 8480.22 | 0.1151 | 3.11779 | 5.42 |

TABLE 8-continued

| Pos. [°2Th.] | Height [cts] | FWHM Left [°2Th.] | d-spacing [Å] | Rel. Int. [%] |
|---|---|---|---|---|
| 29.1374 | 4096.80 | 0.1151 | 3.06486 | 2.62 |
| 29.5708 | 1219.70 | 0.0768 | 3.02092 | 0.78 |
| 29.9108 | 7245.93 | 0.1151 | 2.98735 | 4.63 |
| 30.4399 | 1297.52 | 0.1151 | 2.93662 | 0.83 |
| 31.0508 | 8262.20 | 0.1407 | 2.88023 | 5.28 |
| 31.9092 | 6516.50 | 0.1407 | 2.80468 | 4.17 |
| 32.4553 | 1065.25 | 0.1279 | 2.75872 | 0.68 |
| 32.8369 | 6234.01 | 0.1151 | 2.72753 | 3.99 |
| 33.1800 | 5520.53 | 0.1279 | 2.70011 | 3.53 |
| 33.4767 | 2168.58 | 0.1023 | 2.67685 | 1.39 |
| 34.3025 | 3153.03 | 0.1151 | 2.61428 | 2.02 |
| 34.5793 | 2022.97 | 0.1407 | 2.59398 | 1.29 |
| 35.1728 | 1308.53 | 0.0895 | 2.55156 | 0.84 |
| 36.3834 | 468.74 | 0.2047 | 2.46939 | 0.30 |

In a further particularly preferred embodiment, the crystalline nicotinamide-β-D-ribofuranoside hydrogen tartrate is anhydrous nicotinamide-β-D-ribofuranoside D-hydrogen tartrate which may be characterized by a powder X-ray diffraction pattern having peaks substantially as provided in Table 9, below, ±0.2 degrees two theta:

TABLE 9

| Pos. [°2Th.] | Height [cts] | FWHM Left [°2Th.] | d-spacing [Å] | Rel. Int. [%] |
|---|---|---|---|---|
| 8.2867 | 1565.03 | 0.1279 | 10.67015 | 2.10 |
| 11.5441 | 5477.05 | 0.1663 | 7.66563 | 7.34 |
| 12.8809 | 19026.31 | 0.1919 | 6.87292 | 25.50 |
| 13.6583 | 2145.15 | 0.2047 | 6.48342 | 2.87 |
| 14.7982 | 2238.27 | 0.2047 | 5.98644 | 3.00 |
| 16.3923 | 18852.04 | 0.1663 | 5.40772 | 25.26 |
| 17.4939 | 31734.04 | 0.1791 | 5.06958 | 42.53 |
| 18.2961 | 447.64 | 0.1279 | 4.84910 | 0.60 |
| 19.6742 | 6616.60 | 0.2814 | 4.51243 | 8.87 |
| 20.4519 | 3327.08 | 0.1535 | 4.34256 | 4.46 |
| 21.3667 | 74623.20 | 0.1919 | 4.15865 | 100.00 |
| 22.2026 | 58527.36 | 0.1919 | 4.00395 | 78.43 |
| 22.9236 | 1946.12 | 0.1535 | 3.87962 | 2.61 |
| 23.3038 | 1293.31 | 0.1023 | 3.81718 | 1.73 |
| 24.1005 | 10296.35 | 0.1535 | 3.69276 | 13.80 |
| 24.3711 | 7580.65 | 0.1535 | 3.65237 | 10.16 |
| 25.0633 | 12509.80 | 0.1535 | 3.55305 | 16.76 |
| 26.1075 | 13375.49 | 0.1663 | 3.41327 | 17.92 |
| 27.1046 | 4134.24 | 0.1535 | 3.28992 | 5.54 |
| 27.3697 | 5451.44 | 0.1023 | 3.25865 | 7.31 |
| 27.6019 | 4053.73 | 0.1023 | 3.23177 | 5.43 |
| 28.3123 | 9045.58 | 0.1535 | 3.15228 | 12.12 |
| 28.7376 | 2770.85 | 0.1791 | 3.10447 | 3.71 |
| 29.7420 | 4272.59 | 0.1151 | 3.00392 | 5.73 |
| 30.2505 | 2903.11 | 0.2303 | 2.95457 | 3.89 |
| 30.6625 | 1476.96 | 0.1791 | 2.91581 | 1.98 |
| 31.8526 | 3847.53 | 0.1151 | 2.80953 | 5.16 |
| 32.3522 | 1209.36 | 0.2047 | 2.76727 | 1.62 |
| 33.2255 | 6634.29 | 0.1407 | 2.69651 | 8.89 |
| 33.4595 | 2216.67 | 0.1023 | 2.67819 | 2.97 |
| 33.9924 | 5402.04 | 0.1279 | 2.63741 | 7.24 |
| 34.5081 | 725.11 | 0.1279 | 2.59917 | 0.97 |
| 34.8645 | 1193.46 | 0.1791 | 2.57341 | 1.60 |
| 35.3079 | 2701.51 | 0.1535 | 2.54210 | 3.62 |
| 35.5426 | 2210.45 | 0.1279 | 2.52586 | 2.96 |
| 36.3433 | 3310.00 | 0.1407 | 2.47202 | 4.44 |
| 36.8835 | 6123.57 | 0.1535 | 2.43705 | 8.21 |
| 37.7104 | 1917.12 | 0.1023 | 2.38549 | 2.57 |
| 38.0440 | 2230.62 | 0.1279 | 2.31272 | 2.99 |
| 39.2338 | 2324.44 | 0.0768 | 2.29630 | 3.11 |
| 39.8024 | 4022.79 | 0.1151 | 2.25990 | 5.39 |
| 40.5627 | 1485.94 | 0.1791 | 2.22409 | 1.99 |
| 41.6641 | 814.42 | 0.1023 | 2.16781 | 1.09 |
| 41.0184 | 1443.54 | 0.1535 | 2.15525 | 1.93 |

TABLE 9-continued

| Pos. [°2Th.] | Height [cts] | FWHM Left [°2Th.] | d-spacing [Å] | Rel. Int. [%] |
|---|---|---|---|---|
| 42.5626 | 2097.08 | 0.1791 | 2.12410 | 2.81 |
| 43.3574 | 415.83 | 0.1535 | 2.08699 | 0.56 |
| 44.0950 | 235.65 | 0.3070 | 2.05378 | 0.32 |

Figure 2:
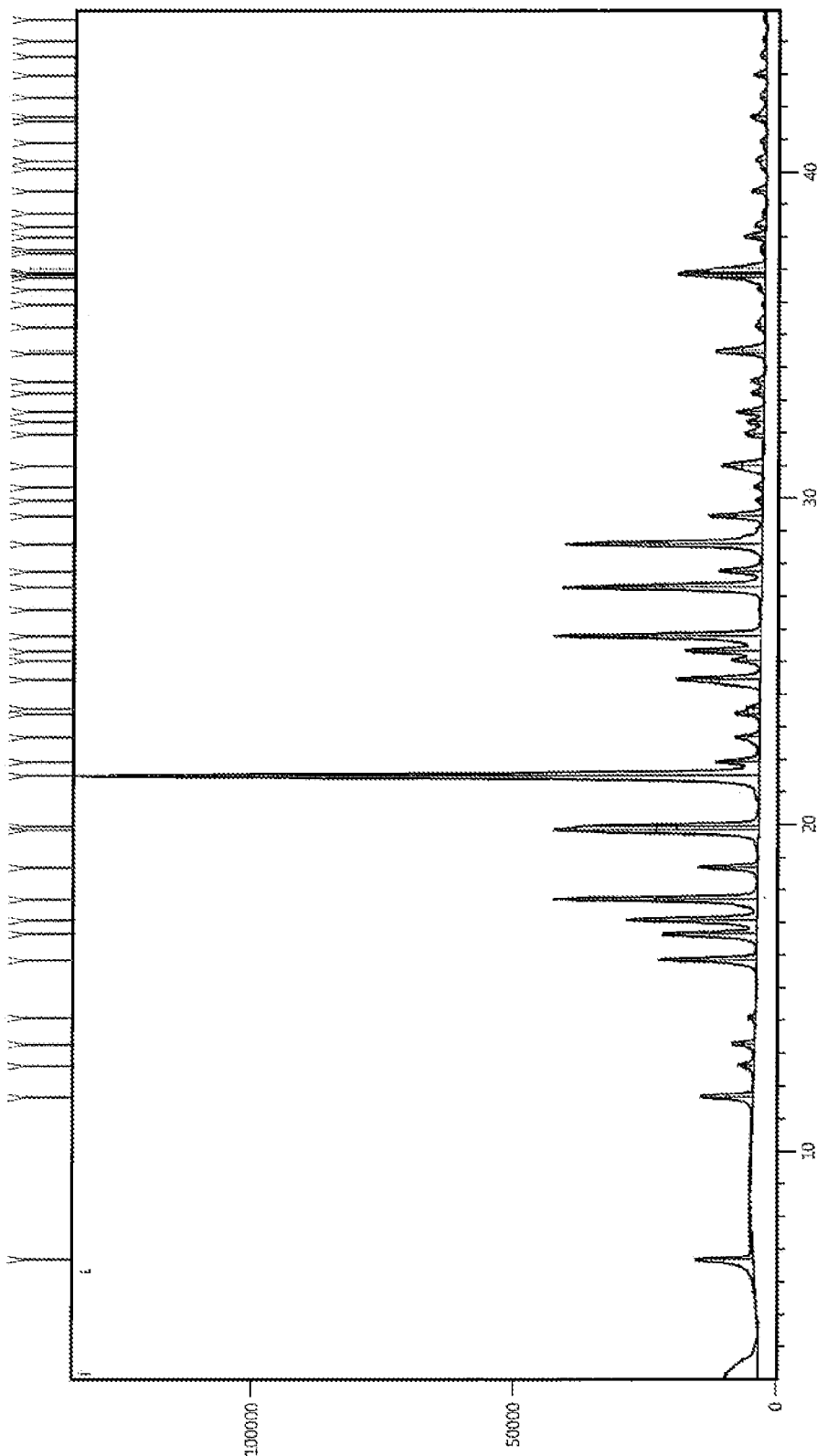
FIG. 2 shows a powder X-ray pattern of crystalline nicotinamide-β-D-ribofuranoside L-hydrogen malate.
Figure 3:
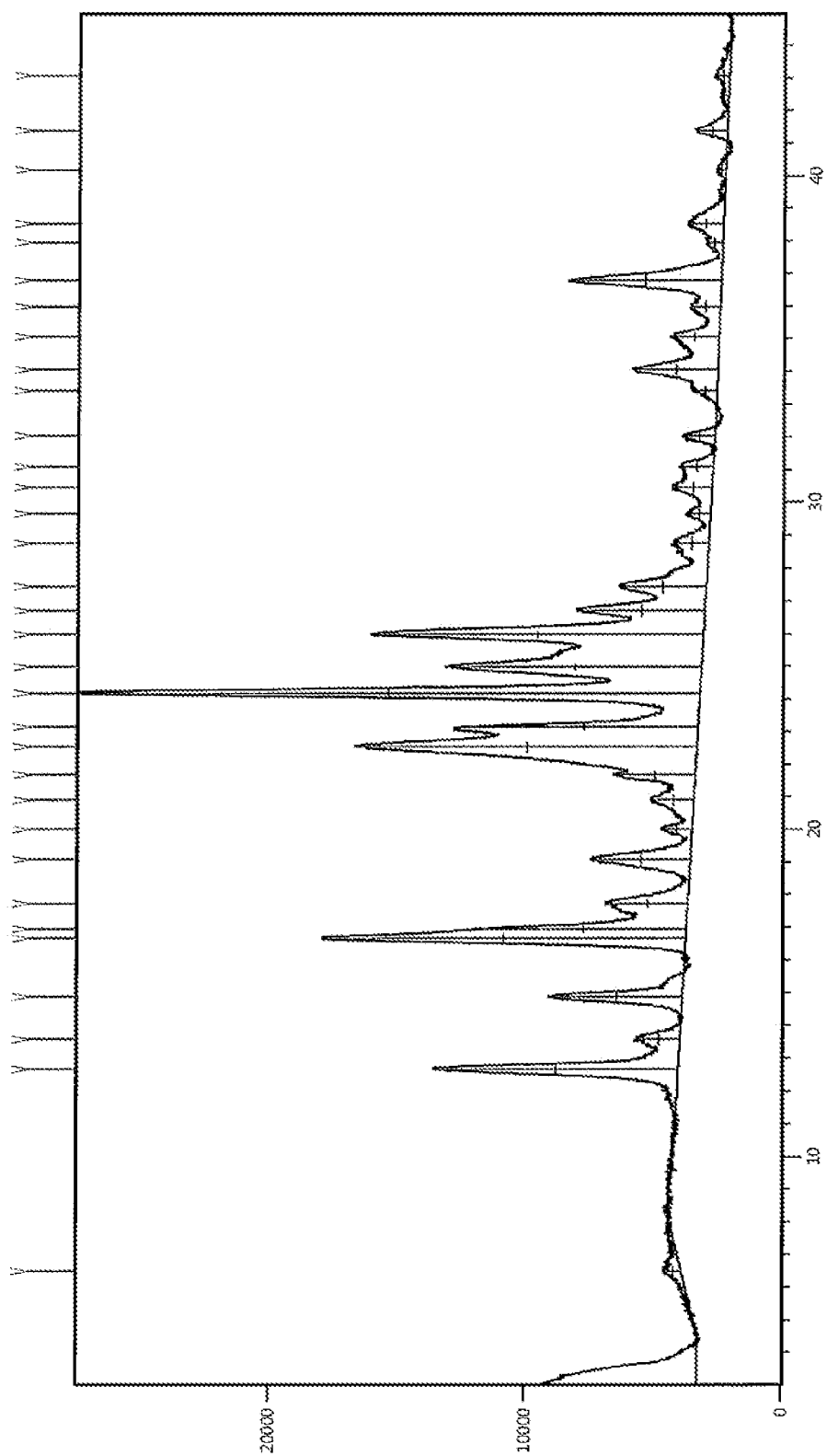
FIG. 3 shows a powder X-ray pattern of crystalline nicotinamide-β-D-ribofuranoside DL-hydrogen malate.
Figure 4:
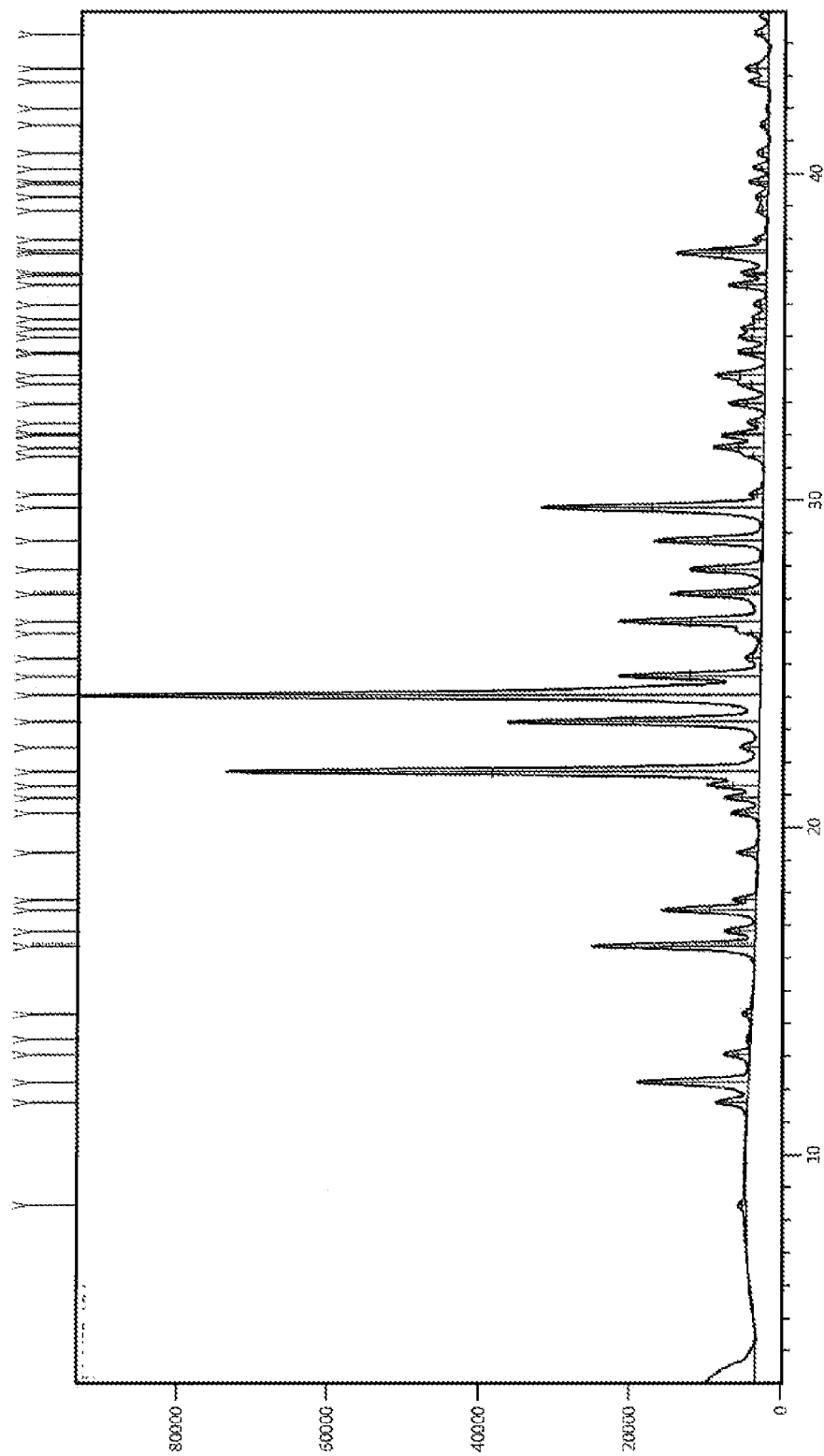
FIG. 4 shows a powder X-ray pattern of crystalline nicotinamide-β-D-ribofuranoside D-hydrogen tartrate monohydrate.
Figure 5:
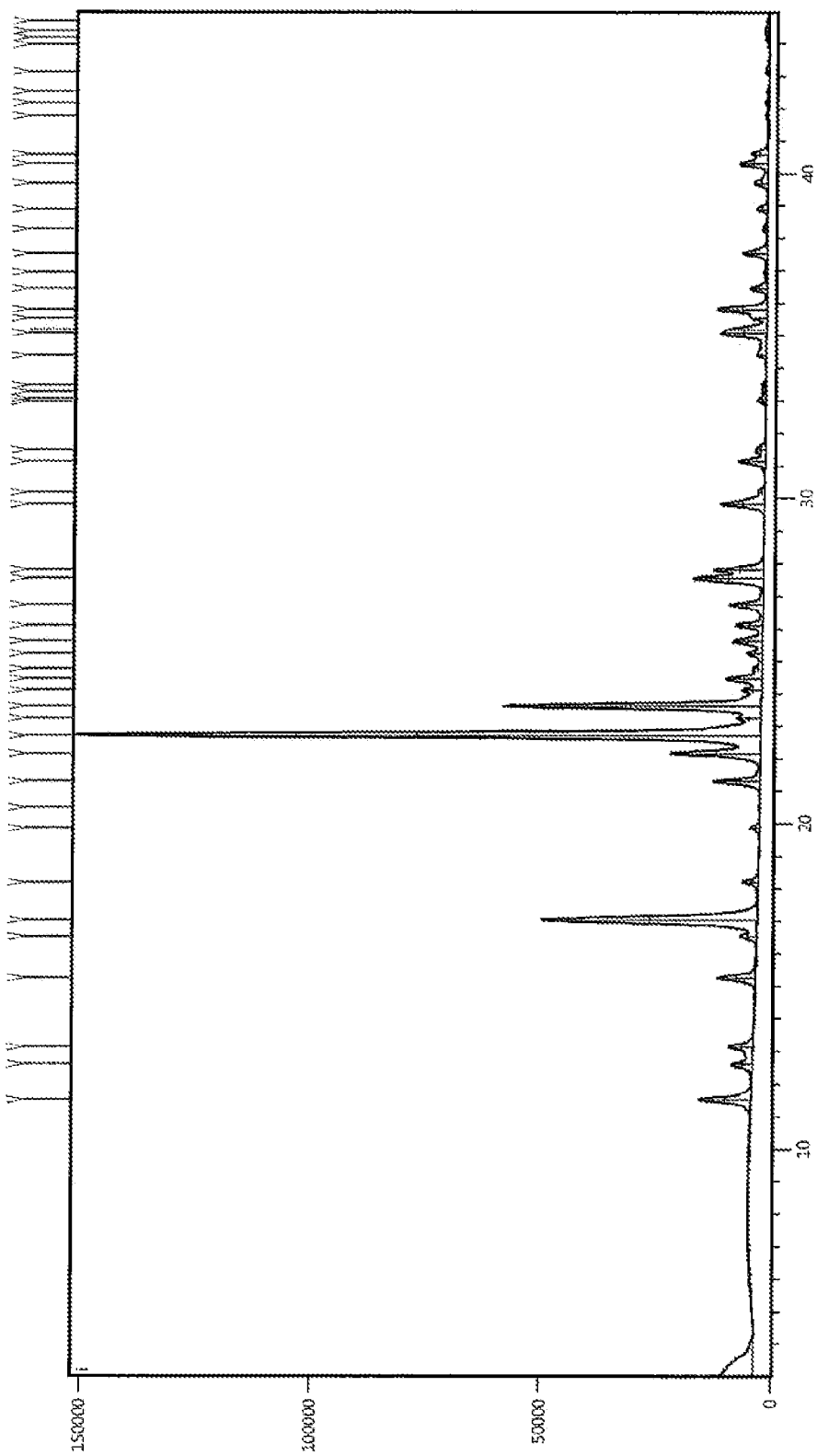
FIG. 5 shows a powder X-ray pattern of crystalline nicotinamide-β-D-ribofuranoside L-hydrogen tartrate.
Figure 6:
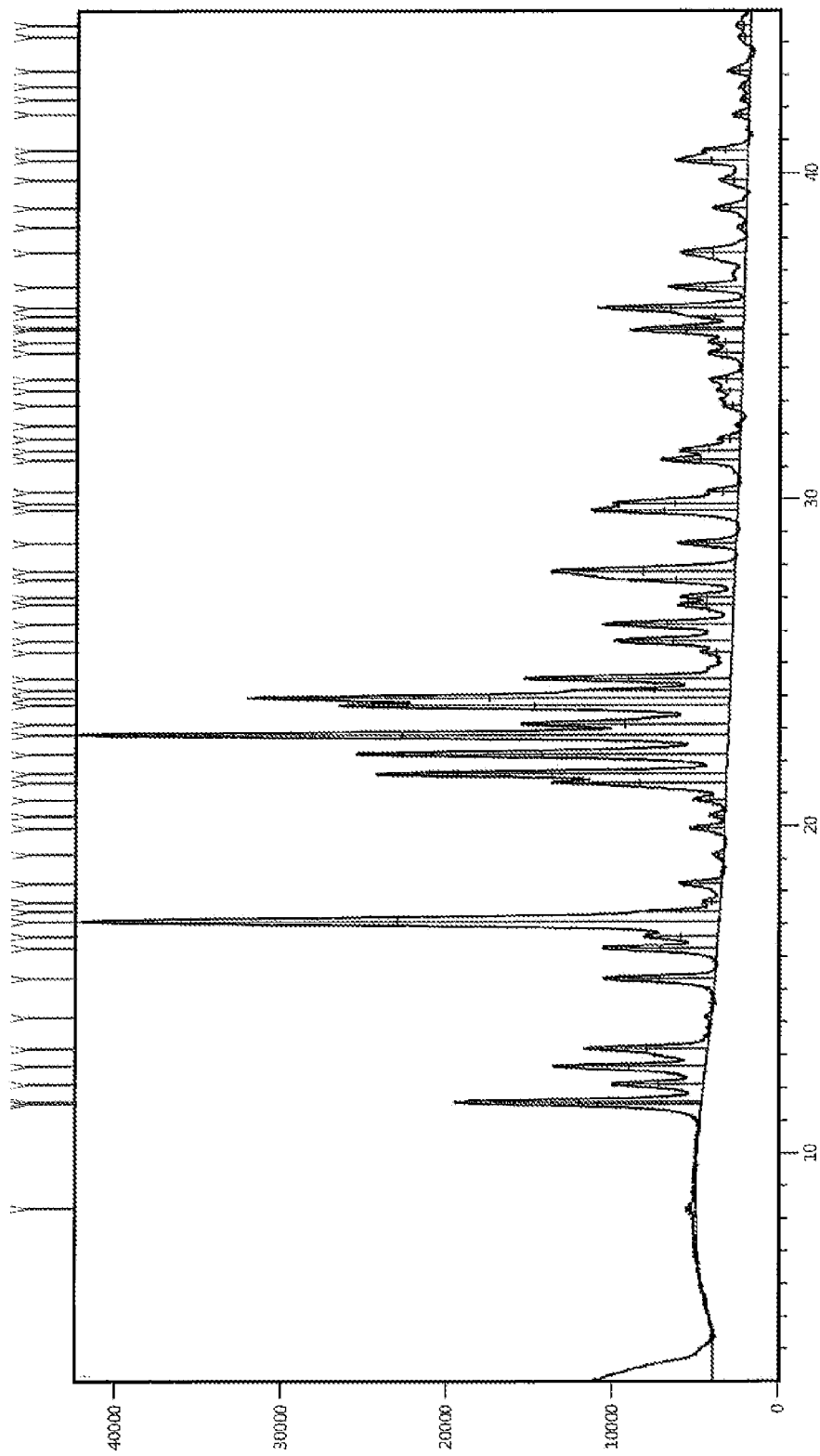
FIG. 6 shows a powder X-ray pattern of crystalline nicotinamide-β-D-ribofuranoside DL-hydrogen tartrate.
Figure 7:
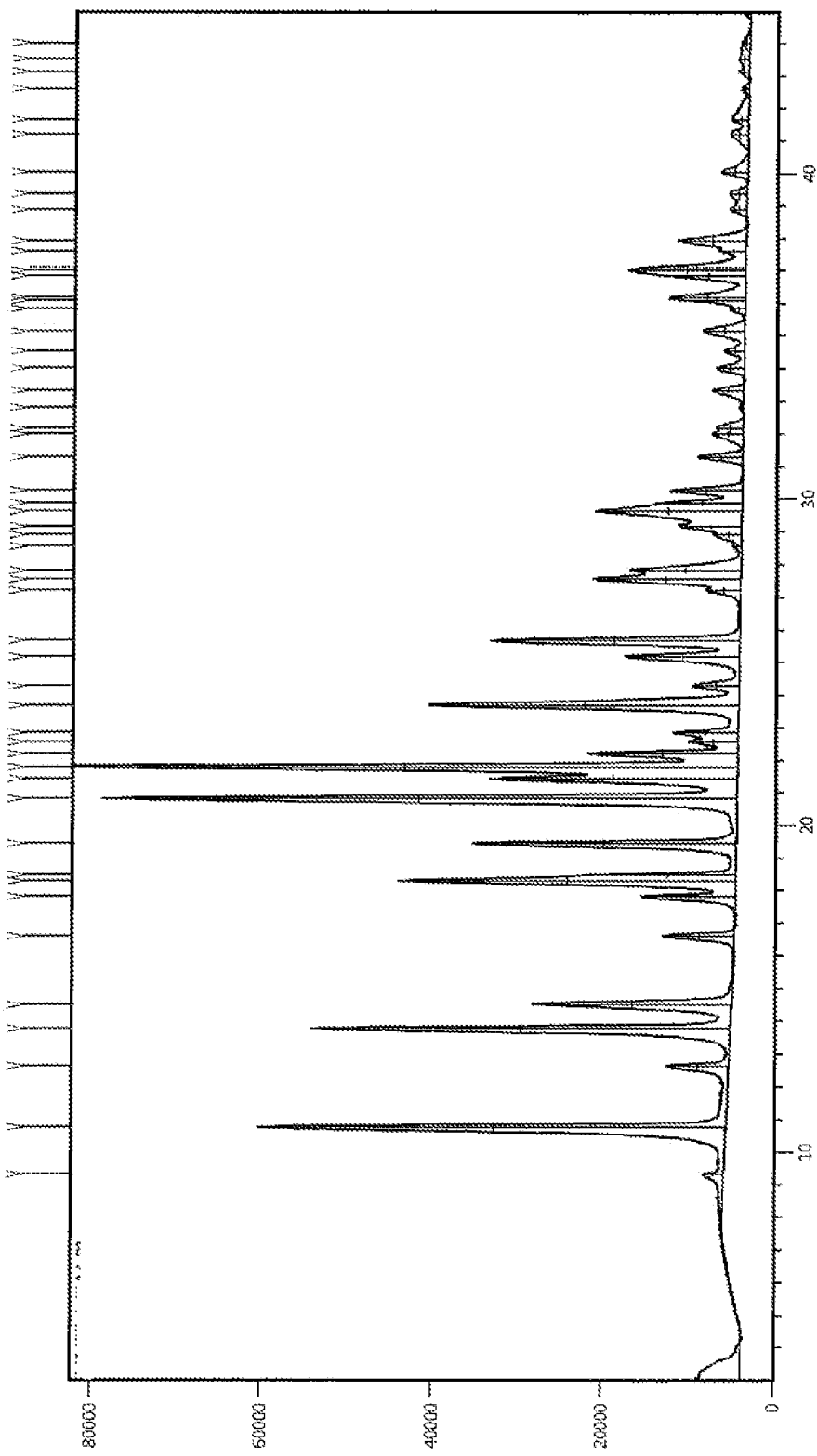
FIG. 7 shows a powder X-ray pattern of crystalline nicotinamide-2,3,5-O-triacetyl-β-D-ribofuranoside L-hydrogen tartrate.
Figure 8:
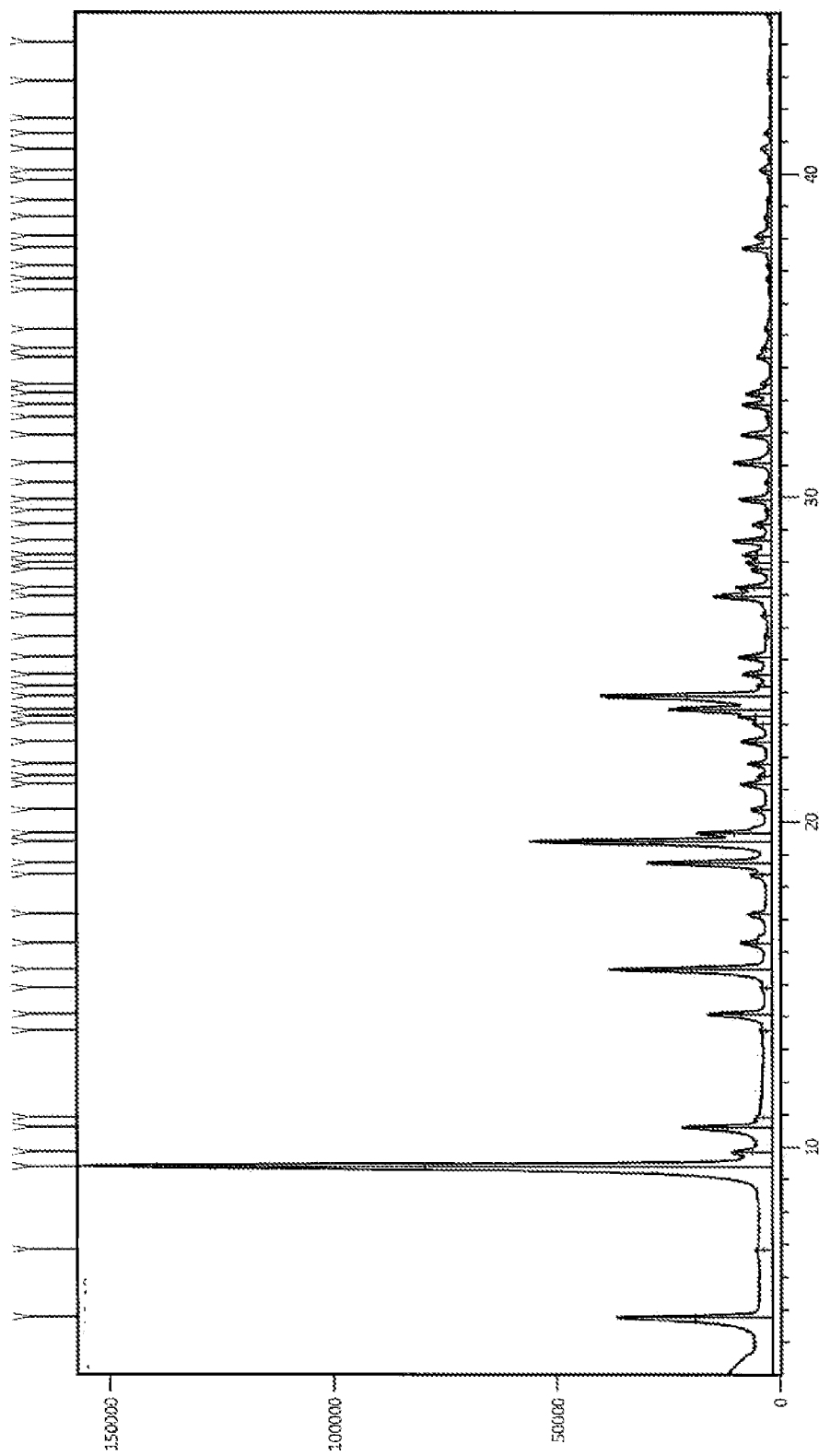
FIG. 8 shows a powder X-ray pattern of crystalline nicotinamide-2,3,5-O-triacetyl-β-D-ribofuranoside D-hydrogen tartrate.
Figure 9:
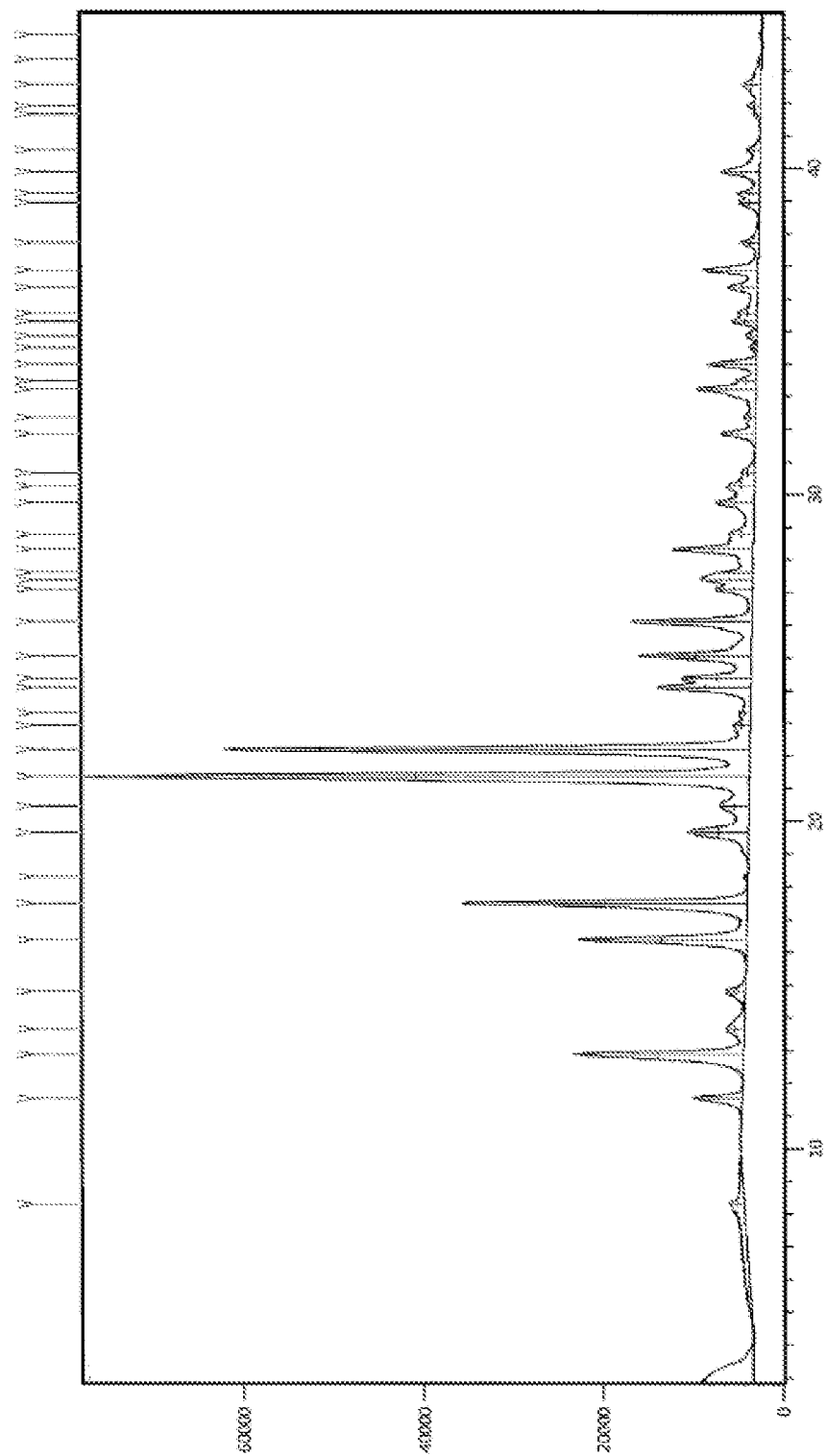
FIG. 9 shows a powder X-ray pattern of crystalline anhydrous nicotinamide-β-D-ribofuranoside D-hydrogen tartrate.

Accordingly, in particularly preferred embodiments, the invention relates to crystalline nicotinamide-β-D-ribofuranoside salts selected from the group consisting of:
  nicotinamide-β-D-ribofuranoside D-hydrogen malate characterized by a powder X-ray diffraction pattern as defined in FIG. 1;
  nicotinamide-β-D-ribofuranoside L-hydrogen malate characterized by a powder X-ray diffraction pattern as defined in FIG. 2;
  nicotinamide-β-D-ribofuranoside DL-hydrogen malate characterized by a powder X-ray diffraction pattern as defined in FIG. 3;
  nicotinamide-β-D-ribofuranoside D-hydrogen tartrate monohydrate characterized by a powder X-ray diffraction pattern as defined in FIG. 4;
  nicotinamide-β-D-ribofuranoside L-hydrogen tartrate characterized by a powder X-ray diffraction pattern as defined in FIG. 5;
  nicotinamide-β-D-ribofuranoside DL-hydrogen tartrate characterized by a powder X-ray diffraction pattern as defined in FIG. 6;
  nicotinamide-2,3,5-O-triacetyl-β-D-ribofuranoside L-hydrogen tartrate characterized by a powder X-ray diffraction pattern as defined in FIG. 7;
  nicotinamide-2,3,5-O-triacetyl-β-D-ribofuranoside D-hydrogen tartrate characterized by a powder X-ray diffraction pattern as defined in FIG. 8;
  anhydrous nicotinamide-β-D-ribofuranoside D-hydrogen tartrate characterized by a powder X-ray diffraction pattern as defined in FIG. 9.

In another embodiment of the fourth aspect, the invention relates to a nicotinamide-β-D-ribofuranoside salt obtainable by a method as defined in any one of the embodiments of the first or second aspect.

Fifth Aspect: Nutritional Supplement

According to a fifth aspect, the invention relates to a nutritional supplement comprising a nicotinamide-β-D-ribofuranoside salt obtained according to a method as defined in the first or second aspect or comprising a nicotinamide-β-D-ribofuranoside salt as defined in the fourth aspect.

Suitable methods for making such nutritional supplement comprising a nicotinamide-β-D-ribofuranoside salt are known in the art or may be prepared analogously to such known methods.

Sixth Aspect: Pharmaceutical Composition

According to a sixth aspect, the invention relates to a pharmaceutical composition comprising a nicotinamide-β-D-ribofuranoside salt obtained according to a method as defined in the first or second aspect or comprising a nicotinamide-β-D-ribofuranoside salt as defined in the fourth aspect.

The pharmaceutical composition may be used in the prevention or treatment of diseases or conditions associated with the nicotinamide riboside kinase pathway or other pathways of NAD$^+$ biosynthesis. These pathways are known in the art.

Seventh Aspect: Use of the Compounds Defined in the Fourth Aspect as Starting Material for a Chemical Synthesis The crystalline compounds as defined in the fourth aspect, due to their purity, and ease of access may serve as starting material for making other nicotinamide-β-D-ribofuranoside salts, e.g. the commercially available chloride, or related compounds, i.e. they may be used as starting materials in a chemical synthesis.

According to a seventh aspect, the invention relates to a method of performing a chemical synthesis, comprising step (A):

(A) providing a nicotinamide-β-D-ribofuranoside salt obtained by the method as defined in the first, second or third aspect, or providing a compound defined in the fourth aspect.

Eighth Aspect: Preparation of nicotinamide-2,3,5-tri-O-acyl-β-D-ribofuranoside Triflate or nicotinamide-2,3,5-tri-O-acyl-β-D-ribofuranoside Chloride, Bromide, Iodide, Nonaflate, Fluorosulfonate or Perchlorate The inventors have further modified the method developed by Tanimori as disclosed in the third aspect. It was hitherto believed that this known method requires a tremendous excess of 7.3 equivalents TMSOTf related to one equivalent tetra-O-acyl-β-D-ribofuranose in order to form nicotinamide-2,3,5-tri-O-acyl-β-D-ribofuranoside triflate being sufficiently pure for subsequent reactions.

The inventors of the present invention unexpectedly discovered that the use of much less TMSOTf resulted in a product having a higher purity compared to the product obtained with the tremendous molar excess of TMSOTf. This is particularly advantageous under economic aspects.

Accordingly, in said eighth aspect, the invention relates to a method of making a nicotinamide-2,3,5-tri-O-acyl-β-D-ribofuranoside triflate, the method comprising step (A):

(A) reacting nicotinamide with tetra-O-acyl-β-D-ribofuranose in presence of 0.9 to 1.5 mole equivalents TMSOTf related to one mole tetra-O-acyl-β-D-ribofuranose.

Preferably, 1.0 to 1.5 mole equivalent TMSOTf are used, more preferably 1.0 to 1.3 mole equivalent, still more preferred 1.0 to 1.2 mole equivalent.

Preferably, acetonitrile is used as solvent.

Preferably, the reaction is carried out in a temperature range of from 10 to 40° C., more preferably 20 to 30° C.

Nicotinamide-2,3,5-tri-O-acyl-β-D-ribofuranoside triflate may be obtained after removing the solvent as amorphous foam.

The acyl groups may then be cleaved according to known methods to afford the nicotinamide-β-D-ribofuranoside triflate.

Both the acylated product as well as the deacylated product may be used in the respective methods according to the invention as defined in the first, the second and the third aspect.

In one embodiment, nicotinamide-2,3,5-tri-O-acyl-β-D-ribofuranoside triflate is not isolated prior to salt metathesis or prior to deacylation.

The iodide may be prepared in an analogous manner. Accordingly, in this aspect, the invention relates to a method of making a nicotinamide-2,3,5-tri-O-acyl-β-D-ribofuranoside iodide, the method comprising step (A):

(A) reacting nicotinamide with tetra-O-acyl-β-D-ribofuranose in presence of 0.9 to 1.5 mole equivalents TMSI related to one mole tetra-O-acyl-β-D-ribofuranose.

Preferably, the reaction is carried out in a temperature range of from 10 to 50° C., more preferably 20 to 40° C.

This reaction may also be extended to the preparation of the bromide, chloride, nonaflate, fluorosulfonate and perchlorate. Accordingly, in one embodiment, this aspect also relates to a method of making a nicotinamide-2,3,5-tri-O-acyl-β-D-ribofuranoside bromide, chloride, nonaflate, fluorosulfonate or perchlorate, the method comprising step (A):

(A) reacting nicotinamide with tetra-O-acyl-β-D-ribofuranose in presence of 0.9 to 1.5 mole equivalents TMSBr, TMSCl, TMSOSO$_2$C$_4$F$_9$, TMSOSO$_2$F or TMSOClO$_3$ related to one mole tetra-O-acyl-β-D-ribofuranose.

The synthesis of the iodide is particularly preferred due to high yield and purity of the formed product and economic advantages.

Ninth Aspect: nicotinamide-β-D-ribofuranoside Iodide, Nonafluorobutanesulfonate, Fluorosulfonate, Perchlorate, nicotinamide-2,3,5-tri-O-acyl-β-D-ribofuranoside Iodide, Nonafluorobutanesulfonate, Fluorosulfonate, Perchlorate According to the ninth aspect, the invention relates to nicotinamide-β-D-ribofuranoside iodide, nonafluorobutanesulfonate, fluorosulfonate or perchlorate of formula

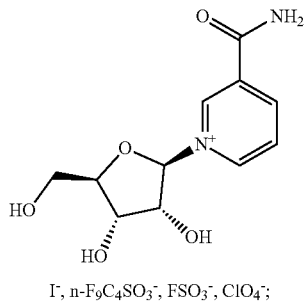 [SMILES: NC(=O)c1ccc[n+]([C@@H]2O[C@H](CO)[C@@H](O)[C@H]2O)c1]

I$^-$, n-F$_9$C$_4$SO$_3^-$, FSO$_3^-$, ClO$_4^-$;

and nicotinamide-2,3,5-tri-O-acyl-β-D-ribofuranoside iodide, nonafluorobutanesulfonate, fluorosulfonate or perchlorate of formula

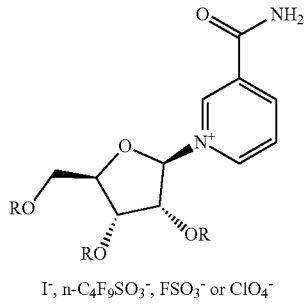

I$^-$, n-C$_4$F$_9$SO$_3^-$, FSO$_3^-$ or ClO$_4^-$ wherein R is an acyl group independently selected from alkyl carbonyl, aryl carbonyl and heteroaryl carbonyl, preferably from C$_{1-10}$ alkyl carbonyl and benzoyl, and is more preferably acetyl, and wherein R is optionally independently substituted with one or more substituents selected from: $C_{1-6}$ alkyl, $C_{1-6}$ alkoxy, $C_{1-6}$ thioalkyl, halogen, nitro, cyano, $NH(C_{1-6}$ alkyl), $N(C_{1-6}$ alkyl)$_2$, and $SO_2N(C_{1-6}$ alkyl)$_2$; preferably wherein R is acetyl.

In another aspect of the invention, nicotinamide used in the synthesis according to the invention as in steps (X) and (Y) as defined in the first aspect and second aspect is used in the form of a precursor, namely in the form of a nicotinic acid ester.

In one embodiment, the ester moiety is selected from $C_{1-10}$ alkoxy which can be branched or unbranched or cyclic. In another embodiment, the ester moiety is phenoxy, optionally substituted. In another embodiment, the ester moiety is benzyloxy, optionally substituted. Herein, the term "optionally substituted" refers to $C_{1-6}$ alkyl, $C_{1-6}$ alkoxy, $C_{1-6}$ thioalkyl, halogen, nitro, cyano, $NH(C_{1-6}$ alkyl), $N(C_{1-6}$ alkyl)$_2$, and $SO_2N(C_{1-6}$ alkyl)$_2$.

Subsequently, the respective compounds bearing a nicotinic acid ester moiety may be subjected to salt metathesis as described above.

Finally, the nicotinic ester moiety of the respective compounds is transferred with ammonia into a nicotinamide moiety.

In another aspect, the invention relates to a method of making a second nicotinamide-β-D-ribofuranoside salt from a first nicotinamide-β-D-ribofuranoside salt or a second nicotinamide-2,3,5-tri-O-acyl-β-D-ribofuranoside salt from a first nicotinamide-2,3,5-tri-O-acyl-β-D-ribofuranoside salt, comprising steps (A1) and (A2):

(A1) reacting $NH_3$ or $NR^1H_2$ or $NR^1R^2H$ or $NR^1R^2R^3$ or $[NR^1R^2R^3R^4]OH$ with an acid to afford an ammonium salt, wherein $R^1$, $R^2$, $R^3$ and $R^4$ are independently selected from $C_{1-12}$ alkyl and aryl, optionally substituted.

(A2) reacting the first nicotinamide-β-D-ribofuranoside salt or the first nicotinamide-2,3,5-tri-O-acyl-β-D-ribofuranoside salt with the ammonium salt from step (A1) to perform salt metathesis comprising counter-ion exchange to afford the second nicotinamide-β-D-ribofuranoside salt or the second nicotinamide-2,3,5-tri-O-acyl-β-D-ribofuranoside salt.

In a preferred embodiment, $NR^1R^2R^3$ or $[NR^1R^2R^3R^4]OH$ is used in step (A1).

The acetyl residue used in the nicotinamide-2,3,5-tri-O-acyl-β-D-ribofuranoside salt is defined above.

Preferably, step (A2) is performed in a solvent comprising an alcohol selected from the group consisting of methanol, ethanol, a propanol or a butanol or a mixture of two or more thereof, optionally the solvent or the alcohol comprising water; or the solvent is selected from the group consisting of methanol, ethanol, a propanol or a butanol or a mixture of two or more thereof, optionally comprising water.

In another aspect, the invention relates to the use of an ammonium salt comprising $NH_4^+$ or $NR^1H_3^+$ or $NR^1R^2H_2^+$ or $NR^1R^2R^3H^+$ or $[NR^1R^2R^3R^4]^+$, wherein $R^1$, $R^2$, $R^3$ and $R^4$ are independently selected from $C_{1-12}$ alkyl and aryl, optionally substituted, in a salt metathesis reaction.

Preferably, a nicotinamide-β-D-ribofuranoside salt or a nicotinamide-2,3,5-tri-O-acyl-β-D-ribofuranoside salt is subjected to salt metathesis.

The acetyl residue used in the nicotinamide-2,3,5-tri-O-acyl-β-D-ribofuranoside salt is defined above.

Preferably, the salt metathesis reaction is performed in a solvent comprising an alcohol selected from the group consisting of methanol, ethanol, a propanol or a butanol or a mixture of two or more thereof, optionally the solvent or the alcohol comprising water; or the solvent is selected from the group consisting of methanol, ethanol, a propanol or a butanol or a mixture of two or more thereof, optionally comprising water.

The following Examples further illustrate the present invention.

EXAMPLES

Example 1: Preparation of nicotinamide-2,3,5-tri-O-acetyl-β-D-ribofuranoside Bromide Used as Starting Salt in Step (A) of the Method According to the Second or Third Aspect 274 g β-D-ribofuranose 1,2,3,5-tetraacetate were dissolved in 274 ml acetonitrile. 180 ml of hydrogen bromide in glacial acetic acid (concentration 33%) were added to the stirred solution while keeping the temperature between 0° C. and 5° C. Stirring was continued for further 15 minutes. 41 g of nicotinamide was added while stirring for another 15 minutes. A hot (70° C.) solution of 96 g nicotinamide in 700 ml acetonitrile was then added whereupon the mixture was cooled to about 0° C. to 5° C. Stirring was continued for 15 h, followed by filtration of the formed suspension. The filtrate was subjected to distillation. The obtained oily residue was diluted with acetone, resulting in crystallization of the title product. The title product was filtered and dried to give 167 g (43% yield) of an almost colorless product; Mp: 133-134° C.

$^1$H-NMR (400 MHz, DMSO-d6): 2.09 (s, 6H), 2.13 (s, 3H) 4.45 (m, 2H, H5'), 4.69 (m, 1H, H4'), 5.43 (t, 1H, H3'), 5.62 (dd, 1H, H2'), 6.69 (d, 1H, H1'), 8.23 (s, 1H, NH), 8.41 (dd, 1H, H5), 8.74 (s, 1H, NH), 9.13 (d, 1H, H4), 9.28 (d, 1H, H6), 9.49 (s, 1H, H2);

$^{13}$C-NMR (100 MHz, DMSO-d6): 20.3, 20.4, 20.5, 62.1 (C5'), 68.7 (C3'), 75.3 (C2'), 81.8 (C4'), 97.2 (C1'), 128.1 (C5), 133.9 (C3), 141.2 (C2), 143.1 (C6), 145.5 (C4), 162.7 (CONH2), 169.2, 169.4, 170.1

Example 2: Preparation of nicotinamide-β-D-ribofuranoside Bromide Used as Starting Salt in Step (A) in the Method According to the First Aspect 167 g of the product obtained in Example 1 were dissolved in 870 ml methanol. 135 ml of hydrogen bromide in acetic acid (concentration 33%) were then added to the stirred solution while keeping the temperature between 5° C. to 10° C. The resulting mixture was stirred for two days at 20° C. wherein the product started crystallizing. The formed crystals were filtered off, washed with isopropanol and dried. The title compound was obtained in a yield of 77 g (63%) as a pale yellow crystalline powder; Mp: 118-119° C.

$^1$H-NMR (400 MHz, D$_2$O): 3.83 (dd, 1H, H5'), 3.98 (dd, 1H, H5'), 4.29 (t, 1H, H3'), 4.39-4.48 (m, 2H, H4', H2'), 6.18 (d, 1H, H1'), 8.22 (t, 1H, H5), 8.91 (d, 1H, H4), 9.20 (d, 1H, H6), 9.52 (s, 1H, H2);

$^{13}$C-NMR (100 MHz, D$_2$O): 60.0 (C5'), 69.5 (C3'), 77.2 (C2'), 87.5 (C4'), 99.7 (C1'), 128.3 (C5), 133.7 (C3), 140.2 (C2), 142.5 (C6), 145.5 (C4), 165.6 (CONH2).

Example 3: Preparation of nicotinamide-β-D-ribofuranoside L-hydrogen Tartrate From nicotinamide-β-D-ribofuranoside Bromide Using Various Ammonium L-hydrogen Tartrate Salts for Salt Metathesis

Example 3a: Use of TEA•L-hydrogen Tartrate 3.90 g of L-tartaric acid (26.0 mMol) were dissolved in 10 ml methanol with stirring. The colorless solution was cooled in an ice bath and 3.64 ml triethylamine (26.1 mMol) added. The pH of the slightly yellowish solution was around 4-4.5. In this manner 15 ml of a 1.73 molar solution of TEA•L-hydrogen tartrate was prepared.

5.8 g nicotinamide-β-D-ribofuranoside bromide (NR•Br) were dissolved with stirring in 3.5 ml water at room temperature. 10 ml methanol were added. 10 ml of the above prepared solution of triethylammonium L-hydrogen tartrate were added to the clear colorless solution. White product starts precipitating.

The suspension was stirred for a further hour at room temperature. The product was filtered, washed with methanol and dried in vacuum at 35° C. 6.62 g (95%) of a white, crystalline powder were obtained; mp: 129-130° C.; IC: Residual bromide 0.20%. The solid may be recrystallized from aqueous methanol, if desired.

$^1$H-NMR (400 MHz, D$_2$O): 3.82 (dd, 1H, H5'), 3.97 (dd, 1H, H5'), 4.28 (t, 1H, H3'), 4.38-4.45 (m, 2H, H4', H2'), 4.41 (s, 2H, 2×CHOH, H-tartrate), 6.17 (d, 1H, H1'), 8.20 (t, 1H, H5), 8.90 (d, 1H, H4), 9.19 (d, 1H, H6), 9.52 (s, 1H, H2). Impurities: <1 mol % nicotinamide; 1.2 mol % TEA salt: 1.19 (t, 9H), 3.11 (q, 6H). Solvents: 7.3 mol % methanol: 3.25 (s, 3H).

$^{13}$C-NMR (100 MHz, D$_2$O): 60.2 (C5'), 69.7 (C3'), 72.8 (2×CHOH, H-tartrate), 77.4 (C2'), 87.6 (C4'), 99.9 (C1'), 128.4 (C5), 133.9 (C3), 140.4 (C2), 142.6 (C6), 145.6 (C4), 165.8 (CONH2), 176.3 (2×COO, H-tartrate). Impurity: 8.2, 46.6 (TEA). Solvents: 48.9 (methanol).

XRD: crystalline (FIG. 5)

Example 3b: Use of TBA•L-hydrogen Tartrate 3.90 g of L-tartaric acid (26.0 mMol) were dissolved in 10 ml methanol with stirring. The colorless solution was cooled in an ice bath and 6.3 ml tributylamine (26.0 mMol) added. The pH of the slightly yellowish solution was around 4. In this manner 17.5 ml of a 1.53 molar solution of tributylammonium L-hydrogen tartrate was prepared.

5.80 g nicotinamide-β-D-ribofuranoside bromide were dissolved with stirring in 3.5 ml water at room temperature. 10 ml methanol were added. 11.1 ml of the above prepared solution of tributylammonium L-hydrogentartrate were added to the clear colorless solution. White product immediately starts crystallizing.

The suspension was stirred for a further hour at room temperature. The product was filtered, washed with methanol and dried in vacuum at 35° C. 6.37 g (91%) of a white, crystalline powder were obtained; mp: 128° C.; IC: Residual bromide 0.62%.

Impurities (NMR): <1 mol % nicotinamide, 2.7 mol % TBA salt: 0.84 (t, 9H), 1.28 (m, 6H), 1.58 (m, 6H), 3.04 (q, 6H); solvents: 3.7 mol % methanol: 3.25 (s, 3H).

Example 3c: Use of Tetrabutylammonium•L-hydrogen Tartrate 3.90 g of L-tartaric acid (26.0 mMol) were dissolved in 10 ml methanol with stirring. The colorless solution was cooled in an ice bath and 17.0 ml of a 40% solution of tetrabutylammonium hydroxide in water (26.0 mMol) were added. The pH of the slightly yellowish solution was around 4. In this manner 29 ml of a 0.9 molar solution of tetrabutylammonium L-hydrogen tartrate was prepared.

5.80 g nicotinamide-β-D-ribofuranoside bromide were dissolved with stirring in 3.5 ml water at room temperature. 10 ml methanol were added. 19.3 ml of the above prepared solution of tetrabutylammonium L-hydrogen tartrate were added to the clear colorless solution. White product starts crystallizing.

The suspension was stirred for a further hour at room temperature. The product was filtered, washed with methanol and dried in vacuum at 35° C. 5.60 g (80%) of a white, crystalline powder were obtained; mp: 129-130° C.; IC: Residual bromide 0.13%.

Impurities (NMR): <1 mol % nicotinamide; 0.35 mol % TBA salt: 0.36 (t, 9H), 1.27 (m, 6H), 1.56 (m, 6H), 3.11 (q, 6H); solvents: 2.4 mol % methanol: 3.26 (s, 3H).

Example 4: The Following Crystalline nicotinamide-β-D-ribofuranoside Salt of the Table was Prepared Analogously to Example 3a

TABLE 1

| Anion | Yield [%] | Mp [° C.] | Residual Bromide (IC) [%] |
|---|---|---|---|
| DL-hydrogen tartrate (FIG. 6) | 90 | 112-114 | 0.1 |

Example 5: Preparation of nicotinamide-β-D-ribofuranoside L-hydrogen Malate From nicotinamide-β-D-ribofuranoside Bromide Using Various Ammonium L-hydrogen Malate Salts for Salt Metathesis Example 5a: Use of TEA•L-hydrogen Malate 5.8 g nicotinamide-β-D-ribofuranoside bromide were suspended in 10 ml methanol upon stirring. 10 ml of a 1.73 molar solution of triethylammonium L-hydrogen malate were added. The suspension was heated until the solids dissolved completely. After cooling, a white solid precipitated. The suspension was stirred for 30 min and then filtered. The residue was washed with methanol and dried in vacuo at 35° C. 4.15 g (62%) of a white crystalline powder was obtained. Mp: 116.5-117° C. IC: Residual bromide 0.10%. The product may be recrystallized from methanol, if desired.

$^1$H-NMR (400 MHz, D$_2$O): 2.53 (dd, 1H, CH$_2$, H-malate), 2.72 (dd, 1H, CH$_2$, H-malate), 3.81 (dd, 1H, H5'), 3.97 (dd, 1H, H5'), 4.28 (t, 1H, H3'), 4.29 (dd, 1H, CHOH, H-malate), 4.38-4.45 (m, 2H, H4', H2'), 6.17 (d, 1H, H1'), 8.20 (t, 1H, H5), 8.90 (d, 1H, H4), 9.19 (d, 1H, H6), 9.52 (s, 1H, H2). Impurities: <1 mol % nicotinamide; 0.7 mol % TEA salt: 1.19 (t, 9H), 3.11 (q, 6H). Solvents: 6.3 mol % methanol: 3.25 (s, 3H).

$^{13}$C-NMR (100 MHz, D$_2$O): 40.0 (CH$_2$, H-malate), 60.2 (C5'), 68.5 (CHOH, H-malate), 69.7 (C3'), 77.4 (C2'), 87.7 (C4'), 99.9 (C1'), 128.4 (C5), 133.9 (C3), 140.4 (C2), 142.6 (C6), 145.6 (C4), 165.7 (CONH2), 176.3 (COO, H-malate), 179.0 (COO, H-malate). Solvents: 48.9 (methanol).

XRD: crystalline (FIG. 2)

Example 5b: Use of TBA•L-hydrogen Malate 3.50 g of L-malic acid (26.0 mMol) were dissolved in 10 ml methanol with stirring. The colorless solution was cooled in an ice bath and 6.3 ml tributylamine (26.0 mMol) were added. The pH of the slightly yellowish solution was around 5. In this manner 17.5 ml of a 1.53 molar solution of tributylammonium L-hydrogen malate was prepared.

5.80 g nicotinamide-β-D-ribofuranoside bromide were suspended in 17.5 ml methanol upon stirring. 11.1 ml of the above prepared solution of tributylammonium L-hydrogen malate were added. The suspension was heated until the solids dissolved completely. After cooling, a white solid crystallized. The suspension was stirred for 30 min and then filtered. The residue was washed with methanol and dried in vacuo at 35° C. 4.89 g (73%) of a white crystalline powder was obtained; mp: 115.5° C.; IC: Residual bromide 0.64%.

Impurities: <1 mol % nicotinamide; 0.2 mol % TBA salt; 2 mol % methanol.

Example 6: The Following Crystalline nicotinamide-β-D-ribofuranoside Salts of the Table Were Prepared Analogously to Example 5a

TABLE 2

| Anion | Yield [%] | Mp [° C.] | Residual Bromide (IC) [%] |
|---|---|---|---|
| 6a: D-hydrogen malate (FIG. 1) | 60 | 117-117.5 | 0.9 |
| 6b: DL-hydrogen malate (FIG. 3) | 67 | 108-109 | 2.3 |
| 6c: D-hydrogen tartrate (FIG. 9) | 70 | 124-126 | 0.3 Water content: 0.3% determined according to K. Fischer |

Example 6d: Recrystallization of Compound 6c to the Monohydrate 2.0 g nicotinamide-β-D-ribofuranoside D-hydrogen tartrate prepared in Example 6c were dissolved in 9 ml water. 70 ml methanol were added to the colorless solution with stirring. After approx. one minute white crystals precipitated. One hour later the formed suspension was filtered. The residue was washed with methanol and dried in vacuo at 35° C. 1.54 g (77%) of a white crystalline powder of the monohydrate was obtained. Water content: 4.24% (determined according to K. Fischer); Mp.: 115-116° C.; IC: Residual bromide: <0.01%.

XRD: crystalline (FIG. 4)

Example 7: Preparation of nicotinamide-β-D-ribofuranoside meso-hydrogen Tartrate 0.57 g nicotinamide-β-D-ribofuranoside bromide were suspended in 1 ml methanol upon stirring. 1 ml of a 1.69 molar solution of triethylammonium meso-hydrogen tartrate was added. The suspension was heated to the boiling point and was then cooled down. The formed emulsion was dropped into 20 ml ethanol. The formed suspension was filtered and the residue was dried at room temperature in vacuo. 0.44 g (62%) of a flaky, hygroscopic powder were obtained.

$^1$H-NMR (400 MHz, D$_2$O): 3.82 (dd, 1H, H5'), 3.97 (dd, 1H, H5'), 4.28 (t, 1H, H3'), 4.38-4.46 (m, 2H, H4', H2'), 4.35 (s, 1.5H, 2×CHOH, meso-H-tartrate), 6.17 (d, 1H, H1'), 8.21 (t, 1H, H5), 8.91 (d, 1H, H4), 9.20 (d, 1H, H6), 9.53 (s, 1H, H2). Impurities: 5 mol % nicotinamide: 7.65 (m, 1H), 8.33 (m, 1H), 8.68 (d, 1H), 8.90 (s, 1H); 10.2 mol % TEA salt: 1.20 (t, 9H), 3.12 (q, 6H). Solvents: 16 mol % methanol: 3.25 (s, 3H); 40 mol % ethanol: 1.09 (t, 3H), 3.56 (q, 2H).

$^{13}$C-NMR (100 MHz, D$_2$O): 60.2 (C5'), 69.7 (C3'), 73.7 (2×CHOH, meso-H-tartrate), 77.4 (C2'), 87.6 (C4'), 99.9 (C1'), 128.4 (C5), 133.9 (C3), 140.4 (C2), 142.6 (C6), 145.6 (C4), 165.8 (CONH2), 175.7 (2×COO, H-tartrate). Impurities: 125.0, 138.6, 146.0, 149.8 (nicotinamide); 8.2, 46.6 (TEA). Solvents: 48.9 (methanol); 16.8, 57.4 (ethanol).

Example 8: Preparation of nicotinamide-β-D-ribofuranoside D-glucuronate 5.10 g of glucuronic acid were suspended in 15 ml methanol with stirring. The colorless suspension was cooled in an ice bath and 3.60 ml triethylamine added. 19.5 ml of a 1.35 molar solution of TEA•D-glucuronate were prepared.

5.0 g nicotinamide-β-D-ribofuranoside bromide were dissolved with stirring in 3.0 ml water at room temperature. 10 ml methanol were added. 11.1 ml of the above prepared solution of triethylammonium D-glucuronate were added. The clear yellowish solution was dropped slowly to 455 ml n-butanol, wherein a white suspension was produced.

The suspension was stirred for further five hours at room temperature. The product was filtered, washed with isopropanol and dried in vacuum at 35° C. 6.64 g of the dried crude product were dissolved in 6.6 ml water and diluted with 33 ml methanol. The yellowish solution was dropped to 550 ml butanol, wherein a white suspension was produced. The suspension was filtered, the residue was washed with isopropanol and dried at 35° C. Mp.: 66-76° C.; residual bromide 1.43% (IC).

$^1$H-NMR (400 MHz, D$_2$O): NR: 3.82 (dd, 1H, H5'), 3.97 (dd, 1H, H5'), 4.28 (t, 1H, H3'), 4.38-4.45 (m, 2H, H4', H2'), 6.17 (d, 1H, H1'), 8.21 (t, 1H, H5), 8.91 (d, 1H, H4), 9.20 (d, 1H, H6), 9.53 (s, 1H, H2); GlcUA (anomeric mixture): 3.19 (m), 3.42 (m), 3.50 (m), 3.63 (m), 4.00 (t), 4.55 (d, β-anomer), 5.14 (d, α-anomer). Impurities: 2 mol % nicotinamide; 0.9 mol % TEA salt: 1.19 (t, 9H), 3.11 (q, 6H). Solvents: 23 mol % methanol: 3.26 (s, 3H); 5.7 mol % butanol: 0.80 (t, 1H, H4), 1.25 (m, 2H, H3), 1.43 (m, 2H, H2).

$^{13}$C-NMR (100 MHz, D$_2$O): NR: 60.2 (C5'), 69.7 (C3'), 77.4 (C2'), 87.6 (C4'), 99.9 (C1'), 128.4 (C5), 133.9 (C3), 140.4 (C2), 142.6 (C6), 145.6 (C4), 165.8 (CONH2); GlcUA: 71.3, 71.7, 71.8, 72.0, 72.5, 74.0, 75.5, 76.1, 92.1, 95.9, 175.7, 176.7. Solvents: 48.9 (methanol); 13.1, 18.4, 33.4, 61.5 (butanol).

Example 9: Nicotinamide-β-D-ribofuranoside L-ascorbate

A crude product was prepared analogously to Example 8, however using ethanol for precipitation. 3.11 g of the crude product were dissolved in 1.9 ml water. The orange clear solution was filtered and diluted with 16 ml methanol. The solution was dropped to 238 ml ethanol, wherein an orange suspension was produced. The product was isolated by filtration and dried at 35° C. 1.13 g of a yellowish powder were obtained (yield 36.3%). IC: Residual bromide 0.38%.

$^1$H-NMR (400 MHz, D$_2$O): 3.82 (dd, 1H, H5'), 3.97 (dd, 1H, H5'), 4.28 (t, 1H, H3'), 4.38-4.45 (m, 2H, H4', H2'), 6.17 (d, 1H, H1'), 8.20 (t, 1H, H5), 8.90 (d, 1H, H4), 9.19 (d, 1H, H6), 9.52 (s, 1H, H2); Ascorbate: 3.64 (m, 2H), 3.92 (m, 1H), 4.43 (m, 1H). Impurities: 16 mol % nicotinamide: 7.49 (t, 1H), 8.13 (d, 1H), 8.60 (d, 1H), 8.82 (s, 1H); no TEA salt. Solvents: 1.3 mol % methanol: 3.25 (s, 3H); 46 mol % ethanol: 1.08 (t, 3H), 3.55 (q, 2H).

$^{13}$C-NMR (100 MHz, D$_2$O): 60.2 (C5'), 69.7 (C3'), 77.4 (C2'), 87.7 (C4'), 99.9 (C1'), 128.4 (C5), 133.9 (C3), 140.4

(C2), 142.6 (C6), 145.6 (C4), 165.8 (CONH2); Ascorbate: 62.5, 69.5, 78.2, 113.3, 174.6, 177.2. Impurities: nicotinamide: 124.2, 129.3, 136.5, 147.6, 151.7. Solvents: 16.8, 57.4 (ethanol).

Example 10: Nicotinamide-β-D-ribofuranoside Citrate 5.52 g citric acid monohydrate were dissolved in 55 ml DMSO with stirring. The colorless solution was cooled in an ice bath and 12 ml triethylamine added. 73 ml of a 0.36 molar solution of TEA•citrate were prepared.

9.0 g nicotinamide-β-D-ribofuranoside bromide were suspended in 18 ml DMSO. 73 ml of the above produced solution were added and heated to 55° C. The brownish solution was added to 1125 ml isopropanol, wherein a white suspension was produced. The solid was isolated by filtration and dried at 35° C. 6.32 g (74%) of a powder were obtained.

3.22 g of the crude product were dissolved in a mixture of 16 ml methanol and 2 ml water. The solution was dropped to 220 ml isopropanol, wherein a white suspension was produced. The solid was isolated by filtration, washed with isopropanol and dried in vacuo at 35° C. 2.67 of a white powder were obtained (82.9%). IC: Residual bromide 0.19%.

$^1$H-NMR (400 MHz, D$_2$O): 2.61 (m, 4H, CH$_2$, citrate), 3.82 (dd, 1H, H5'), 3.97 (dd, 1H, H5'), 4.28 (t, 1H, H3'), 4.38-4.46 (m, 2H, H4', H2'), 6.17 (d, 1H, H1'), 8.21 (t, 1H, H5), 8.90 (d, 1H, H4), 9.20 (d, 1H, H6), 9.52 (s, 1H, H2). Impurities: 6 mol % nicotinamide: 7.50 (dd, 1H), 8.15 (m, 1H), 8.61 (d, 1H), 8.82 (s, 1H); 1.5 mol % TEA salt: 1.19 (t, 9H), 3.11 (q, 6H). Solvents: 31 mol % methanol: 3.26 (s, 3H); 18 mol % isopropanol: 1.08 (d, 6H), 3.92 (m, 1H).

$^{13}$C-NMR (100 MHz, D$_2$O): 44.6 (CH$_2$, citrate), 60.2 (C5'), 69.7 (C3'), 77.4 (C2'), 87.7 (C4'), 99.9 (C1'), 128.4 (C5), 133.9 (C3), 140.4 (C2), 142.6 (C6), 145.6 (C4), 165.7 (CONH2), 176.9 (2×COO, citrate), 180.0 (COO, citrate). Impurities: Nicotinamide: 124.3, 129.3, 136.7, 147.5, 151.6; TEA salt: 8.2, 46.6. Solvents: 48.9 (methanol); 23.7, 64.2 (isopropanol).

Example 11: Preparation of nicotinamide-β-D-riboside-2,3,5-triacetate L-hydrogen Tartrate Example 11a: Via Salt Metathesis From nicotinamide-β-D-riboside-2,3,5-triacetate Bromide 3.90 g L-tartaric acid were dissolved in 10 ml methanol upon stirring. The solution was cooled down to 0-5° C. 3.64 ml triethylamine were added. The pH value was 4.1. 15 ml of a 1.73 molar solution of triethylammonium L-hydrogen tartrate was obtained.

8.0 g of nicotinamide-2,3,5-tri-O-acetyl-β-D-riboside bromide were suspended in 10 ml methanol upon stirring. 10 ml of the above generated triethylammonium L-hydrogen tartrate solution were added. A white crystalline powder slowly started precipitating. The residue obtained after filtration was dried in vacuo at 35° C. 6.00 g (65.2%) of a white crystalline powder was obtained. Mp. 128° C.; IC: residual bromide <0.1%.

$^1$H-NMR (400 MHz, D$_2$O): 2.08, 2.12, 2.15 (3× s, 3× 3H, COCH$_3$), 4.43 (s, 2H, 2×CHOH, H-tartrate), 4.52 (m, 2H, H5'), 4.88 (m, 1H, H4'), 5.44 (t, 1H, H3'), 5.55 (dd, 1H, H2'), 6.58 (d, 1H, H1'), 8.27 (t, 1H, H5), 8.99 (d, 1H, H4), 9.20 (d, 1H, H6), 9.43 (s, 1H, H2). Impurities: <0.1 mol % nicotinamide; 0.6 mol % TEA salt: 1.21 (t, 9H), 3.13 (q, 6H). Solvents: 2 mol % methanol: 3.27 (s, 3H).

$^{13}$C-NMR (100 MHz, D$_2$O): 19.8, 19.9, 20.2 (3×COCH$_3$), 62.6 (C5'), 69.4 (C3'), 72.8 (2× CHOH, H-tartrate), 76.3 (C2'), 82.6 (C4'), 97.3 (C1'), 128.6 (C5), 134.2 (C3), 140.4 (C2), 143.1 (C6), 146.2 (C4), 165.5 (CONH2), 172.3, 172.4, 173.3 (3×CO), 176.3 (2×COO, H-tartrate).

XRD: crystalline (FIG. 7).

Example 11b: Via Ion Exchange Using an Ion Exchanger (for Comparison)

145 g Ambersep 900 in the OH-form were suspended in 110 ml water. Subsequently, 21 g L-tartaric acid were added upon stirring. The ion exchanger loaded with L-hydrogen tartrate was isolated by filtration and washed thrice with water 10.0 g of nicotinamide-2,3,5-tri-O-acetyl-β-D-riboside bromide were dissolved in 70 ml water upon stirring. 22 g of the loaded ion exchanger were added and stirred for 16 minutes. The ion exchanger was separated by filtration and waded twice with water. The filtrate was again subjected to 22 g of the loaded ion exchanger and washed and filtered, wherein the filtrate was collected. This was repeated twice. The filtrate was concentrated. 14.08 g of colorless oil was obtained. The oil was subjected to aqueous methanol, wherein a white suspension was obtained. 9.09 g of a white powder were obtained after filtration and drying.

5.05 g of the amorphous product were dissolved in 25 ml methanol, wherein after some minutes crystallization started. The crystals were isolated by filtration and dried in vacuo at 35° C. 3.92 g, mp. 130° C. XRD was identical to the XRD of the product obtained in Example 11a.

Example 12: Preparation of nicotinamide-2,3,5-tri-O-acetyl-β-D-ribofuranoside Triflate Example 12a: According to the Invention 11.55 g (0.094 mole) of nicotinamide and 29.7 g (0.093 mole) of β-D-ribofuranose 1,2,3,5-tetraacetate were dissolved upon stirring at room temperature in 750 ml acetonitrile which has been dried over a molecular sieve 3 Å. 18.2 ml (0.097 mole) of trimethylsilyl triflate were added within 20 minutes. The yellow solution was stirred for 20 minutes. Subsequently, the solvent was removed in vacuo at 35° C. The formed foam was dissolved in 300 ml dichloromethane and 4.5 g activated charcoal was added. The suspension was filtered. The filtrate was concentrated. 49.5 g (100%) of a yellow foam were obtained.

$^1$H-NMR (400 MHz, D$_2$O): 2.02, 2.06, 2.09 (3× s, 3× 3H, COCH$_3$), 4.45 (m, 2H, H5'), 4.82 (m, 1H, H4'), 5.38 (t, 1H, H3'), 5.49 (dd, 1H, H2'), 6.51 (d, 1H, H1'), 8.22 (t, 1H, H5), 8.92 (d, 1H, H4), 9.13 (d, 1H, H6), 9.37 (s, 1H, H2). Impurities: 3 mol % alpha-anomer, 4 mol % nicotinamide.

$^{13}$C-NMR (100 MHz, D$_2$O): 19.8, 19.9, 20.2 (3×COCH$_3$), 62.6 (C5'), 69.4 (C3'), 76.4 (C2'), 82.7 (C4'), 97.3 (C1'); 114.9+118.1+121.2+124.4 (q, CF3); 128.7 (C5), 134.2 (C3), 140.4 (C2), 143.1 (C6), 146.2 (C4), 165.5 (CONH2), 172.3, 172.4, 173.3 (3×CO).

Example 12b: for Comparison

The method was carried out as described by Tanimori using a high excess of trimethylsilyl triflate, wherein the product was isolated as described in Example 12a. The obtained foam contained a mixture of approx. β-anomer: α-anomer:nicotinamide=2:1:1.

Example 13: Preparation of nicotinamide-β-D-riboside-2,3,5-triacetate L-hydrogen Tartrate From nicotinamide-β-D-riboside-2,3,5-triacetate Triflate Prepared According to Example 12

5.00 g nicotinamide-2,3,5-tri-O-acetyl-β-D-ribofuranoside triflate from Example 12 were dissolved in 50 ml ethanol. 1.42 g L-tartaric acid were added. Subsequently, 1.31 ml triethylamine were added. The generated emulsion was heated for a short time in order to promote crystallization, and cooled down. The formed precipitate was isolated by filtration and dried in vacuo at 30° C. 5.07 g (101.4%) of a white crystalline powder were obtained (mp 127° C.)
$^1$H-NMR (400 MHz, D$_2$O): 2.08, 2.12, 2.16 (3× s, 3× 3H, COCH$_3$), 4.43 (s, 2H, 2×CHOH, H-tartrate), 4.52 (m, 2H, H5'), 4.88 (m, 1H, H4'), 5.44 (t, 1H, H3'), 5.56 (dd, 1H, H2'), 6.58 (d, 1H, H1'), 8.28 (t, 1H, H5), 8.99 (d, 1H, H4), 9.20 (d, 1H, H6), 9.43 (s, 1H, H2). Impurities: <1 mol % nicotinamide; 0.35 mol % TEA salt: 1.21 (t, 9H), 3.13 (q, 6H). Solvents: 2 mol % ethanol: 3.57 (q, 2H), 1.10 (t, 3H).
$^{13}$C-NMR (100 MHz, D$_2$O): 19.8, 19.9, 20.2 (3×COCH$_3$), 62.6 (C5'), 69.4 (C3'), 72.8 (2× CHOH, H-tartrate), 76.3 (C2'), 82.6 (C4'), 97.3 (C1'), 128.6 (C5), 134.2 (C3), 140.4 (C2), 143.1 (C6), 146.3 (C4), 165.5 (CONH2), 172.3, 172.4, 173.3 (3×CO), 176.3 (2×COO, H-tartrate).

Example 14: Preparation of nicotinamide-β-D-riboside-2,3,5-triacetate D-hydrogen Tartrate From nicotinamide-β-D-riboside-2,3,5-triacetate Bromide Crystalline nicotinamide-2,3,5-O-triacetyl-β-D-riboside D-hydrogen tartrate was prepared according to Example 11a.
For comparison, the product was prepared according to the method of Example 11b. The amorphous product subjected to crystallization was identical to the product obtained in Example 11a.
XRD is shown in FIG. 8.

Example 15: Deacylation of nicotinamide-β-D-riboside-2,3,5-triacetate L-hydrogen Tartrate (From Example 11) Exemplifying Pathway 2

Example 15a: Deacylation Using Sulfuric Acid and Neutralization Using Triethylamine Preparation of a diluted sulfuric acid in methanol: 27 g methanol were cooled down to 0° C. 3.00 g sulfuric acid were added while stirring resulting in a 10% methanolic sulfuric acid.
Deacylation of nicotinamide-β-D-riboside-2,3,5-triacetate L-hydrogen tartrate: 3.00 g nicotinamide-β-D-riboside-2,3,5-triacetate L-hydrogen tartrate were suspended in 15 ml methanol while stirring. After addition of 11.7 g of the above methanolic sulfuric acid a yellowish solution was generated. After stirring at room temperature for 5 days, only product and nicotinamide as impurity were present as detected by thin-layer chromatography.
Conversion to nicotinamide-β-D-riboside L-hydrogen tartrate after neutralization with triethylamine: 1.1 ml triethylamine were added to the above solution in order to adjust pH to about 3.5. 0.85 g L-tartaric acid were added. After addition of 0.8 ml triethylamine, the product started crystallizing. The suspension was stirred for another hour and was then stored for 12 hours in a refrigerator. The formed crystals were filtered off, washed with isopropanol and were dried in vacuo at 30° C. 1.01 g (44.2%) of a white crystalline powder having a melting point of 126-127° C. were obtained.
$^1$H-NMR (400 MHz, D$_2$O): 3.82 (dd, 1H, H5'), 3.96 (dd, 1H, H5'), 4.27 (t, 1H, H3'), 4.37-4.45 (m, 2H, H4', H2'), 4.42 (s, 2H, 2×CHOH, H-tartrate), 6.17 (d, 1H, H1'), 8.20 (t, 1H, H5), 8.90 (d, 1H, H4), 9.19 (d, 1H, H6), 9.52 (s, 1H, H2). Impurities: 3 mol % nicotinamide: 7.85 (m, 1H), 8.56 (m, 1H), 8.77 (d, 1H), 9.00 (s, 1H); 3.4 mol % TEA salt: 1.18 (t, 9H), 3.11 (q, 6H). Solvents: 11.3 mol % methanol: 3.25 (s, 3H).
$^{13}$C-NMR (100 MHz, D$_2$O): 60.2 (C5'), 69.7 (C3'), 72.8 (2×CHOH, H-tartrate), 77.4 (C2'), 87.6 (C4'), 99.9 (C1'), 128.4 (C5), 133.9 (C3), 140.4 (C2), 142.6 (C6), 145.6 (C4), 165.8 (CONH2), 176.3 (2×COO, H-tartrate). Impurities: 8.2, 46.6 (TEA salt). Solvents: 48.9 (methanol).

Example 15b: Deacylation Using HBr in Glacial Acetic Acid and Neutralization Using Triethylamine Deacylation of nicotinamide-β-D-riboside-2,3,5-triacetate L-hydrogen tartrate: 3.0 g nicotinamide-β-D-riboside-2,3,5-triacetate L-hydrogen tartrate were suspended in 15 ml methanol while stirring. The suspension was cooled down to 5° C. and 3.0 ml HBr 33% in glacial acetic acid were added. A yellowish solution was generated which was stirred at room temperature for three days. Thin-layer chromatography revealed that deacylation was complete.
Conversion to nicotinamide-β-D-riboside L-hydrogen tartrate after neutralization with triethylamine: 1 ml triethylamine was added in portions to the above solution. 1.5 ml water were added wherein a yellow solution was formed. Subsequently, 0.85 g L-tartaric acid were added. After addition of 0.8 ml triethylamine, product started crystallizing. The product suspension was stirred for another hour at room temperature. The formed crystals were filtered off, washed with 7 ml isopropanol and 5 ml acetone and were dried in vacuo at 30° C. 0.82 g (36%) of a white crystalline powder having a melting point of 129 to 130° C. were obtained.
$^1$H-NMR (400 MHz, D$_2$O): Analogous to Example 15a. Impurities: 1 mol % nicotinamide; 0.1 mol % TEA salt. Solvents: 2.7 mol % methanol.
$^{13}$C-NMR (100 MHz, D$_2$O): Analogous to Example 15a.

Example 16: Deacylation of nicotinamide-2,3,5-tri-O-acetyl-β-D-ribofuranoside Bromide (From Example 1) Exemplifying Pathway 3

Example 16a: Deacylation Using Sulfuric Acid and Neutralization Using Triethylamine Preparation of a diluted sulfuric acid in methanol: 20 ml methanol were cooled down to 0° C. 2.00 g of a 96% sulfuric acid were added while stirring. 21 ml of a 0.93 M methanolic sulfuric acid were obtained.
Deacylation of nicotinamide-2,3,5-tri-O-acetyl-β-D-ribofuranoside bromide: 5.00 g nicotinamide-2,3,5-tri-O-acetyl-β-D-ribofuranoside bromide were suspended in 24.4 ml methanol while stirring, wherein a part of the educt was dissolved. 5.6 ml of the above methanolic sulfuric acid was added. The resulting colorless solution was stirred at room temperature. The solution was stirred for three days wherein a suspension was generated.

Conversion to nicotinamide-β-D-riboside L-hydrogen tartrate after neutralization with triethylamine: 1.36 ml triethylamine were added to the above suspension. After addition of 3.4 ml water, a colorless solution was generated. 1.63 g L-tartaric acid were added, wherein product started precipitating. Further product precipitated after addition of further 1.35 ml triethylamine. The suspension was filtered, the obtained solid was washed with methanol and dried in vacuo at 30° C. 2.4 g (55%) of a crystalline white powder were obtained. Mp. 129.5° C. IC: Residual bromide 0.05%.

$^1$H-NMR (400 MHz, D$_2$O): 3.82 (dd, 1H, H5'), 3.96 (dd, 1H, H5'), 4.27 (t, 1H, H3'), 4.37-4.45 (m, 2H, H4', H2'), 4.42 (s, 2H, 2×CHOH, H-tartrate), 6.17 (d, 1H, H1'), 8.20 (t, 1H, H5), 8.90 (d, 1H, H4), 9.19 (d, 1H, H6), 9.52 (s, 1H, H2). Impurities: 2 mol % nicotinamide: 7.83 (m, 1H), 8.54 (m, 1H), 8.76 (d, 1H), 9.00 (s, 1H); 0.7 mol % TEA salt: 1.19 (t, 9H), 3.11 (q, 6H). Solvents: 7 mol % methanol: 3.25 (s, 3H).

$^{13}$C-NMR (100 MHz, D$_2$O): 60.2 (C5'), 69.7 (C3'), 72.8 (2×CHOH, H-tartrate), 77.4 (C2'), 87.6 (C4'), 99.9 (C1'), 128.4 (C5), 133.9 (C3), 140.4 (C2), 142.6 (C6), 145.6 (C4), 165.8 (CONH2), 176.3 (2×COO, H-tartrate). Solvents: 48.9 (methanol).

Example 16b: Deacylation Using HBr in Glacial Acetic Acid and Neutralization Using Triethylamine Deacylation of nicotinamide-2,3,5-tri-O-acetyl-β-D-ribofuranoside bromide: 5.00 g nicotinamide-2,3,5-tri-O-acetyl-β-D-ribofuranoside bromide were dissolved at room temperature in 30 ml methanol while stirring. After addition of 3.75 ml HBr 33% in glacial acetic acid the formed yellow solution was stirred for three days at room temperature. A white suspension of nicotinamide-β-D-ribofuranoside bromide was generated as controlled by thin-layer chromatography.

Conversion of nicotinamide-β-D-ribofuranoside bromide to nicotinamide-β-D-ribofuranoside L-hydrogen tartrate after neutralization using triethylamine: 2.50 ml triethylamine were added in portions to the above suspension. Subsequently, 2.5 ml water were added. 1.63 g L-tartaric acid were added to the formed yellowish solution. Product started precipitating after further addition of 1.52 ml triethylamine at a pH of 3.5 to 4. The crystalline product was filtered off, washed with 10 ml isopropanol and 10 ml acetone and was dried in vacuo at 30° C. 2.93 g (66.9%) of a white crystalline powder were obtained. Mp. 127.5 to 128.5° C. IC: Residual bromide 0.33%.

1H-NMR (400 MHz, D$_2$O): Analogous to Example 15a. Impurities: 1 mol % nicotinamide; 2.3 mol % TEA salt. Solvents: 7 mol % methanol.

13C-NMR (100 MHz, D$_2$O): Analogous to Example 15a.

Example 16c: Deacylation Using Triethylamine 5.00 g nicotinamide-2,3,5-tri-O-acetyl-β-D-ribofuranoside bromide were dissolved at room temperature in 30 ml methanol while stirring. 1.52 ml triethylamine (1 eq) were added. The yellow solution was stirred for 24 hours. Control by thin-layer chromatography showed nearly complete conversion, however also the formation of nicotinamide. 1.63 g L-tartaric acid were added to the formed suspension. Product started precipitating. The product suspension was stirred for one hour at 0° C., the formed product was isolated by filtration, washed with 12 ml isopropanol and 12 ml acetone and was dried in vacuo at 30° C. 1.86 g (42.4%) of a white powder were obtained. Mp. 127° C.; IC: Residual bromide 0.26%.

1H-NMR (400 MHz, D$_2$O): Analogous to Example 15a. Impurities: 6 mol % nicotinamide; 1.7 mol % TEA salt. Solvents: 18 mol % methanol, 0.5 mol % isopropanol.

13C-NMR (100 MHz, D20): Analogous to Example 15a.

Example 16d: Deacylation Using Triethylamine at 0-5° C.

Example 16c was repeated with the difference that nicotinamide-2,3,5-tri-O-acetyl-β-D-ribofuranoside bromide was subjected to triethylamine at 0° C. Yield was increased to 85.8%.

Example 17: Preparation of nicotinamide-β-D-riboside-2,3,5-triacetate L-hydrogen Tartrate Obtained by Separation of the L-hydrogen Tartrate Salt From a Mixture of β- and α-anomers Generated by Glycosylation of nicotinamide with 1-bromo-2,3,5-triacetyl-D-ribofuranoside Exemplifying Pathway 4

To 100 ml of a crude mixture of anomers (obtained analogously to Example 1), which theoretically contained 54 mmol nicotinamide-D-ribofuranoside-2,3,5-triacetate, 11.7 ml triethylamine were added, wherein the contained acids (HBr and acetic acid) were partially neutralized. 5.16 g L-tartaric acid were added to the orange-yellow solution while stirring. As soon as the tartaric acid was completely dissolved, 4.8 ml triethylamine were added.

The solution was concentrated by distilling 42 ml thereof off, wherein needles of triethylamine hydrobromide started precipitating. 30 ml isopropanol were added and the suspension was cooled down to 0° C. while stirring. The suspension was filtered and the residue (triethylamine hydrobromide) was washed with 14 ml isopropanol.

The filtrate was seeded with some crystals of product. Subsequently, 30 ml tert-butyl-methylether were slowly added, wherein product started precipitating. The product was stored for 12 hours in the refrigerator. After filtration, washing twice with 25 ml isopropanol, respectively, the solid was dried at 35° C. in vacuo. 13.86 g (48.5%) of nicotinamide-β-D-riboside-2,3,5-triacetate L-hydrogen tartrate in the form of white crystal were obtained. Mp. 123-124° C.; IC: Residual bromide 2.64%.

$^1$H-NMR (400 MHz, D$_2$O): 2.08, 2.12, 2.15 (3× s, 3× 3H, COCH$_3$), 4.43 (s, 2H, 2×CHOH, H-tartrate), 4.52 (m, 2H, H5'), 4.88 (m, 1H, H4'), 5.44 (t, 1H, H3'), 5.56 (dd, 1H, H2'), 6.58 (d, 1H, H1'), 8.27 (t, 1H, H5), 8.99 (d, 1H, H4), 9.20 (d, 1H, H6), 9.43 (s, 1H, H2). Impurities: <1 mol % nicotinamide; 20 mol % TEA salt: 1.21 (t, 9H), 3.13 (q, 6H). Solvents: 2.2 mol % isopropanol: 1.09 (d, 6H), 3.93 (m, 1H).

$^{13}$C-NMR (100 MHz, D$_2$O): 19.8, 19.9, 20.2 (3×COCH$_3$), 62.6 (C5'), 69.4 (C3'), 72.8 (2× CHOH, H-tartrate), 76.3 (C2'), 82.6 (C4'), 97.3 (C1'), 128.6 (C5), 134.2 (C3), 140.4 (C2), 143.1 (C6), 146.2 (C4), 165.5 (CONH2), 172.3, 172.4, 173.3 (3×CO), 176.3 (2×COO, H-tartrate). Impurity: TEA salt: 8.2, 46.7.

Example 18: Deacylation of a Mixture of Anomers of nicotinamide-α/β-D-riboside-2,3,5-triacetate Bromide Exemplifying Pathway 5

100 ml of a crude solution containing the anomers (see Example 1), which theoretically contains about 54 mmol nicotinamide-D-ribofuranoside-2,3,5-triacetate bromide was completely concentrated at a temperature in the range of from 35-40° C. by using a rotary evaporator. The resulting yellow viscous oil was diluted with 44 ml methanol. Subsequently, 10 ml HBr 33% in glacial acetic acid were added. The yellowish clear solution was stirred at room temperature. After one day, nicotinamide-β-D-riboside bromide precipitated. After 5 days, complete deacylation was achieved as controlled by thin-layer chromatography.

Separation as nicotinamide-β-D-riboside L-hydrogen tartrate: 7.5 ml triethylamine were added to the above suspension in order to neutralize HBr and acetic acid. After addition of 4 ml water a clear solution was obtained. 8.6 g tartaric acid were added to the yellowish solution which was filtered in order to remove insoluble precipitates. Subsequently, 5.4 ml triethylamine were added, wherein the desired product started precipitating. After filtration and washing with ethanol and methanol, the obtained solid was dried in vacuo at 30° C. 7.27 g (33.3%) of a white crystalline powder were obtained. Mp. 128.5-129.5° C.; IC: residual bromide 0.16%.

$^1$H-NMR (400 MHz, D$_2$O): Analogous to Example 15a. Impurities: 3 mol % nicotinamide; 1.2 mol % TEA salt. Solvents: 7 mol % methanol.

$^{13}$C-NMR (100 MHz, D$_2$O): Analogous to Example 15a.

Example 19: Deacylation of nicotinamide-β-D-riboside-2,3,5-triacetate Triflate Exemplifying Pathway 5

Example 19a: Deacylation Using Sulfuric Acid and Neutralization Using Triethylamine Preparation of a diluted sulfuric acid in methanol: 27 g methanol were cooled down to 0° C. 3.00 g of a 96% sulfuric acid were added while stirring. 30 g of a 10% methanolic sulfuric acid were obtained.

Deacylation of nicotinamide-2,3,5-tri-O-acetyl-β-D-ribofuranoside triflate: 3.00 g nicotinamide-2,3,5-tri-O-acetyl-β-D-ribofuranoside triflate were dissolved in 15 ml methanol while stirring. 5.86 g of the above methanolic sulfuric acid were added. The resulting colorless solution was stirred at room temperature. The solution was stirred for three days. Control by thin-layer chromatography revealed complete deacylation and some nicotinamide impurities.

Conversion to nicotinamide-β-D-riboside L-hydrogen tartrate after neutralization with triethylamine: 1.1 ml triethylamine were added to the above solution. 3.3 ml of a 1.7 molar methanolic solution of triethylammonium L-hydrogen tartrate were added, wherein product immediately started precipitating. Subsequently, 0.40 g L-tartaric acid were added. The product suspension was stored for 12 hours in a refrigerator. After filtration, the obtained solid was washed with methanol and ethanol and dried in vacuo at 30° C. 1.23 g (53.8%) of a white crystalline powder were obtained. Mp. 127 to 128° C.

$^1$H-NMR (400 MHz, D$_2$O): 3.82 (dd, 1H, H5'), 3.96 (dd, 1H, H5'), 4.27 (t, 1H, H3'), 4.37-4.45 (m, 2H, H4', H2'), 4.41 (s, 2H, 2×CHOH, H-tartrate), 6.17 (d, 1H, H1'), 8.20 (t, 1H, H5), 8.90 (d, 1H, H4), 9.19 (d, 1H, H6), 9.51 (s, 1H, H2). Impurities: 2 mol % nicotinamide: 7.83 (m, 1H), 8.54 (m, 1H), 8.76 (d, 1H), 9.00 (s, 1H); 2.9 mol % TEA salt: 1.19 (t, 9H), 3.11 (q, 6H). Solvents: 16 mol % methanol: 3.25 (s, 3H), 2 mol % ethanol.

$^{13}$C-NMR (100 MHz, D$_2$O): 60.2 (C5'), 69.7 (C3'), 72.8 (2×CHOH, H-tartrate), 77.4 (C2'), 87.6 (C4'), 99.9 (C1'), 128.4 (C5), 133.9 (C3), 140.4 (C2), 142.6 (C6), 145.6 (C4), 165.8 (CONH2), 176.3 (2×COO, H-tartrate). Impurities: 8.2, 46.6 (TEA salt). Solvents: 48.9 (methanol).

Example 19b: Deacylation Using HBr in Glacial Acetic Acid and Neutralization Using Triethylamine 8.00 g nicotinamide-2,3,5-tri-O-acetyl-β-D-ribofuranoside triflate were dissolved in 32 ml methanol while stirring. The solution was cooled down to 0-5° C. After addition of 5.2 ml HBr 33% in glacial acetic acid, the solution was kept stirring at room temperature. According to control by thin-layer chromatography, the product was deacylated after two days.

The solution was divided into two halves.

Isolation of the formed intermediate bromide: One half of the solution (20.5 ml) was seeded with nicotinamide-β-D-ribofuranoside bromide and was stirred at room temperature. After about 30 minutes a suspension was formed. The suspension was filtered and the residue was washed with methanol and ethanol and was subsequently dried in vacuo at 30° C. 0.62 g (24.5%) of a white crystalline powder were obtained.

$^1$H-NMR (400 MHz, D$_2$O): 3.83 (dd, 1H, H5'), 3.98 (dd, 1H, H5'), 4.29 (t, 1H, H3'), 4.39-4.48 (m, 2H, H4', H2'), 6.18 (d, 1H, H1'), 8.22 (t, 1H, H5), 8.92 (d, 1H, H4), 9.20 (d, 1H, H6), 9.52 (s, 1H, H2).

$^{13}$C-NMR (100 MHz, D$_2$O): 60.2 (C5'), 69.7 (C3'), 77.4 (C2'), 87.7 (C4'), 99.9 (C1'), 128.5 (C5), 134.0 (C3), 140.4 (C2), 142.7 (C6), 145.7 (C4), 165.8 (CONH2).

Conversion to nicotinamide-β-D-riboside L-hydrogen tartrate after neutralization with triethylamine: 1.8 ml triethylamine were added to the other half of the solution, wherein HBr and acetic acid were partially neutralized. 4.4 ml of a 1.7 molar methanolic solution of triethylammonium L-hydrogen tartrate were added to the yellowish solution, wherein product started precipitating. After filtration and washing with methanol and ethanol and drying in vacuo at 30° C., 1.62 g (53.2%) of a white crystalline powder was obtained. Mp. 127-128° C.

$^1$H-NMR (400 MHz, D$_2$O): Analogous to Example 19a. Impurities: 1 mol % nicotinamide; 3.7 mol % TEA salt. Solvents: 12.5 mol % methanol.

$^{13}$C-NMR (100 MHz, D$_2$O): Analogous to Example 19a.

Example 19c: Deacylation Using Triethylamine

Deacylation of nicotinamide-D-riboside-2,3,5-triacetate triflate: 3.00 g of the triflate were dissolved in 18 ml methanol while stirring. 0.8 ml triethylamine (1 eq) were added to the solution cooled down to 0° C. After stirring for 4 days at 0-5° C., thin-layer control showed complete conversion.

Conversion to nicotinamide-β-D-riboside L-hydrogen tartrate: The brown-orange solution obtained in the step above was warmed to room temperature. Subsequently, 0.86 g L-tartaric acid were added. Product started precipitating. The product suspension was cooled down to 0° C. and stirred. After storage in a refrigerator for 12 hours, the suspension was filtered, the obtained solid washed with 5 ml isopropanol and dried in vacuo at 30° C. 1.44 g (63.0%) of a brown-yellowish crystalline powder were obtained. Mp. 127° C.

$^1$H-NMR (400 MHz, D$_2$O): Analogous to Example 19a. Impurities: 2 mol % nicotinamide; 1.9 mol % TEA salt. Solvents: 13.3 mol % methanol, 4 mol % isopropanol.

$^{13}$C-NMR (100 MHz, D$_2$O): Analogous to Example 19a.

Since one equivalent of triethylamine is necessary for deacylation in the above sequence, it can be concluded that triethylamine surprisingly is catalytically active.

Example 19d: Deacylation Using HBr in Glacial Acetic Acid, Neutralization Using Tributylamine Deacylation of nicotinamide-2,3,5-tri-O-acetyl-D-ribofuranoside triflate: 2.00 g of the triflate were dissolved in 8 ml methanol while stirring. The solution was cooled down to 0-5° C. After addition of 1.3 ml HBr 33% in glacial acetic acid, the green-yellowish solution was stirred at room temperature. After two days no educt could be determined in the solution by thin-layer chromatography.

Conversion to nicotinamide-β-D-ribofuranoside L-hydrogen malate after neutralization with tributylamine: 1.3 ml tributylamine were added to the above solution. After addition of 0.6 ml water, any precipitated material was completely dissolved. 0.51 g L-malic acid was added to the brown-yellowish solution. After addition of further 0.9 ml tributylamine product started crystallizing. Formed product was filtered off, washed with methanol and dried in vacuo at 30° C. 0.48 g (33%) nicotinamide-β-D-ribofuranoside L-hydrogen malate were obtained. Mp. 115.5-116.5° C.

$^1$H-NMR (400 MHz, D$_2$O): 2.55 (dd, 1H, CH$_2$, H-malate), 2.73 (dd, 1H, CH$_2$, H-malate), 3.83 (dd, 1H, H5'), 3.98 (dd, 1H, H5'), 4.28 (t, 1H, H3'), 4.29 (dd, 1H, CHOH, H-malate), 4.39-4.46 (m, 2H, H4', H2'), 6.18 (d, 1H, H1'), 8.21 (t, 1H, H5), 8.91 (d, 1H, H4), 9.20 (d, 1H, H6), 9.53 (s, 1H, H2). Impurities: <1 mol % nicotinamide; 0.35 mol % TBA salt: 0.85 (t, 9H), 1.29 (m, 6H), 1.59 (m, 6H), 3.05 (q, 6H). Solvents: 2.3 mol % methanol: 3.27 (s, 3H).

$^{13}$C-NMR (100 MHz, D$_2$O): 40.0 (CH$_2$, H-malate), 60.2 (C5'), 68.5 (CHOH, H-malate), 69.8 (C3'), 77.4 (C2'), 87.7 (C4'), 99.9 (C1'), 128.4 (C5), 133.9 (C3), 140.4 (C2), 142.6 (C6), 145.6 (C4), 165.8 (CONH2), 176.3 (COO, H-malate), 179.0 (COO, H-malate).

Example 20: Preparation of nicotinamide-2,3,5-tri-O-acetyl-β-D-ribofuranoside Iodide 6.00 g (0.049 mole) of nicotinamide and 14.9 g (0.047 mole) of β-D-ribofuranose 1,2,3,5-tetraacetate were suspended upon stirring at room temperature in 190 ml acetonitrile which has been dried over a molecular sieve 3 Å. The suspension was warmed to 35° C. while most of the solids dissolved. 6.9 ml (0.048 mole) of trimethylsilyl iodide were added within 20 minutes and the yellow suspension was stirred for a further two hours at 35° C. Subsequently, the internal temperature was kept at 40° C. and 45° C. for one hour each. The solvent was removed in vacuo at 35° C. The formed foam was dissolved in 100 ml dichloromethane and 1.2 g activated charcoal was added. The suspension was filtered. The filtrate was concentrated. 22 g (93%) of a deep yellow foam were obtained.

$^1$H-NMR (400 MHz, D$_2$O): 2.05, 2.07, 2.12 (3× s, 3× 3H, COCH$_3$), 4.46 (m, 2H, H5'), 4.84 (m, 1H, H4'), 5.41 (t, 1H, H3'), 5.53 (dd, 1H, H2'), 6.58 (d, 1H, H1'), 8.28 (t, 1H, H5), 8.94 (d, 1H, H4), 9.18 (d, 1H, H6), 9.38 (s, 1H, H2). Impurities: 15 mol % alpha-anomer, 3 mol % nicotinamide.

$^{13}$C-NMR (100 MHz, D$_2$O): 20.0, 20.1, 20.4 (3×COCH$_3$), 62.6 (C5'), 69.3 (C3'), 76.1 (C2'), 82.5 (C4'), 97.2 (C1'), 128.8 (C5), 134.1 (C3), 140.4 (C2), 143.1 (C6), 146.2 (C4), 165.1 (CONH2), 172.0, 172.1, 173.0 (3×CO).

Example 21: Deacylation of nicotinamide-β-D-riboside-2,3,5-triacetate Iodide Exemplifying Pathway 5

Deacylation Using Sulfuric Acid and Neutralization Using Triethylamine

Preparation of a diluted sulfuric acid in methanol: 10 ml methanol were cooled down to 0° C. 1.20 ml of a 96% sulfuric acid were added while stirring. The methanolic sulfuric acid was used in the deacetylation below.

Deacylation of nicotinamide-2,3,5-tri-O-acetyl-β-D-ribofuranoside iodide: 11.0 g nicotinamide-2,3,5-tri-O-acetyl-β-D-ribofuranoside iodide were dissolved in 33 ml methanol while stirring. The above prepared methanolic sulfuric acid was added. The resulting orange-brown solution was stirred at room temperature for one day. Control by thin-layer chromatography revealed complete deacylation and some impurities. 3.5 ml triethylamine were added.

The solution was divided into two halves.

Conversion to nicotinamide-β-D-riboside L-hydrogen tartrate after neutralization with triethylamine: To one half of the above solution 1.65 g L-tartaric acid were added, followed by further 1.6 ml triethylamine. Product started precipitating almost immediately. The product suspension was stirred one hour at ambient temperature, two hours in an ice-bath and stored for 12 hours in a refrigerator. After filtration, the obtained solid was washed with methanol and dried in vacuo at 30° C. 2.10 g (48%) of an almost white crystalline powder of nicotinamide-β-D-ribofuranoside L-hydrogen tartrate were obtained. Mp. 125.5-126° C.

$^1$H-NMR (400 MHz, D$_2$O): Analogous to Example 19a. Impurities: 1 mol % nicotinamide; 3.8 mol % TEA salt. Solvents: 18.2 mol % methanol.

$^{13}$C-NMR (100 MHz, D20): Analogous to Example 19a.

Conversion to nicotinamide-β-D-riboside L-hydrogen malate after neutralization with triethylamine: 1.45 g L-malic acid were added to the other half of the above solution, followed by further 1.1 ml triethylamine. The solution was seeded. Product started precipitating a few minutes later. The product suspension was stirred one hour at ambient temperature and two hours in an ice-bath, then stored for 12 hours in a refrigerator. After filtration, the obtained solid was washed with methanol and ethanol and dried in vacuo at 30° C. 1.37 g (32.7%) nicotinamide-β-D-ribofuranoside L-hydrogen malate were obtained as an almost white crystalline solid. Mp. 114-115° C.

$^1$H-NMR (400 MHz, D$_2$O): Analogous to Example 19d. Impurities: 0.5 mol % nicotinamide; 0.5 mol % TEA salt. Solvents: 2.4 mol % methanol, 0.4 mol % ethanol.

$^{13}$C-NMR (100 MHz, D$_2$O): Analogous to Example 19d.

We claim:

1. A crystalline form of nicotinamide-β-D-ribofuranoside hydrogen tartrate.

2. The crystalline form of claim 1, wherein the crystalline form is a crystalline form of nicotinamide-β-D-ribofuranoside hydrogen L-tartrate.

3. The crystalline form of claim 2, wherein the crystalline form is characterized by a powder X-ray diffraction pattern having one or more peaks as provided in Table 5, ±0.2 degrees two theta.

4. The crystalline form of claim 2, wherein the crystalline form is characterized by a powder X-ray diffraction pattern having the following peaks 17.0±0.2, 22.7±0.2, and 23.6±0.2 degrees two theta.

5. The crystalline form of claim 2, wherein the crystalline form is characterized by a powder X-ray diffraction pattern having the following peaks 17.0±0.2, 22.7±0.2, 23.6±0.2, and 27.5±0.2 degrees two theta.

6. The crystalline form of claim 1, wherein the crystalline form is a crystalline form of nicotinamide-β-D-ribofuranoside hydrogen D-tartrate.

7. The crystalline form of claim 6, wherein the crystalline form is a crystalline form of nicotinamide-β-D-ribofuranoside hydrogen D-tartrate monohydrate or anhydrous nicotinamide-β-D-ribofuranoside hydrogen D-tartrate.

8. The crystalline form of claim 7, wherein the crystalline form is a crystalline form of nicotinamide-β-D-ribofuranoside hydrogen D-tartrate monohydrate, wherein the crystalline form is characterized by a powder X-ray diffraction pattern having one or more peaks as provided in Table 4, ±0.2 degrees two theta.

9. The crystalline form of claim 8, wherein the crystalline form is characterized by a powder X-ray diffraction pattern having the following peaks 16.4±0.2, 21.7±0.2 and 24.0±0.2 degrees two theta.

10. The crystalline form of claim 8, wherein the crystalline form is characterized by a powder X-ray diffraction pattern having the following peaks 16.4±0.2, 21.7±0.2, 23.2±0.2, 24.0±0.2, 26.3±0.2, and 29.8±0.2 degrees two theta.

11. The crystalline form of claim 7, wherein the crystalline form is a crystalline form of anhydrous nicotinamide-β-D-ribofuranoside hydrogen D-tartrate, wherein the crystalline form is characterized by a powder X-ray diffraction pattern having one or more peaks as provided in Table 9, ±0.2 degrees two theta.

12. The crystalline form of claim 11, wherein the crystalline form is characterized by a powder X-ray diffraction pattern having the following peaks 12.9±0.2, 17.5±0.2 and 21.4±0.2 degrees two theta.

13. The crystalline form of claim 11, wherein the crystalline form is characterized by a powder X-ray diffraction pattern having the following peaks 12.9±0.2, 16.4±0.2, 17.5±0.2, 21.4±0.2, 22.2±0.2, and 26.1±0.2 degrees two theta.

14. The crystalline form of claim 1, wherein the crystalline form is a crystalline form of nicotinamide-β-D-ribofuranoside hydrogen DL-tartrate.

15. The crystalline form of claim 14, wherein the crystalline form is characterized by a powder X-ray diffraction pattern having one or more peaks as provided in Table 6, ±0.2 degrees two theta.

16. The crystalline form of claim 14, wherein the crystalline form is characterized by a powder X-ray diffraction pattern having the following peaks 17.0±0.2, 22.8±0.2 and 24.5±0.2 degrees two theta.

17. The crystalline form of claim 14, wherein the crystalline form is characterized by a powder X-ray diffraction pattern having the following peaks 12.6±0.2, 21.6±0.2 and 27.8±0.2 degrees two theta.

18. The crystalline form of claim 14, wherein the crystalline form is characterized by a powder X-ray diffraction pattern having the following peaks 12.6=0.2, 17.0±0.2, 21.6±0.2, 22.8±0.2, 24.5±0.2, and 27.8±0.2 degrees two theta.

19. A nutritional supplement comprising a crystalline form of claim 1.

20. A pharmaceutical composition comprising a crystalline form of claim 1.

21. A crystalline nicotinamide-β-D-ribofuranoside salt or crystalline nicotinamide-2,3,5-O-triacetyl-β-D-ribofuranoside salt selected from the group consisting of:
  (a) crystalline nicotinamide-β-D-ribofuranoside hydrogen D-tartrate monohydrate characterized by a powder X-ray diffraction pattern as defined in FIG. 4;
  (b) crystalline nicotinamide-β-D-ribofuranoside hydrogen L-tartrate characterized by a powder X-ray diffraction pattern as defined in FIG. 5;
  (c) crystalline nicotinamide-β-D-ribofuranoside hydrogen DL-tartrate characterized by a powder X-ray diffraction pattern as defined in FIG. 6;
  (d) crystalline nicotinamide-2,3,5-O-triacetyl-β-D-ribofuranoside hydrogen L-tartrate characterized by a powder X-ray diffraction pattern as defined in FIG. 7;
  (e) crystalline nicotinamide-2,3,5-O-triacetyl-β-D-ribofuranoside hydrogen D-tartrate characterized by a powder X-ray diffraction pattern as defined in FIG. 8; and
  (f) crystalline anhydrous nicotinamide-β-D-ribofuranoside hydrogen D-tartrate characterized by a powder X-ray diffraction pattern as defined in FIG. 9.

* * * * *